US009427482B2

(12) United States Patent
Rossin et al.

(10) Patent No.: US 9,427,482 B2
(45) Date of Patent: Aug. 30, 2016

(54) AGENTS FOR CLEARING BIOMOLECULES FROM CIRCULATION

(75) Inventors: Raffaella Rossin, Eindhoven (NL); Tilman Laeppchen, Eindhoven (NL); Sandra Martina Van Den Bosch, Weert (NL); Marc Stefan Robillard, Eindhoven (NL); Ronny Mathieu Versteegen, Hegelsom (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 29 days.

(21) Appl. No.: 13/994,783

(22) PCT Filed: Dec. 16, 2011

(86) PCT No.: PCT/IB2011/055730
§ 371 (c)(1),
(2), (4) Date: Jun. 17, 2013

(87) PCT Pub. No.: WO2012/085789
PCT Pub. Date: Jun. 28, 2012

(65) Prior Publication Data
US 2013/0272959 A1    Oct. 17, 2013

(30) Foreign Application Priority Data
Dec. 21, 2010 (EP) .................................. 10196092

(51) Int. Cl.
| A61K 51/00 | (2006.01) |
| A61M 36/14 | (2006.01) |
| A61K 51/04 | (2006.01) |
| A61K 47/48 | (2006.01) |
| A61K 51/10 | (2006.01) |
| B82Y 5/00 | (2011.01) |
| A61K 45/06 | (2006.01) |
| A61K 31/495 | (2006.01) |

(52) U.S. Cl.
CPC ............. *A61K 51/044* (2013.01); *A61K 45/06* (2013.01); *A61K 47/4873* (2013.01); *A61K 47/48746* (2013.01); *A61K 51/0495* (2013.01); *A61K 51/1027* (2013.01); *A61K 51/1045* (2013.01); *A61K 51/1093* (2013.01); *B82Y 5/00* (2013.01); *A61K 31/495* (2013.01)

(58) Field of Classification Search
None
See application file for complete search history.

(56) References Cited

U.S. PATENT DOCUMENTS

| 4,741,900 A | 5/1988 | Alvarez et al. |
| 5,326,856 A | 7/1994 | Coughlin et al. |
| 5,616,690 A | 4/1997 | Axworthy et al. |
| 5,624,896 A | 4/1997 | Axworthy et al. |
| 5,886,143 A | 3/1999 | Theodore et al. |
| 5,965,131 A | 10/1999 | Griffiths et al. |
| 6,075,010 A | 6/2000 | Theodore et al. |
| 6,172,045 B1 | 1/2001 | Theodore et al. |
| 6,908,903 B1 | 6/2005 | Theodore et al. |
| 7,052,872 B1 | 5/2006 | Hansen et al. |
| 2003/0129191 A1 | 7/2003 | Theodore et al. |
| 2014/0308332 A1 | 10/2014 | Lynch et al. |

FOREIGN PATENT DOCUMENTS

| WO | 9515978 A1 | 6/1995 |
| WO | 9515979 A1 | 6/1995 |
| WO | 9617613 A1 | 6/1996 |
| WO | 9746098 A1 | 12/1997 |
| WO | 2006038185 A2 | 4/2006 |
| WO | 2007039858 A1 | 2/2007 |
| WO | 2010051530 A1 | 3/2010 |
| WO | 2010119382 A2 | 10/2010 |
| WO | 2010119389 A2 | 10/2010 |

OTHER PUBLICATIONS

Elliott et al. (J. Am. Chem. Soc. 2006, 128, 10589-10595).*
Rossin, R. et al. "In vivo chemistry for pretargeted tumor imaging in live mice", Angewandte Chemie International Edition 2010, 49, 3375.
Devaraj, N.K. et al. "Tetrazine-Based Cycloadditions: Application to Pretargeted Live Cell Imaging", Bioconjugate Chem. 2008, 19, 2297-2299.
Thalhammer, F, Wallfahrer, U. et al. "Reaktivitat einfacher offenkettiger und cyclischer dienophile bei Diels-Alder-reaktionen mit inversem elektronenbedarf" Tetrahedron Letters, 1990, 31(47), 6851-6854.
Wijnen, J.W. et al. "Substituent Effects on an inverse electron demand hetero diels alder reaction in aqueous solution and organic solvents cycloaddition of substituted styrenes to El(2-Pyridyl)-1,2,4,5-Tetrazine". Journal of Organic chemistry, 1996, 61, 2001-2005.
Blackman, M.L. et al. "The tetrazine ligation: fast bioconjugation based on inverse-electron-demand diels-alder reactivity", Journal of the American Chemical Society, 2008, 130 (41) 13518-19.

(Continued)

*Primary Examiner* — Michael G Hartley
*Assistant Examiner* — Melissa Perreira

(57) ABSTRACT

Described is a method, and a combination of agents for used therein, by which an agent administered to a subject can be rapidly cleared from circulation. This is achieved by providing an Administration Agent (e.g. a probe for pretargeting) with a reactive group and providing a Clearing Agent with another reactive group, said reactive groups forming a bio-orthogonally reactive pair. Preferably, the reactive pair comprises a cyclooctene or cyclooctyn as one reactant, and a diene as the other reactant. The method and combination can be used for the removal of any bindable molecule from circulation, such as an excess of a pre-targeting probe in the course of a pre-targeting method, a targeting or imaging agent delivered, or the removal of any biomolecule already present in circulation.

10 Claims, 14 Drawing Sheets

(56) References Cited

OTHER PUBLICATIONS

Royzen, M. et al., "A photochemical synthesis of functionalized trans-cyclooctenes driven by metal complexation". Journal of the American Chemical Society 2008, 130, 3760.

Devaraj, N.K. et al. "Fast and Sensitive Pretargeted labeling of cancer cells via tetrazine/trans-cyclooctene cycloaddition", Angew Chem Int. Ed 2009, 48, 7013.

Devaraj et al, Angew Chem Int. Ed., 2009, 48, 1-5.

Goldenberg, D.M. et al. "Antibody pretargeting advances cancer radioimmunodetection and radioimmunotherapy", J Clin Oncol 24:823-834, 2006.

Boerman, O.C. et al. "Pretargeted Radioimmunotherapy of Cancer: progress step by step", J Nucl Med 2003, 44, 400.

Goldenberg, D.M. et al. "Radioimmunotherapy: Is avidin-biotin pretargeting the preferred choice among pretargeting methods?", , European Journal of Nuclear Medicine and Molecular Imaging 2003, 30, 777.

Begent, R.H.J. et al., "Liposomally entrapped second antibody improves tumour imaging with radiolabelled (first) antitumour antibody", The Lancet 1982, 320, 739.

Pedley, R.B. et al. "The effect of second antibody clearance on the distribution and dosimetry of radiolabelled anti-cea antibody in a human colonic tumor xenograft model", International Journal of Cancer 1989, 43, 713.

Sharma, S.K. "Accelerated clearance systems", Advanced Drug Delivery Reviews 1996, 22, 315.

Sinitsyn, V.V., "Rapid blood clearance of biotinylated IgG after infusion of avidin", J Nucl Med 1989, 30, 66.

Marshall, D. et al. "Galactosylated streptavidin for improved clearance of biotinylated intact and F(ab)2 fragments of an anti-tumour antibody", British Journal Cancer 1995, 71, 18.

* cited by examiner procedure 1 procedure 2

AGENTS FOR CLEARING BIOMOLECULES FROM CIRCULATION

FIELD OF THE INVENTION

The invention relates to clearing agents for the clearing of biomolecules from circulation in a subject, such as agents that are administered to said subject for purposes such as targeted drug therapy, targeted imaging, pre-targeting. The invention particularly relates to clearing agents for use in a pretargeting method. The invention also relates to the use of the clearing agents for the removal of a biomolecule from circulation, such as the capture of circulating fractions of target moieties, or of previously administered therapeutic or imaging agents.

BACKGROUND OF THE INVENTION

In many areas of medical diagnosis and therapy, it is desired to selectively deliver an agent, such as a therapeutic agent (a drug) or a diagnostic (e.g. imaging) agent, to a specific site, or a confined region, in the body of a subject such as a patient.

Active targeting of an organ or a tissue is achieved by the direct or indirect conjugation of the desired active moieties (e.g. a contrast enhancing agent or a cytotoxic compound) to a targeting construct, which binds to cell surfaces or promotes cellular uptake at or near the target site of interest. The targeting moieties used to target such agents are typically constructs that have affinity for cell surface targets (e.g., membrane receptors), structural proteins (e.g., amyloid plaques), or intracellular targets (e.g., RNA, DNA, enzymes, cell signalling pathways). These moieties can be antibodies (fragments), proteins, aptamers, oligopeptides, oligonucleotides, oligosaccharides, as well as peptides, peptoids and organic drug compounds known to accumulate at a particular disease or malfunction. Alternatively, a contrast/therapeutic agent may target a metabolic pathway, which is upregulated during a disease (like infection or cancer) such as DNA, protein, and membrane synthesis and carbohydrate uptake. In diseased tissues, abovementioned markers can discriminate diseased cells from healthy tissue and offer unique possibilities for early detection, specific diagnosis and (targeted) therapy.

An important criterion for successful molecular imaging/therapy agents in general and nuclear imaging/therapy agents in particular is that they exhibit a high target uptake while showing a rapid clearance (through renal and/or hepatobiliary systems) from non-target tissue and from the blood. However, this is often problematic: for example, imaging studies in humans have shown that the maximum concentration of a radio labeled antibody at the tumor site is attainable within 24 h but several more days are required before the concentration of the labeled antibody in circulation decreases to levels low enough for successful imaging to take place.

These problems (especially for nuclear imaging and therapy) with slow or insufficient accumulation in target tissue and slow clearance from non-target areas have lead to the application of pre-targeting approaches.

Pretargeting refers to a step in a targeting method, wherein a primary target (e.g. a cell surface) is provided with a Pre-targeting Probe. The latter comprises a secondary target, which will eventually be targeted by a further probe (the Effector Probe) equipped with a secondary targeting moiety.

Thus, in pre-targeting, a Pre-targeting Probe is bound to a primary target. The Pre-targeting Probe also carries secondary targets (sometimes also referred as "tags"), that facilitate specific conjugation to a diagnostic (imaging) and/or therapeutic agent, the Effector Probe. After the construct forming the Pre-targeting Probe has localized at the target site (taking time, e.g. 24 h), excess of the Pre-Targeting Probe has to be removed from the blood.

As natural clearance frequently is not sufficient, it is desired to use a clearing agent. Clearing agents work to remove compounds from circulation by directing them to a specific organ or tissue. Thus, in general, a clearing agent is an agent capable of binding, complexing or otherwise associating with an administered moiety (e.g., targeting moiety-ligand, targeting moiety-anti-ligand or anti-ligand alone) present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that reduce clearing agent access to the population of target cells recognized by a targeting moiety used in the same treatment protocol as the clearing agent. Typically, clearing agents bind to the pre-targeting antibody. Alternatively, it would be desired to provide clearing agents that by mere rapid clearance from circulation prior to being able to access a target cell. To this end, it is desired to provide clearing agents capable of reacting fast (exhibiting a high reaction rate with the biomolecule to be cleared).

In US 2003/0129191 clearing agents are disclosed that incorporate ligand derivatives or anti-ligand derivatives. Herein, essentially, such derivatives exhibit a lower affinity for the complementary ligand/anti-ligand pair member than the native form of the compound. Thus, e.g., where a biotin-avidin or biotin-streptavidin ligand/anti-ligand pair is employed, the clearing agents incorporate either a biotin derivative exhibiting a lower affinity for avidin or streptavidin than biotin or an avidin or a streptavidin derivative exhibiting a lower affinity for biotin than avidin or streptavidin.

Rossin et al., Angew. Chem. Int., Ed 2010, 49, p. 3375-3378 relates to tumor pretargeting by using the inverse-electron-demand Diels-Alder reaction.

WO 2010/119382 A1 and WO 2010/119389 A2 refer to pretargeting methods involving the use of [4+2] inverse-electron-demand (retro) Diels-Alder chemistry in providing the coupling between a pretargeting probe and an effector probe.

U.S. Pat. No. 7,052,872 B1 relates to a bi-specific antibody or antibody fragment having at least one arm that specifically binds a targeted tissue and at least one arm that specifically binds a targetable conjugate.

U.S. Pat. No. 5,965,131 A refers to a pretargeting method for delivering diagnostic or therapeutic agents to a target site using a clearing agent that binds to the target-binding site of the targeting species, wherein anti-idiotype antibodies and antibody fragments are preferred clearing agents.

Moreover, the current pretargeting systems are hampered by factors associated with their biological nature. Biotin is an endogenous molecule and its conjugates can be cleaved by the serum enzyme biotinidase. When antisense pre-targeting is used, the oligonucleotides can be subject to attack by RNAse and DNAse. Proteins and peptides are also subject to natural decomposition pathways. These interactions can be further impaired by their non-covalent and dynamic nature and limited on-target residence time. Also, endogenous biotin competes with biotin conjugates for streptavidin binding. Finally, streptavidin is highly immunogenic.

Further, the imaging of targets is sometimes hampered by circulating fractions of said target, that capture the imaging agents before they can reach the target at the desired locus. It is desired that a system be provided by which such circulating targets can be removed prior to administering the imaging agent. Also in other circumstances, e.g. as a therapy, it can be desired to remove biomolecules from circulation. E.g., if therapy is directed to interaction with an enzyme such as MMP-2 (matrix metalloproteinase-2) that occurs in the extracellular matrix of certain tumors, but also in serum, a clearance concept will be desired. Another example is CEA (carcinoembryonic antigen) which is a target for (pre) targeting of radioimmunotherapy, but it also occurs in serum and will therein capture radioactivity.

Other examples are antibody conjugates used for Antibody Directed Enzyme Prodrug Therapy (ADEPT), where it would be beneficial to remove any antibody conjugate from circulation prior to administering the prodrug. Other therapeutic agents that could benefit from a clearing approach are antibody-drug conjugates. These conjugates circulate for a long time but comprise highly toxic drugs, requiring the conjugate linker to be highly stable. Using a clearing agent would allow to remove any free antibody drug conjugate from circulation after sufficient amount has bound to the tumor.

It is desired that a clearing concept be found that is versatile, that allows providing clearing agents that rapidly bind to administered moieties to be cleared from circulation, and that can be used in pre-targeting approaches.

OBJECTS AND SUMMARY OF THE INVENTION

There is thus a strong need to provide a novel clearing agent which meets the high demands for a clearing agent as described above. The present invention is inter alia based on the recognition that the clearing agent as described herein reacts rapidly in blood without reacting rapidly on the target, e.g. a tumor, thereby leaving the target-bound molecules, e.g. TCOs as will be defined herein below, free for the reaction with the pretargeting probe. In order to better address one or more of the foregoing desires, the invention, in one aspect, provides a combination of an Administration Agent to be administered to a subject and a Clearing Agent to be administered to the same subject so as to remove circulating Administration Agent from the subject's blood, wherein the Administration Agent comprises a first Reactive Group, and wherein the Clearing Agent comprises a second Reactive Group, said first and second Reactive Groups being Bio-orthogonal Reactive Groups selected so as to be bio-orthogonally reactive towards each other wherein either of the Bio-orthogonal Reactive Groups is a dienophile and the other is a diene, wherein the dienophile is an 8-member ring dienophile satisfying formula (1):

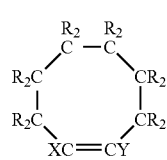

(1)

wherein each R independently denotes H, or, in at most six instances, a substituent selected from the group consisting of alkyl, aryl, O-aryl, O-alkyl, S-aryl, S-alkyl, S(O)-aryl, S(O)- alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, N$_3$, SO$_2$H, SO$_3$H, SO$_4$H, PO$_3$H, PO$_4$H, OH, SH, NO$_2$, NO, CN, OCN, SCN, NCO, NCS, CF$_3$, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl, wherein two R moieties together may form a ring, and wherein X and Y each independently denote H, or a substituent selected from the group consisting of alkyl, O-alkyl, S-alkyl, F, Cl, Br, I, SO2, NO2, and NRR' with R and R' each independently being H or alkyl, or together form a bond, with one R forming a linkage, optionally via a spacer, to the respective Administration Agent or Clearing Agent.

The invention, in another aspect, presents a kit for targeted medical imaging and/or therapeutics, comprising at least one Pre-targeting Probe and at least one Effector Probe, wherein the Pre-targeting Probe comprises a Primary Targeting Moiety and a first Bio-orthogonal Reactive Group, and wherein the Effector Probe comprises an Effector Moiety, such as a label or a pharmaceutically active compound, and a second Bio-orthogonal Reactive Group, said second Bio-Orthogonal Reactive group being reactive to the first Bio-Orthogonal Reactive Group, the kit further comprising a Clearing Agent having a Reactive Group that is bio-orthogonally reactive to the first Bio-Orthogonal Reactive Group.

In yet another aspect, the invention resides in the use of bio-orthogonal reaction pairs for providing an Administration Agent to be administered to a subject, and a Clearing Agent for the removal of said Administration Agent from circulation in said subject.

In a still further aspect, the invention pertains to a Clearing Agent comprising a compound having one or more hexose moieties and a diene moiety.

In an alternative further aspect, the invention pertains to a Clearing Agent comprising a compound having one or more hexose moieties and a dienophile moiety.

In still another aspect, the invention presents a method for removing a biomolecule from circulation in an animal or human subject, the method comprising administering an Administration Agent and a Clearance Agent, wherein the Administration Agent comprises a first Reactive Group, and wherein the Clearing Agent comprises a second Reactive Group, said first and second Reactive Groups being selected so as to be bio-orthogonally reactive towards each other. In a related further aspect, the invention pertains to the use of an Administration Agent and a Clearing agent as defined above, for removing a biomolecule from circulation in an animal or human subject.

DETAILED DESCRIPTION OF THE INVENTION

Figure 1:
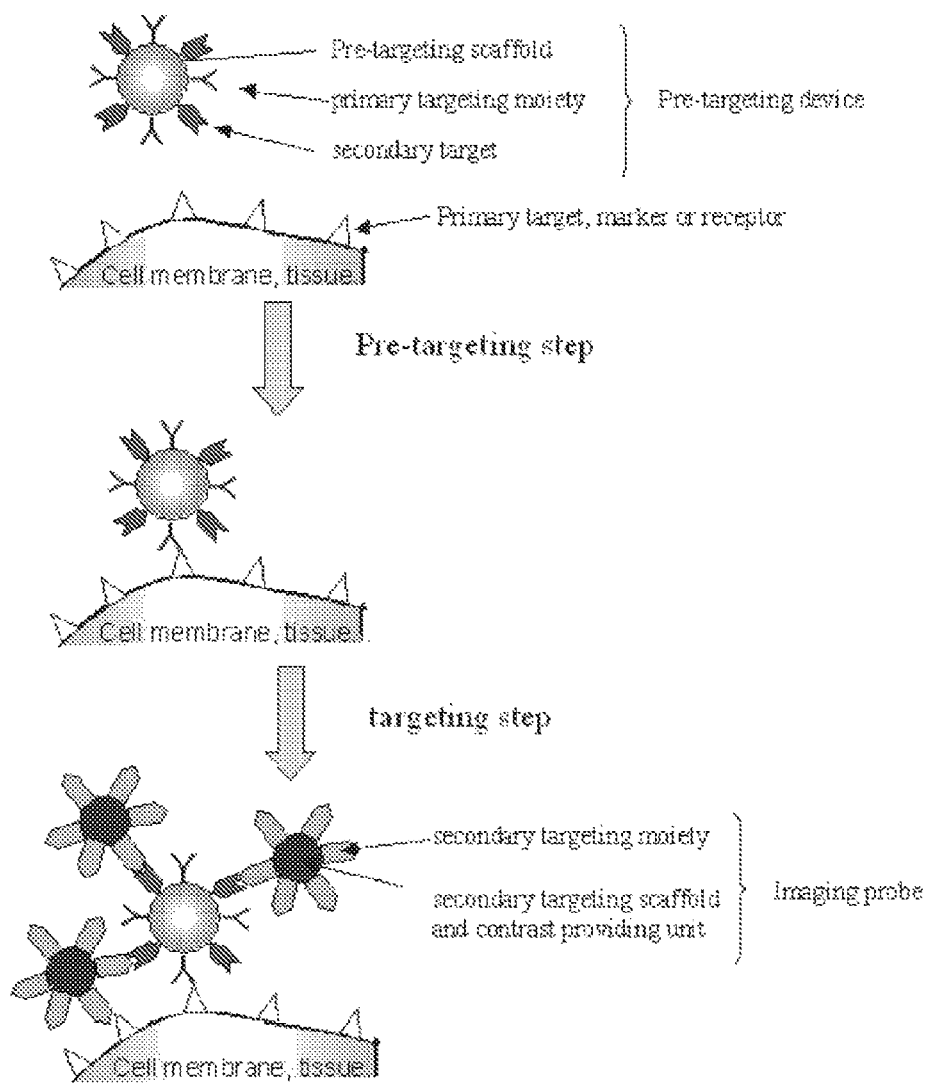
FIG. 1 depicts a general scheme of a pretargeting concept, as discussed above

In a broad sense, the invention pertains to the judicious recognition that bio-orthogonal chemistry (such as emerging in modern pre-targeting concepts) can be used for the removal of basically any bindable molecule from circulation in animal, and preferably a human, subject. A bindable molecule is to be understood as any molecule, generally of a biochemical or organic nature, for which a binder or ligand (including antibodies) can be provided. A bindable molecule can be a molecule (such as circulating fractions of proteins) already present in circulation. It can also be a molecule administered for the purpose of acting in the body (such as a pre-targeting probe), and of which excess is to be removed from circulation.

The invention, in one aspect, presents the concept to administer such a ligand via an Administration Agent comprising a first bio-orthogonally reactive group, and subsequently administering a Clearing Agent comprising a second bio-orthogonally reactive group, said groups being capable of undergoing a bio-orthogonal reaction with each other.

The present invention provides a combination of an Administration Agent and a Clearing Agent. The term "combination" is to be understood in broad sense, not limited to a kit comprising both components. Thus, the Administration Agent and the Clearing Agent can be provided totally separately of each other. It will be understood that the function of the Clearing Agent is to act in combination with an Administration Agent.

An Administration Agent in the present invention is an agent, compound or moiety administered to a subject and of which removal from circulation is desired. This removal can pertain to the removal of the Administration Agent per se (such as excess pre-targeting agent that is desired to be removed) or a to a conjugate formed by the administration agent and a circulating biomolecule (such as circulating fractions of biological targets hampering the imaging of the bound fraction of such targets). Thus, in some embodiments, an Administration Agent will be administered for the purpose of being targeted to a certain location in the body, e.g. to a tumor, after which circulating excess of the agent is to be removed. In another embodiment, an Administration Agent will be administered for the purpose of capturing circulating fractions of targets to be imaged, or to which local therapy is to be delivered, so as to remove these circulating fractions before the non-circulating actual (e.g. tumor cell-bound) target is imaged or the targeted therapeutic agent is delivered. In this embodiment, the Administration Agent does not require a step of pre-targeting, but can itself comprise a ligand for the target to be imaged. The Administration Agent can also be an agent for targeted imaging or therapeutics, e.g. an antibody-drug conjugate (i.e. not necessarily involving pre-targeting). E.g. an injectable, radiolabeled mAb that is injected, circulates and (partially) binds to a tumor, followed by injecting a clearing agent so as to transport the radioactive mAb to the liver.

A Clearing Agent is an agent, compound, or moiety that is administered to a subject for the purpose of binding to, or complexing with, the Administration Agent to be removed and which is capable of being directed to removal from circulation. The latter is generally achieved through liver receptor-based mechanisms, although other ways of secretion from circulation exist.

In a broad sense, the invention is based on the recognition that bio-orthogonal reactive pairs can be used for the purpose of clearing administered agents from circulation. To this end, the Administration Agent has a reactive group that is capable of undergoing a bio-orthogonal reaction with a complementary (bio-orthogonal) reactive group. The latter is present in a Clearing Agent (the particulars of which are further discussed below).

The recognition that bio-orthogonal chemistry can be used for the purpose of clearance from circulation opens up a wide array of possibilities. In fact, any agent to be administered, such as a drug or an imaging agent, can be provided with a tag in the form of a bio-orthogonal reactive group. And any agent capable of affecting clearance from circulation, can be provided with a complementary tag in the form of a bio-orthogonal reactive group that is capable of undergoing a bio-orthogonal reaction with said first reactive group.

The concept of clearing of administered agents from circulation is of general relevance in targeted therapy and targeted imaging, and particularly in pre-targeting approaches.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

It is furthermore to be noticed that the term "comprising", used in the description and in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In several chemical formulae reference is made to "alkyl" and "aryl." In this respect "alkyl", each independently, indicates an aliphatic, straight, branched or cyclic alkyl group of up to ten carbon atoms, possibly including 1-3 heteroatoms such as O, N, or S, preferably of 1-6 carbon atoms and "aryl," each independently, indicates an aromatic or heteroaromatic group of up to ten carbon atoms, possibly including 1-3 heteroatoms such as N or S. In several formulae, groups or substituents are indicated with reference to letters such as "A", "B", "X", "Y", and various numbered "R" groups. The definitions of these letters are to be read with reference to each formula, i.e. in different formulae, these letters, each independently, can have different meanings unless indicated otherwise.

In further preferred embodiments of the present invention, in several chemical formulae below reference is made to "alkyl" and "aryl." In this respect "alkyl", each independently, indicates an aliphatic, straight, branched, saturated, unsaturated and/or or cyclic hydrocarbyl group of up to ten carbon atoms, possibly including 1-10 heteroatoms such as O, N, or S, and "aryl", each independently, indicates an aromatic or heteroaromatic group of up to twenty carbon atoms, that possibly is substituted, and that possibly includes 1-10 heteroatoms such as O, N, P or S. "Aryl" groups also include "alkylaryl" or "arylalkyl" groups (simple example: benzyl groups). The number of carbon atoms that an "alkyl", "aryl", "alkylaryl" and "arylalkyl" contains can be indicated by a designation preceding such terms (i.e. $C_{1-10}$ alkyl means that said alkyl may contain from 1 to 10 carbon atoms). Certain compounds of the invention possess chiral centers and/or tautomers, and all enantiomers, diasteriomers and tautomers, as well as mixtures thereof are within the scope of the invention.

Administration Agent

The clearing concept of the invention is of relevance for the clearance from circulation of a previously administered Administration Agent. The Administration Agent can be any agent of which it is desired to remove excess from circulation. This particularly is the case in the event of targeted delivery of drugs or imaging agents to a site, such as a tumor, within the body of a subject, notably a human subject. It does not play any particular role in the invention which function or chemical structure the Administration Agent has. The sole requirement is that it can be provided with a Bio-orthogonal Reactive Group. The precise linkage of the Bio-orthogonal Reactive Group to the Administration Agent will depend on the molecular structure of both, but it should be noted that this does not normally present a particular challenge to the person skilled in the art, as many proven linkage moieties for various biomolecules exist. The linkage can, optionally, be via a spacer such as polyethylene glycol (PEG) chains varying from 2 to 200, particularly 3 to 113 and preferably 5-50 repeating units.

In a preferred embodiment, the Administration Agent is a Pre-targeting Probe as used in the pre-targeted delivery of therapeutic or imaging agents and the like. Here, the reactive functionality added to the Administration Agent, viz. either of the Bio-orthogonal Reactive Groups of a pair of bio-orthogonal reactants, has a function in both the clearing from circulation and in the subsequent attachment of an Effector Probe to the Pre-targeting Probe.

In yet another preferred embodiment, the Administration Agent comprises a ligand for a biomolecule already present in circulation. This refers to, e.g., a monoclonal antibody for a protein target that is to be imaged, or to which local drug therapy is to be delivered. It is noted that this is generally applicable to a wide range of biological targets, and corresponding ligands, known to the skilled person.

In a still further embodiment, the Administration Agent comprises a conjugate of a targeting moiety (such as an antibody) and a drug (or an imaging agent) to be targeted.

Clearing Agent

The Clearing Agent comprises as its minimum components, a clearance-directing component and a binding component. The binding component is a bioorthogonal reactive group, as discussed above. The clearance-directing component serves to ensure removal from circulation, by directing the captured Administration Agent to an excretory organ.

The Clearing Agents of the invention circulate in blood for a relatively short time but are sufficiently reactive to bind the residual Administration Agent (such as a monoclonal antibody tag) in blood before leaving the circulation. They do not have sufficient time or opportunity to react with e.g. a. tumor bound mAb-tag, either because of size or because of interaction with liver hexose receptors, or as a result of the rate at which they leave circulation.

Optionally, Clearing Agents can be used that are capable of producing an imageable signal. Thus, a non-invasive imaging technique can be used to monitor the distribution of the Clearing Agent in a subject's body.

The Clearing Agent will generally have a size, configuration, charge, or any combination of properties, which serves to avoid the Clearing Agent from itself being bound to the previously administered Administration Agent in its desired location (i.e. the Clearing Agent will bind to circulating excess of Administration Agent, not substantially to targeted species thereof). To this end, the Clearing Agent will generally comprise a scaffold. Suitable scaffolds are known to the skilled person and include, e.g., proteins, dendrimers and high molecular weight polymers. Another preferred clearing agent comprises a nano- or micro-particle scaffold, e.g. a liposome or polymersome, a lipid or polymer or protein shell bubble, a lipid or polymer or protein particle, an iron oxide or gold or silica particle, a quantum dot, a carbon nanotube, a capsule filled with iodine compounds or other nano- and micro-structures, modified with bio-orthogonal reactive groups. The particle itself functions as the clearance directing group.

Preferred clearing agents include hexose-based and non-hexose based moieties. Hexose-based clearing agents are molecules that have been derivatized to incorporate one or more hexoses (six carbon sugar moieties) recognized by Ashwell receptors or other receptors such as the mannose/N-acetylglucosamine receptor which are associated with hepatocytes, endothelial cells and/or Kupffer cells of the liver or the mannose 6-phosphate receptor.

Exemplary of such hexoses are galactose, mannose, mannose 6-phosphate, N-acetylglucosamine, pentamannosyl-phosphate, and the like. Other moieties recognized by Ashwell receptors, including glucose, N-galactosamine, N-acetylgalactosamine, pentamannosyl phosphate, thioglycosides of galactose and, generally, D-galactosides and glucosides or the like may also be used in the practice of the present invention. Galactose is the prototypical clearing agent hexose derivative for the purposes of this description. Galactose thioglycoside conjugation to a protein is preferably accomplished following a procedure largely similar to the teachings of Lee et al., "2-Imino-2-methoxyethyl 1-Thioglycosides: New Reagents for Attaching Sugars to Proteins," *Biochemistry*, 15(18): 3956, 1976. Another useful galactose thioglycoside conjugation method is set forth in Drantz et al, "Attachment of Thioglycosides to Proteins: Enhancement of Liver Membrane Binding," *Biochemistry*, 15(18): 3963, 1976.

Bio-Orthogonal Reactive Groups

The invention generally is applicable to all pairs of abiotic reactive chemical groups that exhibit bio-orthogonal reactivity towards each other. Bio-orthogonal reactions take place under physiological conditions, whereby the Bio-Orthogonal Reactive Groups recognize only each other, while ignoring their cellular/physiological surroundings.

Examples of such reactions are widespread, and in fast development. Recent advances are the Staudinger ligation, i.e. in which the reaction partners are an azide and a phoshine. For use in a pretargeting method, for targeted medical imaging and/or therapeutics, this has been described in WO 2006/038185. Another example is the [3+2] azide-alkyne cycloaddition as described in WO 2007/039858, also known as "click chemistry." Another type of coupling chemistry is described by Neal K. Devaraj, Ralph Weissleder, and Scott Hilderbrand in Bioconjugate Chem. 2008, 19, 2297-2299. This relates to the application of bioorthogonal tetrazine cycloadditions to live cell labeling. The reaction partners herein are 3-(p-benzylamino)-1,2,4,5-tetrazine and a norbornene, viz. (1S,2S,4S)-bicyclo[2,2,1]hept-5-en-2-yl acetic acid, which undergo a Diels-Alder cycloaddition followed by a retro Diels-Alder reaction, in which dinitrogen ($N_2$) is released. This coupling chemistry is also referred to as an inverse electron-demand Diels-Alder reaction. Another example hereof is in WO 2010/051530, wherein pretargeting is discussed on the basis of the reactivity between certain dienes, such as tetrazines and dienophiles such as a trans-cyclooctenol (TCO). Other references on the Inverse electron demand Diels Alder reaction (or "retro Diels-Alder reaction"), and the behavior of the pair of reactive species include: Thalhammer, F; Wallfahrer, U; Sauer, J, Tetrahedron Letters, 1990, 31(47), 6851-6854; Wijnen, J W; Zavarise, S; Engberts, JBFN, Journal Of Organic Chemistry, 1996, 61, 2001-2005; Blackman, M L; Royzen, M; Fox, J M, Journal Of The American Chemical Society, 2008, 130 (41), 13518-19); R. Rossin, P. Renart Verkerk, Sandra M. van den Bosch, R. C. M. Vulders, I. Verel, J. Lub, M. S. Robillard, Angew Chem Int Ed 2010, 49, 3375-78; N. K. Devaraj, R. Upadhyay, J. B. Haun, S. A. Hilderbrand, R. Weissleder, Angew Chem Int Ed 2009, 48, 7013, and Devaraj et al., Angew. Chem. Int. Ed., 2009, 48, 1-5.

It will be understood that the Administration Agent will have either of the two Bio-orthogonal Reactive Groups that form a bio-orthogonal reactive pair, and the Clearing Agent will have the other of such pair. In the preferred use of the Clearing Agents, first a Pre-targeting Probe is administered. Ultimately, an Effector Probe will be administered that serves to react to the Pre-targeting probe in its desired site (e.g. a tumor cell). The reactive groups on the Effector Probe and on the Clearing Agent may be identical or different, but will share a reactivity towards the Bio-orthogonal Reactive Group on the Pre-targeting Probe. E.g., if the Pre-targeting Probe comprises a dienophile, both the Clearing Agent and the Effector Probe will comprise a diene, but these dienes are not necessarily the same.

Preferably, the Administration Agent and the Clearing Agent are selected so as to be capable of a bio-orthogonal [4+2] cyclo-addition. More preferably, both agents react with each other via a "retro Diels-Alder reaction."

The Retro Diels-Alder coupling chemistry generally involves a pair of reactants that couple to form an unstable intermediate, which intermediate eliminates a small molecule (depending on the starting compounds this may be e.g. $N_2$, $CO_2$, RCN), as the sole by-product through a retro Diels-Alder reaction to form a stable product. The paired reactants comprise, as one reactant (i.e. one Bio-orthogonal Reactive Group), a suitable diene, such as a derivative of tetrazine, and, as the other reactant (i.e. the other Bio-orthogonal Reactive Group), a cyclooctene or cyclooctyne according to formula (1) below.

Figure 2:
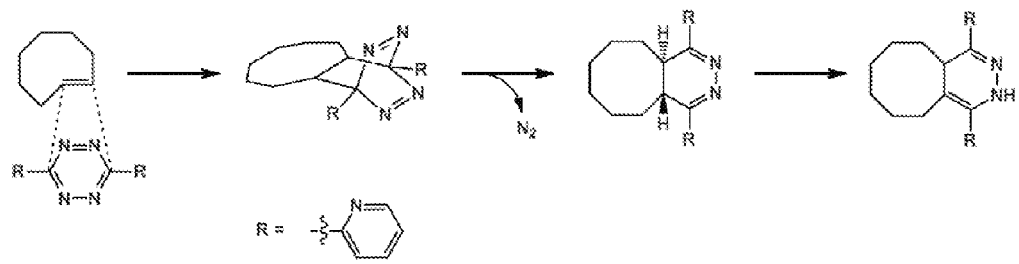
FIG. 2 provides the reaction scheme for a [4+2] Diels-Alder reaction between (3,6)-di-(2-pyridyl)-s-tetrazine and E-cyclooctene followed by a retro Diels Alder reaction in which the product and dinitrogen is formed. This type of Diels Alder reaction is frequently referred to as an "inverse electron demand Diels Alder reaction". In the following text the sequence of both reaction steps, i.e. the initial Diels-Alder cyclo-addition (typically an inverse electron demand Diels Alder cyclo-addition) and the subsequent retro Diels Alder reaction will be referred to in shorthand as "retro Diels Alder reaction" or "retro-DA".

The exceptionally fast reaction of, e.g., electron-deficient (substituted) tetrazines with e.g. strained E-cyclooctene results in a ligation intermediate that rearranges to a stable dihydropyridazine by eliminating $N_2$ as the sole by-product in a [4+2] Retro Diels-Alder cycloaddition. This is shown in FIG. 2.

The two reactive species are abiotic and thus do not undergo a fast metabolism in vivo. They are bio-orthogonal, e.g. they selectively react with each other in physiologic media. References on the Inverse electron demand Diels Alder reaction, and the behavior of the pair of reactive species include: Thalhammer, F; Wallfahrer, U; Sauer, J, Tetrahedron Letters, 1990, 31(47), 6851-6854; Wijnen, J W; Zavarise, S; Engberts, JBFN, Journal Of Organic Chemistry, 1996, 61, 2001-2005; Blackman, M L; Royzen, M; Fox, J M, Journal Of The American Chemical Society, 2008, 130 (41), 13518-19.

According to preferred typical embodiment of the present invention, either of the Bio-orthogonal Reactive Groups is a dienophile and the other is a diene, wherein the dienophile is an 8-member ring dienophile satisfying formula (1):

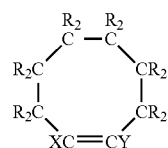
(1)

wherein each R independently denotes H, or, in at most six instances, a substituent selected from the group consisting of alkyl, aryl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, N$_3$, SO$_2$H, SO$_3$H, SO$_4$H, PO$_3$H, PO$_4$H, OH, SH, NO$_2$, NO, CN, OCN, SCN, NCO, NCS, CF$_3$, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl, wherein two R moieties together may form a ring, and wherein X and Y each independently denote H, or a substituent selected from the group consisting of alkyl, O-alkyl, S-alkyl, F, Cl, Br, I, SO$_2$, NO$_2$, and NRR' with R and R' each independently being H or alkyl, or together form a bond. Herein one R will form a linkage, optionally via a spacer, to either a functional component of the Administration Agent or a functional component of the Clearing Agent. In the former case this will typically comprise a linkage to a Pre-targeting Probe, in the latter case it will be a linkage to a clearance-directing moiety.

The person skilled in the art is aware of the wealth of dienes that are reactive in the Retro Diels-Alder reaction. Preferred dienes are given below, with reference to formulae (2)-(7).

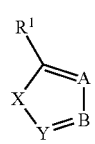
(2)

wherein R$^1$ is selected from the group consisting of H, alkyl, aryl, CF$_3$, CF$_2$—R', OR', SR', C(=O)R', C(=S)R', C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", NR'C(=O)NR"R'", NR'C(=S)N'R"R'" with R', R", and R'" each independently being H, aryl or alkyl; A and B each independently are selected from the group consisting of alkyl-substituted carbon, aryl substituted carbon, nitrogen, N$^+$O$^-$, N$^+$R with R being alkyl, with the proviso that A and B are not both carbon; X is selected from the group consisting of O, N-alkyl, and C=I, and Y is CR with R being selected from the group consisting of H, alkyl, aryl, C(=O)OR', C(=O)SR', C(=S)OR', C(=S)SR', C(=O)NR'R" with R' and R" each independently being H, aryl or alkyl; A diene particularly suitable as a reaction partner for cyclooctene is:

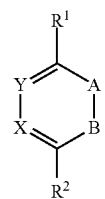
(3)

wherein R$^1$ and R$^2$ each independently are selected from the group consisting of H, alkyl, aryl, CF$_3$, CF$_2$—R', NO$_2$, OR', SR', C(=O)R', C(=S)R', OC(=O)R'", SC(=O)R'", OC(=S)R'", SC(=S)R'", S(=O)R', S(=O)$_2$R'", S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R'R" with R' and R" each independently being H, aryl or alkyl, and R'" independently being aryl or alkyl; A is selected from the group consisting of N-alkyl, N-aryl, C=O, and CN-alkyl; B is O or S; X is selected from the group consisting of N, CH, C-alkyl, C-aryl, CC(=O)R', CC(=S)R', CS(=O)R', CS(=O)$_2$R'", CC(=O)O—R', CC(=O)S—R', CC(=S)O—R', CC(=S)S—R', CC(=O)NR'R", CC(=S)NR'R", R' and R" each independently being H, aryl or alkyl and R'" independently being aryl or alkyl; Y is selected from the group consisting of CH, C-alkyl, C-aryl, N, and N$^+$O$^-$.

A comparable diene particularly suitable as a reaction partner for cyclooctyne is:

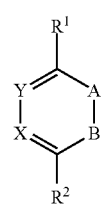
(4)

wherein R$^1$ and R$^2$ each independently are selected from the group consisting of H, alkyl, aryl, OH, C(=O)O-alkyl, CF$_3$, C(=O)NH-alkyl, and NO$_2$; A is selected from the group consisting of CO, C-alkyl-alkyl, CN-alkyl, N-alkyl, and N-aryl; B is selected from the group consisting of CH, C-alkyl, C-aryl, CC(=O)O-alkyl and N; Y is selected from the group consisting of CH, C-alkyl, C-aryl, N, and N$^+$O$^-$.

Another diene particularly suitable as a reaction partner for cyclooctene is:

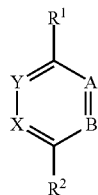
(5)

wherein R¹ and R² each independently are selected from the group consisting of H, alkyl, aryl, CF₃, CF₂—R', NO₂, OR', SR', C(=O)R', C(=S)R', OC(=O)R''', SC(=O)R''', OC(=S)R''', SC(=S)R''', S(=O)R', S(=O)₂R''', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR'R'', NR'C(=S)N'R'R'' with R' and R'' each independently being H, aryl or alkyl, and R''' independently being aryl or alkyl; A is selected from the group consisting of N, C-alkyl, C-aryl, and N⁺O⁻; B is N; X is selected from the group consisting of N, CH, C-alkyl, C-aryl, CC(=O)R', CC(=S)R', CS(=O)R', CS(=O)₂R''', CC(=O)O—R', CC(=O)S—R', CC(=S)O—R', CC(=S)S—R', CC(=O)NR'R'', CC(=S)NR'R'', R' and R'' each independently being H, aryl or alkyl and R''' independently being aryl or alkyl; Y is selected from the group consisting of CH, C-alkyl, C-aryl, N, and N⁺O⁻.

A comparable diene particularly suitable as a reaction partner for cyclooctyne is:

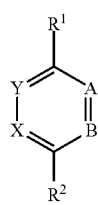
(6)

wherein R¹ is selected from the group consisting of H, alkyl, aryl, OH, C(=O)O-alkyl, CF₃, and NO₂; R² is selected from the group consisting of H, alkyl, aryl, CN, OH, C(=O)O-alkyl, CF₃, and NO₂;

A is selected from the group consisting of N, CH, C-alkyl, C-aryl, CC(=O)O-alkyl, and N⁺O⁻; B is N; X is selected from the group consisting of CH, C-alkyl, C-aryl, CC(=O)O-alkyl and N; Y is selected from the group consisting of CH, CCN, C-alkyl, C-aryl, N, and N⁺O⁻.

Particularly useful tetrazine derivatives are electron-deficient tetrazines, i.e. tetrazines substituted with groups or moieties that do not generally hold as electron-donating, and preferably carrying electron-withdrawing substituents.

These electron-deficient tetrazines generally satisfy the following structural formula:

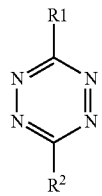
(7)

Herein R¹ and R² each independently denote a substituent selected from the group consisting of H, 2-pyridyl, 3, pyridyl, 4-pyridyl, 2,6-pyrimidyl, 2,5-pyrimidyl, 3,5-pyrimidyl, 2,4-pyrimidyl, or phenyl, optionally substituted with one or more electron-withdrawing groups such as NO₂, F, Cl, CF₃, CN, COOH, COOR, CONH₂, CONHR, CONR₂, CHO, COR, SO₂R, SO₂OR, NO, Ar, wherein R is C₁-C₆ alkyl and Ar stands for an aromatic group, particularly phenyl, pyridyl, or naphthyl.

In the compounds according to each of the formulae (2)-(7), the R¹ and R² groups (including those on X or Y), can further be provided with suitable linker or spacer moieties as discussed below. Analogously, and independently thereof, also the dienophile of formula (1) can further be provided with suitable linker or spacer moieties as discussed below.

The strained cyclooctene dienophile used in the present invention is hereinafter denoted E-cyclooctene. With reference to the conventional nomenclature, it will be understood that, as a result of substitution X or Y, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dienophiles according to the present invention, also in the event that substituents would formally require the opposite nomenclature. I.e., the invention relates to cyclooctene in which carbon atoms 1 and 6 as numbered below are in the E (entgegen) or trans position.

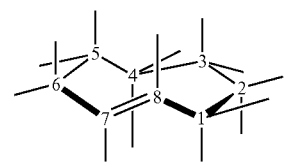

In a further preferred embodiment, the dienophile is a cyclooctene satisfying formula (1a)

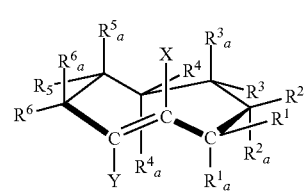
(1a)

wherein the position of R is equatorial and the position of R$_a$ is axial, wherein each of X, Y, R, and R$_a$ independently denotes H, or, in at most six instances, a substituent selected from the group consisting of alkyl, aryl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, N$_3$, SO$_2$H, SO$_3$H, SO$_4$H, PO$_3$H, PO$_4$H, OH, SH, NO$_2$, NO, CN, OCN, SCN, NCO, NCS, CF$_3$, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl; with one of R or R$_a$ comprised in a Linker Moiety, optionally via a spacer, to either the Administration Agent or the Clearing Agent; wherein two R or R$_a$ moieties together may form a ring; and wherein at least one and maximally four of R$_a$ is not hydrogen.

These preferred, axially substituted cyclooctene dienophiles allow achieving increased reaction rates for the bio-orthogonal coupling reaction up to ten times or more. Or, put otherwise, a reaction time that is only 10% of the time originally required. Or, put still otherwise, the concentration of one reactant can be 10 times lower.

As explained above, at least one and maximally four of R$_a$ is not hydrogen, meaning that such R$_a$ is a substituent or is part of a linker structure. Preferably, the number of non-hydrogen R$_a$ is one or two.

More preferably, the at least one, and maximally four of the non-hydrogen R$_a$ are in the position selected from the group consisting of R$^2_a$, R$^3_a$, R$^4_a$, and R$^5_a$. Still more preferably, one or two of R$^2_a$, R$^3_a$, R$^4_a$, and R$^5_a$ are non-hydrogen. Most preferably, a substituent or linker structure is present as one or both of R$^3_a$ and R$^4_a$.

Preferably the substituent is selected from the group defined above with reference to formula (1a) as defined above. More preferably, the aforementioned R$_a$ is alkyl or O-alkyl, more preferably methyl or O-t-butyl. In particularly preferred embodiments the aforementioned R$_a$ is aryl or O-alkyl.

It should be noted that the options and preferences for R$_a$ are irrespective of whether or not any substituents are present in the equatorial position (i.e. the R groups in formula (1a) as defined above), on another carbon atom or on the same carbon atom. Preferably, in addition to one or two axial substituents, also one or two equatorial substituents are present, said substituents preferably including the R or R$_a$ that is part of a linker structure. However, in another preference, with a view to striking a balance between synthesis efforts and reactivity, it is preferred that one or two R$_a$ are not hydrogen, and all other R and R$_a$ are hydrogen.

In a further preference, X and/or Y are O-alkyl or alkyl, more preferably methyl.

In preferred embodiments, the dienophiles e.g. tetrazines may exhibit a wide range of reactivities and stabilities which can be employed in the design of probes tailored to a particular application. For example, tetrazine moieties with reduced reactivity compared to the tetrazine moiety on the pretargeting probe may be used in the clearing agent to prevent a situation where the clearing agent reacts with tumor-bound TCO and blocks the pretargeting probe.

Pre-Targeting Probe

As mentioned above, in a preferred embodiment the Administration Agent is a Pre-targeting Probe.

The general concept of pre-targeting is outlined for imaging in FIG. 1. Herein the Effector Probe is an imaging probe comprising a detectable label for an imaging modality. The Effector Probe binds to the (pre)-bound Pre-targeting Probe via its secondary targeting groups.

A Pre-targeting Probe comprises a moiety that is capable of binding to the primary target of interest.

Targeting moieties are typically constructs that have affinity for cell surface targets (e.g., membrane receptors), structural proteins (e.g., amyloid plaques), or intracellular targets (e.g., RNA, DNA, enzymes, cell signalling pathways). These moieties can be antibodies (fragments), proteins, aptamers, oligopeptides, oligonucleotides, oligosaccharides, as well as peptides, peptoids and organic drug compounds known to accumulate at a particular disease or malfunction.

Particular embodiments of suitable primary targeting moieties for use in the kits of the present invention are described herein and include receptor binding peptides and antibodies. A particular embodiment of the present invention relates to the use of small targeting moieties, such as peptides, so as to obtain a cell-permeable targeting probe.

A "primary targeting moiety" as used in the present invention relates to the part of the targeting probe which binds to a primary target. Particular examples of primary targeting moieties are peptides or proteins which bind to a receptor. Other examples of primary targeting moieties are antibodies or fragments thereof which bind to a cellular compound. Antibodies can be raised to non-proteinaceous compounds as well as to proteins or peptides. Other primary targeting moieties can be made up of aptamers, oligopeptides, oligonucleotides, oligosaccharides, as well as peptoids and organic drug compounds. A primary targeting moiety preferably binds with high specificity, with a high affinity, optionally even covalently, and the bond with the primary target is preferably stable within the body.

In order to allow specific targeting of the above-listed primary targets, the primary targeting moiety of the targeting probe can comprise compounds including but not limited to antibodies, antibody fragments, e.g. Fab2, Fab, scFV, diabodies, polymers (tumor targeting by virtue of EPR effect), proteins, peptides, e.g. octreotide and derivatives, VIP, MSH, LHRH, chemotactic peptides, bombesin, elastin, peptide mimetics, carbohydrates, monosaccharides, polysaccharides, viruses, whole cells, phage, drugs, chemotherapeutic agents, receptor agonists and antagonists, cytokines, hormones, steroids. Examples of organic compounds envisaged within the context of the present invention are, or are derived from, estrogens, e.g. estradiol, androgens, progestins, corticosteroids, paclitaxel, etoposide, doxorubicin, methotrexate, folic acid, and cholesterol.

According to a particular embodiment of the present invention, the primary target is a receptor and suitable primary targeting moieties include but are not limited to, the ligand of such a receptor or a part thereof which still binds to the receptor, e.g. a receptor binding peptide in the case of receptor binding protein ligands.

Other examples of primary targeting moieties of protein nature include interferons, e.g. alpha, beta, and gamma interferon, interleukins, and protein growth factor, such as tumor growth factor, e.g. alpha, beta tumor growth factor, platelet-derived growth factor (PDGF), uPAR targeting protein, apolipoprotein, LDL, annexin V, endostatin, and angiostatin.

Alternative examples of primary targeting moieties include DNA, RNA, PNA and LNA which are e.g. complementary to the primary target.

According to a particular embodiment of the invention, small lipophilic primary targeting moieties are used which can bind to an intracellular primary target.

According to a further particular embodiment of the invention, the primary target and primary targeting moiety are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting primary targets with tissue-, cell- or disease-specific expression. For example, membrane folic acid receptors mediate intracellular accumulation of folate and its analogs, such as methotrexate. Expression is limited in normal tissues, but receptors are overexpressed in various tumor cell types.

According to one embodiment, the Pre-targeting Probe and the Effector Probe can be multimeric compounds, comprising a plurality of primary and/or secondary targets and/or targeting moieties. These multimeric compounds can be polymers, dendrimers, liposomes, polymer particles, or other polymeric constructs. Of particular interest for amplifying the signal of detection are targeting probes with more than one secondary target, which allow the binding of several Effector Probes.

The Pre-targeting Probe further comprises the above-mentioned first Bio-orthogonal Reactive group. This group serves as a "secondary target", i.e. as the part of the targeting probe that provides the first reaction partner for the retro Diels-Alder coupling chemistry.

Said secondary target—can be either partner of the coupling reaction, as described above. I.e. in one preferred embodiment it is an electron-deficient tetrazine. In another preferred embodiment it is a cyclooctene or cyclooctyne of formula (1), and more preferably an axially substituted cyclooctene of formula (1a).

In the Pre-targeting Probe, the primary targeting moiety and the first Bio-orthogonal Reactive Group can be directly linked to each other. They can also be bound to each other via a linker, and furthermore they can both be linked to a primary targeting scaffold, e.g. a biopolymer such as a polypeptide. I.e. in the most simple sense, the Linker Moiety is a bond. Suitable Linker Moieties further include, but are not limited to polyethylene glycol (PEG) chains varying from 2 to 200, particularly 3 to 113 and preferably 5-50 repeating units. By adjusting the PEG chain length, one can influence the circulation time of the probes in the physiological system. This is of particular relevance for the Pre-targeting Probe (as the initial targeting step of linking the primary targeting moiety to the primary target may involve a relatively slow process, requiring a relatively lengthy circulation time). Linker moieties optionally include biopolymer fragments, such as oligo or polypeptides or polylactides.

It will be understood that the invention encompasses any conceivable manner in which the diene and the dienophile are attached to either of the pre-targeting or effector probes. Methods of affecting conjugation to these probes, e.g. through reactive amino acids such as lysine or cysteine, are known to the skilled person.

According to one embodiment, the invention is used for targeted imaging.

According to this embodiment, imaging of a specific primary target is achieved by specific binding of the primary targeting moiety of the Pre-targeting Probe and detection of this binding using detectable labels comprised in the Effector Probe.

Primary Target

A "primary target" as used in the present invention relates to a target to be detected in a diagnostic and/or imaging method, and/or to be modulated, bound, or otherwise addressed by a pharmaceutically active compound, or other therapeutic modality.

The primary target can be selected from any suitable targets within the human or animal body or on a pathogen or parasite, e.g. a group comprising cells such as cell membranes and cell walls, receptors such as cell membrane receptors, intracellular structures such as Golgi bodies or mitochondria, enzymes, receptors, DNA, RNA, viruses or viral particles, antibodies, proteins, carbohydrates, monosaccharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-)angiogenesis marker, gastrin receptor, dopaminergic system, serotonergic system, GABAergic system, adrenergic system, cholinergic system, opoid receptors, GPIIb/IIIa receptor and other thrombus related receptors, fibrin, calcitonin receptor, tuftsin receptor, integrin receptor, VEGF/EGF receptors, EGF, matrix metalloproteinase (MMP), P/E/L-selectin receptor, LDL receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase.

According to a particular embodiment of the present invention, the primary target is a protein such as a receptor. Alternatively, the primary target may be a metabolic pathway, which is upregulated during a disease, e.g. infection or cancer, such as DNA synthesis, protein synthesis, membrane synthesis and carbohydrate uptake. In diseased tissues, above-mentioned markers can differ from healthy tissue and offer unique possibilities for early detection, specific diagnosis and therapy, especially targeted therapy.

Effector Probe

An Effector Probe comprises an Effector Moiety that is capable of providing the desired diagnostic, imaging, and/or therapeutic effect. The Effector Probe further comprises a secondary targeting moiety.

The secondary targeting moiety relates to the part of the Effector Probe that forms the reaction partner for the available secondary target, i.e. the Bio-orthogonal Reactive Group (or groups) comprised in the Pre-targeting Probe. E.g., if the secondary target is a dienophile of formula (1), the secondary targeting moiety will be a diene such as a tetrazine, and vice versa.

The Effector Moiety can, e.g., be a detectable label. A "detectable label" as used herein relates to the part of the Effector Probe which allows detection of the probe, e.g. when present in a cell, tissue or organism. One type of detectable label envisaged within the context of the present invention is a contrast providing agent. Different types of detectable labels are envisaged within the context of the present invention and are described hereinbelow.

Thus, according to a particular embodiment of the present invention, the pretargeting kits and methods of the present invention are used in imaging, especially medical imaging. In order to identify the primary target, use is made, as the Effector Probe, of an imaging probe comprising one or more detectable labels. Particular examples of detectable labels of the imaging probe are contrast-providing moieties used in traditional imaging systems such as MRI-imageable constructs, spin labels, optical labels, ultrasound-responsive constructs, X-ray-responsive moieties, radionuclides, (bio) luminescent and FRET-type dyes. Exemplary detectable labels envisaged within the context of the present invention include, and are not necessarily limited to, fluorescent molecules, e.g. autofluorescent molecules, molecules that fluoresce upon contact with a reagent, etc., radioactive labels; biotin, e.g., to be detected through binding of biotin by avidin; fluorescent tags, imaging constructs for MRI comprising paramagnetic metal, imaging reagents, e.g., those described in U.S. Pat. Nos. 4,741,900 and 5,326,856) and the like. The radionuclide used for imaging can be, for example, an isotope selected from the group consisting of $^{3}H$, $^{11}C$, $^{13}N$, $^{15}O$, $^{18}F$, $^{19}F$, $^{51}Cr$, $^{52}Fe$, $^{52}Mn$, $^{55}Co$, $^{60}Cu$, $^{61}Cu$, $^{62}Zn$, $^{62}Cu$, $^{63}Zn$, $^{64}Cu$, $^{66}Ga$, $^{67}Ga$, $^{68}Ga$, $^{70}As$, $^{71}As$, $^{72}As$, $^{74}As$, $^{75}Se$, $^{75}Br$, $^{76}Br$, $^{77}Br$, $^{80}Br$, $^{82}Br$, $^{82}Rb$, $^{86}Y$, $^{88}Y$, $^{89}Zr$, $^{89}Zr$, $^{97}Ru$, $^{99m}Tc$, $^{110}In$, $^{111}In$, $^{113}In$, $^{114}In$, $^{117}Se$, $^{120}I$, $^{122}Xe$, $^{123}I$, $^{124}I$, $^{125}I$, $^{166}Ho$, $^{167}Tm$, $^{169}Yb$, $^{193}Pt$, $^{195}Pt$, $^{201}Tl$, and $^{203}Pb$.

Other elements and isotopes, such as being used for therapy may also be applied for imaging in certain applications.

The MRI-imageable moiety can be, for example, a paramagnetic ion or a superparamagnetic particle. The paramagnetic ion can be an element selected from the group consisting of Gd, Fe, Mn, Cr, Co, Ni, Cu, Pr, Nd, Yb, Tb, Dy, Ho, Er, Sm, Eu, Ti, Pa, La, Sc, V, Mo, Ru, Ce, Dy, Tl. The ultrasound responsive moiety can comprise a microbubble, the shell of which consisting of a phospholipid, and/or (biodegradable) polymer, and/or human serum albumin. The microbubble can be filled with fluorinated gasses or liquids.

The X-ray-responsive moieties include but are not limited to iodine, barium, barium sulfate, gastrografin or can comprise a vesicle, liposome or polymer capsule filled with iodine compounds and/or barium sulfate.

Moreover, detectable labels envisaged within the context of the present invention also include peptides or polypeptides that can be detected by antibody binding, e.g., by binding of a detectable labeled antibody or by detection of bound antibody through a sandwich-type assay. In one embodiment the detectable labels are small size organic PET and SPECT labels, such as $^{18}F$, $^{11}C$ or $^{123}I$. Due to their small size, organic PET or SPECT labels are ideally suited for monitoring intracellular events as they do not greatly affect the properties of the targeting device in general and its membrane transport in particular. An imaging probe comprising a PET label and either of the retro Diels-Alder active moieties as a secondary targeting moiety is lipophilic and able to passively diffuse in and out of cells until it finds its binding partner. Moreover, both components do not preclude crossing of the blood brain barrier and thus allow imaging of regions in the brain.

When the Effector Probe is intended to comprise a detectable label based on a metal, such as a lanthanide (e.g. Gd) for MRI contrast enhancement, such is preferably provided in the form of a chelate. In such a case the Effector Probe preferably comprises a structural moiety capable of forming a coordination complex with such a metal. A good example hereof are macrocyclic lanthanide(III) chelates derived from 1,4,7,10-tetraazacyclododecane-1,4,7,10-tetraacetic acid ($H_4$ dota), and 1,4,7,10-tetraazacyclododecane-α,α',α,''α'''-tetramethyl-1,4,7,10-tetraacetic acid ($H_4$ dotma).

The Effector Moiety can also be a therapeutic moiety such as a pharmaceutically active compound. Examples of pharmaceutically active compounds are provided herein. A therapeutic probe can optionally also comprise a detectable label.

Thus, according to another embodiment, the pretargeting kits and methods of the invention are used for targeted therapy. This is achieved by making use of an Effector Probe comprising a secondary targeting moiety and one or more pharmaceutically active agents (i.e. a drug, a toxin or a radioactive isotope for radiation therapy). Suitable drugs for use in the context of targeted drug delivery are known in the art. Optionally, the therapeutic probe can also comprise a detectable label, such as one or more imaging agents. A radionuclide used for therapy can be, for example, an isotope selected from the group consisting of $^{24}Na$, $^{32}P$, $^{33}P$, $^{47}Sc$, $^{59}Fe$, $^{67}Cu$, $^{76}As$, $^{77}As$, $^{80}Br$, $^{82}Br$, $^{89}Sr$, $^{90}Nb$, $^{90}Y$, $^{103}Ru$, $^{105}Rh$, $^{109}Pd$, $^{111}Ag$, $^{111}In$, $^{121}Sn$, $^{127}Te$, $^{131}I$, $^{140}La$, $^{141}Ce$, $^{142}Pr$, $^{143}Pr$, $^{144}Pr$, $^{149}Pm$, $^{149}Tb$, $^{151}Pm$, $^{153}Sm$, $^{159}Gd$, $^{161}Tb$, $^{165}Dy$, $^{166}Dy$, $^{166}Ho$, $^{169}Er$, $^{172}Tm$, $^{175}Yb$, $^{177}Lu$, $^{186}Re$, $^{188}Re$, $^{198}Au$, $^{199}Au$, $^{211}At$, $^{211}Bi$, $^{212}Bi$, $^{212}Pb$, $^{213}Bi$, $^{214}Bi$, $^{223}Ra$, and $^{225}Ac$.

Alternatively the drug in the therapeutic probe is selected from sensitizers for photodynamic therapy.

Alternatively the therapeutic probe comprises a recognition moiety that binds to therapeutic entities in vivo, such as T cells, natural killer cells, or other endogenous constructs such as proteins.

In the Effector Probe, the secondary targeting moiety, i.e. the second Bio-orthogonal Reactive Group and the effector moiety can be directly linked to each other. They can also be bound to each other via a linker, and furthermore they can both be linked to a secondary targeting scaffold. The linker can, independently, be selected from the same moieties, e.g. poly ethylene glycols, as discussed above. The secondary targeting scaffold can be e.g. a biopolymer such as a polypeptide.

The invention also relates to a pre-targeting method, using the retro Diels-Alder reaction for both the secondary targeting and clearance of circulating Pre-Targeting Probe. Herein a Pre-targeting Probe comprising a primary targeting moiety (e.g., an antibody, and antibody fragment, or a receptor binding peptide), functionalized with a suitable diene, preferably a compound according to any one of the formulae (2)-(7) mentioned above, or with a cyclooctene or cyclooctyne according to formula (1) above, respectively, is injected into a subject. After binding to the target (e.g. a primary or metastatic tumor lesion, an atherosclerotic plaque, an infracted area, an inflammation or infection site, etc.), a Clearing Agent comprising a Bio-orthogonal Reactive Group reactive towards the Bio-orthogonal Reactive Group on the Pre-targeting Probe, is administered so as to capture circulating Pre-Targeting Probe, and affect clearance from the circulation and from non-target tissues (e.g. blood, liver, spleen, kidney, etc.). Then an Effector Probe comprising a secondary targeting moiety, e.g. carrying a cyclooctene or tetrazine derivative, respectively (i.e. the reactive counterpart of the Bio-orthogonal Reactive Group present in the Pre-targeting Probe), and a drug or an imageable label, is injected. The Effector Probe binds to the primary targeting moiety and provides high contrast or selectively treats the disease site. The reactive counterpart of the Bio-orthogonal Reactive Group present in the Pre-targeting Probe can be the same or different as the reactive counterpart (for the same Bio-orthogonal Reactive Group present in the Pre-targeting Probe) comprised in the Clearing Agent.

The invention also relates to the targeting of a general metabolic pathway, which is upregulated during a disease (like infection or cancer) such as DNA, protein, and membrane synthesis and carbohydrate uptake. Suitable probes comprise diene or dienophile labeled amino acids, sugars, nucleic acids and choline, analogous to the metabolic tracers currently used in the art, [$^{11}$C]-methionine, [$^{18}$F]-fluorodeoxyglucose (FDG), deoxy-[$^{18}$F]-fluorothymidine (FLT) and [$^{11}$C]-choline. Cells with a high metabolism or proliferation have a higher uptake of these building blocks. In this method, e.g. tetrazine- or E-cyclooctene derivatives enter these or other pathways and accumulate in and/or on cells. After sufficient build-up and clearance of free probe a detectably labeled or drug-carrying (cell permeable) tetrazine probe or E-cyclooctene probe (or probes carrying other dienes/dienophiles according to the invention) is sent in to bind the accumulated E-cyclooctene, respectively tetrazine metabolite. As an advantage over normal FDG (fluorine 18 fluorodeoxyglucose)-type imaging, ample time is available to allow high build up of the targeting moiety before radioactivity is sent in, thus increasing the target to non-target ratio. Alternatively, a metabolic pathway and/or metabolite that is specific for a disease can be targeted.

The invention also relates to the pre-targeting of intracellular targets. Due to their small size, organic PET labels ($^{18}$F, $^{11}$C) are ideally suited for monitoring intracellular events as they do not greatly affect the properties of the targeting device in general and its membrane transport in particular (contrary to the large and polar radiometal-chelate construct conjugates). Although the substituted tetrazine moiety and the E-cyclooctene used in the invention are not necessarily small, they are relatively nonpolar and can be used for intracellular imaging of proteins, mRNA, signaling pathways etc. The secondary (e.g. PET labeled) substituted tetrazine moiety or E-cyclooctene probe (i.e. the Effector Probe) is capable of passively diffusing in and out of cells until it finds its binding partner or is subject to an active uptake mechanism. These properties also allow the use of retro Diels-Alder reaction for pre-targeting in the brain, as both components do not preclude crossing of the blood brain barrier.

The invention also pertains to pretargeted signal amplification and/or polyvalency installation. At least one primary targeting device is conjugated to a dendrimer, polymer, or nanoparticle containing multiple tetrazine moieties. After receptor binding, an (one or more) cyclooctene or cyclooctyne conjugated to one or more contrast moieties for nuclear imaging (e.g., a radiometal chelate, a radiohalogen, etc.) or MRI (e.g., Gd chelates) is injected. The subsequent retro Diels-Alder reaction results in a high concentration of MRI contrast agent at the target tissue. Furthermore, the polyvalency at the target site will increase the reaction kinetics with the TCO effector conjugate, affording an efficient target accumulation of for example MRI contrast agents. Naturally, the TCO can also be used in the targeting device conjugate and the tetrazine (or other diene of the invention) conjugated to the reporter.

Part of the invention is also a pretargeting method comprising administering a pretargeting agent as described above to a subject and allowing the agent to circulate in the subject's system for a period of time effective to achieve binding of the primary targeting moiety to a primary target, followed by clearing non-bound agent from the body by means of a Clearing Agent as defined above. A typical time period for this is 12 to 96 hours, particularly around 48 hours.

Further, the invention provides an imaging method comprising conducting a pretargeting method as described above, followed by the administration of an imaging probe also according to the invention, wherein the bio-orthogonal reactive groups in the pretargeting agent and in the imaging probe together form the reactive partners for the [4+2] retro Diels-Alder reaction. Similarly, the invention provides a method of targeted medical treatment in a subject, comprising conducting a pretargeting method as described above, followed by the administration of a therapeutic probe also according to the invention, wherein the bio-orthogonal reactive groups in the pretargeting agent and in the imaging probe together form the reactive partners for the [4+2] retro Diels-Alder reaction.

The invention also pertains to the aforementioned Clearing Agents for use in an imaging or therapeutic method as described above.

The invention will be illustrated with reference to the following, non-limiting Examples and the accompanying non-limiting Figures.

EXAMPLES

Materials

All reagents and solvents were obtained from commercial sources (Sigma-Aldrich, Acros, Biosolve, ABCR, Invitrogen, and Merck for reagents, Biosolve, Merck and Cambridge Isotope Laboratories for normal and deuterated solvents) and used without further purification unless stated otherwise. Polystyrene microspheres (Polybeads, 0.5 µm) were purchased from Polysciences. [$^{111}$In]Indium chloride and sodium [$^{125}$I]iodide solutions were purchased from PerkinElmer. Water was distilled and deionized (18 MΩcm) by means of a milli-Q water filtration system (Millipore). The labeling buffers were treated with Chelex-100 resin (BioRad Laboratories) overnight, then filtered through 0.22 µm and stored at 4° C. Kits for bicinchoninic acid (BCA) assay, gelcode blue protein staining solutions and Zeba desalting spin columns (7 KDa and 40 kDa MWCO, 0.5-2 mL) were purchased from Pierce Protein Research (Thermo Fisher Scientific). Tablets to prepare phosphate buffered saline (PBS) pH 7.4 were acquired from Calbiochem (Merck). Amicon Ultra-4 and Ultra-15 centrifugal filter units (30 and 50 kDa MW cut-off) were purchased from Millipore. Mouse serum and mouse serum albumin were purchased from Innovative Research. Synthesis and radio labeling of tetrazine 15 (FIG. 7) and transcyclooctene (TCO) conjugation to the mAb (CC49) were performed as described in Rossin et al., Angew Chem Int Ed 2010, 49, 3375-8.

Methods:

NMR spectra were recorded in CDCl$_3$ or [D$_6$]DMSO, using a Bruker DPX300 spectrometer or a Bruker Avance400 spectrometer. $^{13}$C NMR multiplicities (q=quaternary, t=tertiary, s=secondary and p=primary) were distinguished using a DEPT pulse sequence. Infrared spectra were measured on a Perkin Elmer 1600 FT-IR. MALDI-TOF mass spectra (positive, linear mode) of the MSA-conjugates were acquired on a Voyager-DE™ Pro (PerSeptive Biosystems, PE) using a matrix of α-cyano-4-hydroxycinnamic acid (CHCA).

Preparative column chromatography was performed on a Combiflash Companion apparatus (Teledyne Isco) using SiliCycle silica columns. Preparative HPLC was performed using an Agilent 1200 apparatus, equipped with a C18 Zorbax column (21.2×150 mm, 5 µm particles) applying a gradient of water and MeCN containing 0.1% TFA. Analytical radio-HPLC was carried out on an Agilent 1100 system equipped with a Gabi radioactive detector (Raytest). The samples were loaded on an Agilent Eclipse XDB-C18 column (4.6×150 mm, 5 μm particles), which was eluted at 1 mL/min with a linear gradient of MeCN in water containing 0.1% TFA (2 min at 10% MeCN followed by an increase to 45% MeCN in 11 min). The UV wavelength was preset at 254 nm. Size exclusion (SEC) HPLC was carried out on an Agilent 1200 system equipped with a Gabi radioactive detector. The samples were loaded on a BioSep-SEC-S 3000 column (300×7.8 mm, 5 μm particles, Phenomenex) and eluted with 0.2 M phosphate solution, pH 6.8, containing 10% MeCN at 1 mL/min. The UV wavelength was preset at 260 and 280 nm.

The $^{111}$In-tetrazine labeling yields were determined by radio-TLC, using ITLC-SG strips (Varian) eluted with 200 mM EDTA in 0.9% aq. NaCl and imaged on a phosphor imager (FLA-7000, Fujifilm). In these conditions, free $^{111}$In migrates with $R_f$=0.9, while $^{111}$In-tetrazine remains at the origin. The $^{125}$I-mAb labeling yields were also determined with radio-TLC, using ITLC-SG strips eluted with a 1:1 MeOH/ethyl acetate mixture and imaged on a phosphor imager. In these conditions, free [$^{125}$I]iodide and $^{125}$I-SHPP migrate with $R_f$=0.9, while $^{125}$I-mAbs remain at the origin.

SDS-PAGE was performed on a Phastgel system using 7.5% PAGE homogeneous gels (GE Healthcare Life Sciences). The protein MW standard solution (Precision Plus dual color standard) was purchased from BioRad. Upon electrophoresis, the gels were stained for 2 hours with gelcode blue, destained overnight in water and then digitized with a conventional flat bed scanner.

The number of tetrazine molecules conjugated to albumin and the concentration of CC49 solutions were determined with a NanoDrop 1000 spectrophotometer (Thermo Fisher Scientific) from the absorbance at 322 nm and 280 nm, respectively. The number of tetrazines per mouse serum albumin molecule was also determined by MALDI-TOF. The concentration of CC49 solutions was also determined by BCA.

The average hydrodynamic diameter of the polystyrene beads coated with albumin-tetrazine was determined by dynamic light scattering (ALV-LSE, α=90°). The absence of aggregates in the bead suspension and the number of beads injected in mice were determined with a Beckman Coulter Counter (Multisizer 3) using a 50 μm aperture tube. An aliquot of the solution was mixed with 50 ml IsotonII (Beckman Coulter) from which 100 μL was analyzed in the diameter range of 1.1 μm to 30 μm.

LS174T tumor model. The human colon cancer cell line LS174T was obtained from the ATCC and maintained in Eagle's minimal essential medium (Sigma) supplemented with 10% heat inactivated fetal calf serum (Gibco), penicillin (100 U/mL), streptomycin (100 μg/mL) and 2 mm Glutamax. Nude female Balb/C mice (20-25 g body weight, Charles River Laboratories) were inoculated subcutaneously with 5×10$^6$ cells in 100 μL sterile PBS.

Example 1

As an example to link the tetrazine derived moiety to a scaffold to obtain a clearing agent object of the invention, a molecule 5 is prepared. Molecule 5 comprises an N-hydroxysuccimidyl moiety, that is used to couple the molecule with amino groups present on the scaffold, for instance a protein.

Figure 4:
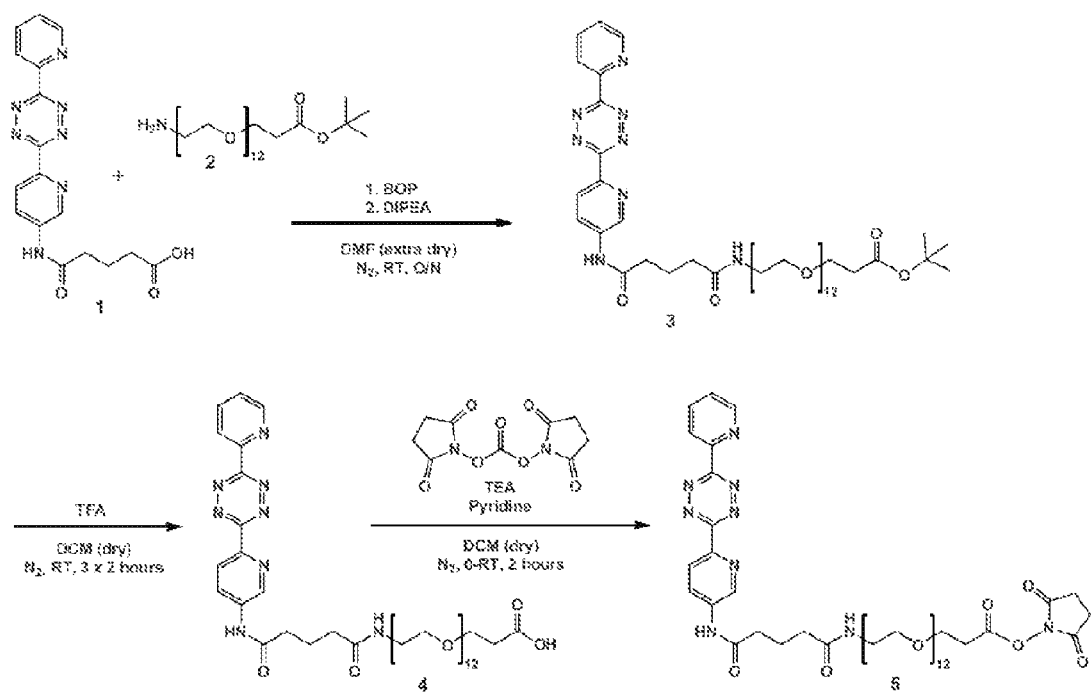
FIG. 4 to FIG. 7 illustrate the reaction schemes and chemical structures of compounds referred to in the examples.

The synthesis of 5 is outlined in FIG. 4, starting from 5-oxo-5-(6-(6-(pyridin-2-yl)-1,2,4,5-tetrazin-3-yl)pyridin-3-ylamino)pentanoic acid (1), which is made according to Rossin et al. Angewandte Chemie International Edition 2010, 49(19), 3375-8.

Tert-butyl 41,45-dioxo-45-((6-(6-(pyridin-2-yl)-1,2,4,5-tetrazin-3-yl)pyridin-3-yl)amino)-4,7,10,13,16,19,22,25,28,31,34,37-dodecaoxa-40-azapentatetracontan-1-oate (3)

Tert-butyl 1-amino-3,6,9,12,15,18,21,24,27,30,33,36-dodecaoxanonatriacontan-39-oate 2 (123 mg, 0.182 mmol; IRIS Biotech GmbH) was added into a dried reaction vial and co-evaporated twice with toluene. The vial was then put under nitrogen and extra dry DMF (2 ml) was added giving a colorless solution. 1 (100 mg, 0.274 mmol) and (benzotriazol-1-yloxy)tris(dimethylamino)phosphonium hexafluorophosphate (BOP; 267 mg, 0.603 mmol) dissolved in extra dry DMF (1 mL) were added sequentially to the reaction mixture under nitrogen atmosphere giving a red suspension. Finally, DIPEA (0.5 mL, 2.74 mmol) was added dropwise to the reaction mixture and the resulting solution was stirred overnight. The reaction mixture was evaporated to dryness, dissolved DCM (2 ml), and purified by flash column chromatography on silica gel using a gradient of 1-10% MeOH in DCM. The relevant fractions were combined and evaporated in vacuo yielding 3 (167 mg, 0.164 mmol, 90%) as a dark pink solid.

$^1$H NMR (300 MHz, CDCl$_3$): δ=10.58 (s, 1H), 9.05 (d, J=2.4 Hz, 1H), 8.93 (ddd, J$_1$=0.9 Hz, J$_2$=1.7 Hz, J$_3$=4.7 Hz, 1H), 8.62 (d, J=8.8 Hz, 1H), 8.59 (d, J=8.6 Hz, 1H), 8.43 (dd, J$_1$=2.4 Hz, J$_2$=8.8 Hz, 1H), 8.15 (td, J$_1$=1.8 Hz, J$_2$=7.8 Hz, 1H), 7.93 (t, J=5.5 Hz, 1H), 7.73 (ddd, J$_1$=1.1 Hz, J$_2$=4.7 Hz, J$_3$=7.8 Hz, 1H), 3.57 (t, J=6.2 Hz, 2H), 3.53-3.47 (broad s, 46H), 3.25-3.16 (m, 2H), 3.41 (t, J=6.2 Hz, 2H), 2.44 (t, J=7.3 Hz, 2H), 2.17 (t, J=7.3 Hz, 2H), 1.85 (q, J=7.3 Hz, 2H), 1.38 (s, 9H); $^{13}$C NMR (75 MHz, CDCl$_3$): δ=172.1 (q), 171.7 (q), 170.4 (q), 163.0 (q), 162.8 (q), 150.6 (t), 150.2 (q), 143.8 (q), 141.3 (t), 138.5 (q), 137.8 (t), 126.5 (t), 126.1 (t), 124.8 (t), 124.2 (t), 79.7 (q), 69.8 (s), 69.7 (s), 69.6 (s), 69.5 (s), 69.1 (s), 66.2 (s), 38.5 (s), 35.8 (s), 35.7 (s), 34.4 (s) 27.7 (p), 20.9 (s).

41,45-dioxo-45-((6-(6-(pyridin-2-yl)-1,2,4,5-tetrazin-3-yl)pyridin-3-yl)amino)-4,7,10,13,16,19,22,25,28,31,34,37-dodecaoxa-40-azapentatetracontan-1-oic acid (4)

To a stirred solution of 3 (160 mg, 0.157 mmol) in anhydrous DCM (2 mL) under nitrogen atmosphere was added TFA (2 mL). The reaction mixture was stirred for 2 hours at room temperature and evaporated to dryness. The residue was redissolved in dry DCM (2 ml) and again treated with TFA (2 mL) for 2 hours. This process was repeated once more. Finally, the reaction mixture was evaporated to dryness and co-evaporated twice with DCM furnishing the deprotected product 4 in quantitative yield.

$^1$H NMR (300 MHz, CDCl$_3$): δ=10.57 (s, 1H), 9.05 (broad s, 1H), 8.94 (broad s, 1H), 8.63 (d, J=8.4 Hz, 1H), 8.60 (d, J=7.2 Hz, 1H), 8.43 (dd, J$_1$=2.4 Hz, J$_2$=8.8 Hz, 1H), 8.16 (td, J$_1$=1.7 Hz, J$_2$=7.8 Hz, 1H), 7.93 (t, J=5.5 Hz, 1H), 7.74 (dd, J$_1$=4.7 Hz, J$_3$=6.8 Hz, 1H), 3.58 (t, J=6.4 Hz, 2H), 3.53-3.46 (broad s, 46H), 3.41 (t, J=6.0 Hz, 2H), 3.25-3.17 (m, 2H), 2.44 (t, J=7.3 Hz, 2H), 2.17 (t, J=7.3 Hz, 2H), 1.85 (q, J=7.3 Hz, 2H).

2,5-Dioxopyrrolidin-1-yl 41,45-dioxo-45-((6-(6-(pyridin-2-yl)-1,2,4,5-tetrazin-3-yl)pyridin-3-yl)amino)-4,7,10,13,16,19,22,25,28,31,34,37-dodecaoxa-40-azapentatetracontan-1-oate (5)

To a stirred solution of 4 (150 mg, 0.155 mmol) in anhydrous DCM (3 ml) under $N_2$-atmosphere at 0° C. were sequentially added di-(N-succinimidyl) carbonate (47.8 mg, 0.187 mmol), pyridine (15 µL), and triethylamine (0.25 mL). The mixture was stirred for 2 hours while warming up to room temperature, then evaporated to dryness, redissolved in DCM (20 ml), and washed with $H_2O$ (3×10 mL). The organic layer was dried over $MgSO_4$, filtered and evaporated in vacuo yielding 5 (94 mg, 0.089 mmol, 57%) as a dark pink solid.

$^1$H NMR (300 MHz, $CDCl_3$): δ=9.67 (s, 1H), 9.01-8.97 (m, 2H), 8.77-8.71 (m, 2H), 8.64 (dd, $J_1$=2.4 Hz, $J_2$=8.8 Hz, 1H), 8.02 (td, $J_1$=1.7 Hz, $J_2$=7.7 Hz, 1H), 7.58 (ddd, $J_1$=1.1 Hz, $J_2$=4.7 Hz, $J_3$=7.5 Hz, 1H), 6.60 (t, J=5.4 Hz, 1H), 3.84 (t, J=6.4 Hz, 2H), 3.70-3.55 (broad s, 46H), 3.52-3.43 (m, 2H), 2.90 (t, J=6.5 Hz, 2H), 2.85 (s, 4H), 2.58 (t, J=6.8 Hz, 2H), 2.37 (t, J=6.8 Hz, 2H), 2.09 (q, J=6.8 Hz, 2H); $^{13}$C NMR (75 MHz, $CDCl_3$): δ=172.9 (q), 172.5 (q), 168.9 (q), 166.7 (q), 163.6 (q), 163.4 (q), 151.0 (t), 150.3 (q), 144.0 (q), 142.0 (t), 138.6 (q), 137.4 (t), 126.5 (t), 126.4 (t), 125.1 (t), 124.3 (t), 70.7 (s), 70.5 (s), 70.2 (s), 69.6 (s), 65.7 (s) 39.3 (s), 35.9 (s), 35.0 (s), 32.1 (s) 25.6 (s), 21.3 (s).

Example 2

Figure 3:
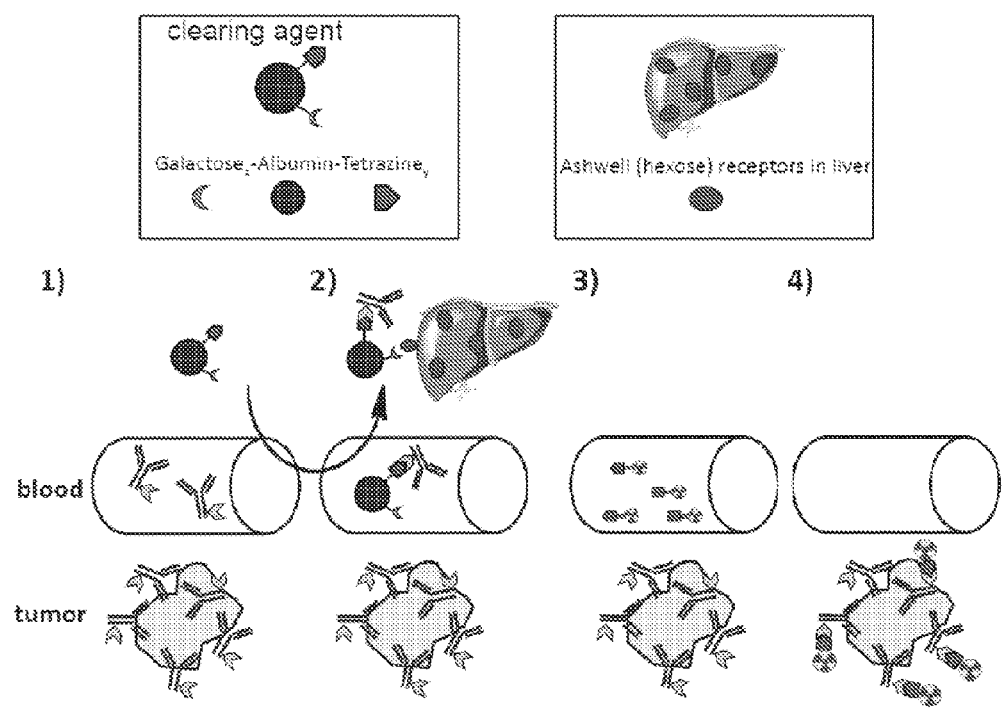
FIG. 3 depicts a general scheme of a pretargeting concept where in 1) a monoclonal antibody (mAb)-tag (e.g., a transcyclooctene) distributes in the circulation and accumulates in tumor, then in 2) the circulating mAb-tag reacts via a retro-DA reaction with a clearing agent comprising a scaffold bearing galactose moieties and the complementary tag (e.g. a tetrazine) and is captured by the liver via the Ashwell receptors, then in 3) the radioactive pretargeting effector carrying the complementary tag (e.g., a tetrazine) is injected and in 4) the effector reacts via a retro-DA reaction with the mAb-tag in the tumor or clears rapidly from the circulation.

As an example of a clearing agent outlined in FIG. 3, compound 12 (see FIG. 5) is prepared. Compound 12 comprises a proteic scaffold (mouse serum albumin; MSA) functionalized with 9-10 tetrazine molecules for reaction with the reactive partner, in this case a cyclooctene derivative, on the pre-targeting probe via the retro-DA reaction, and with 16-18 galactose molecules for interaction with the Ashwell receptors in the liver.

The clearing agent was prepared by 2-step sequential covalent modification of MSA, first with galactoses, then with tetrazines. Galactose modification was achieved using the amine-reactive 2-imino-2-methoxyethyl-1-thio-β-D-galactopyranoside (9), which conjugates to lysines on albumin. This agent may be prepared on a µmolar-scale from the commercially available compound cyanomethyl 2,3,4,6-tetra-O-acetyl-1-thio-β-D-galactopyranoside (8) directly before albumin-conjugation, performed following the teachings of US20030129191 (procedure 1). We improved on this in procedure 2: the amine-reactive coupling agent 2-imino-2-methoxyethyl-1-thio-β-D-galactopyranoside (9) itself can be isolated in high purity according to the optimized procedures described below, and then coupled to albumin in a single step.

Figure 5:
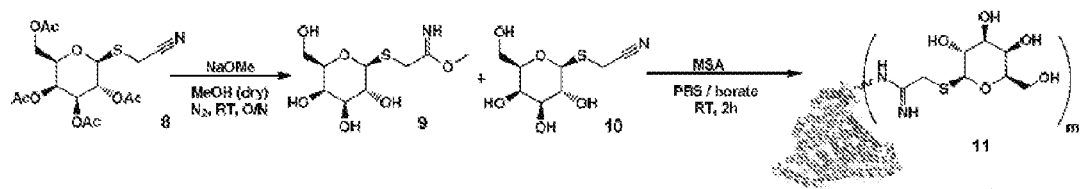
Figure 5:
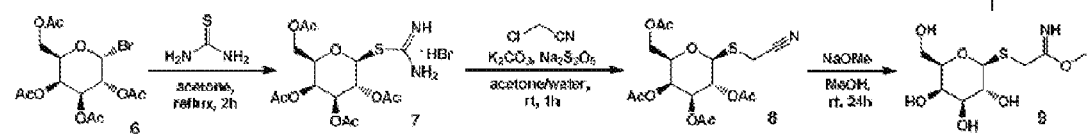
Figure 5:
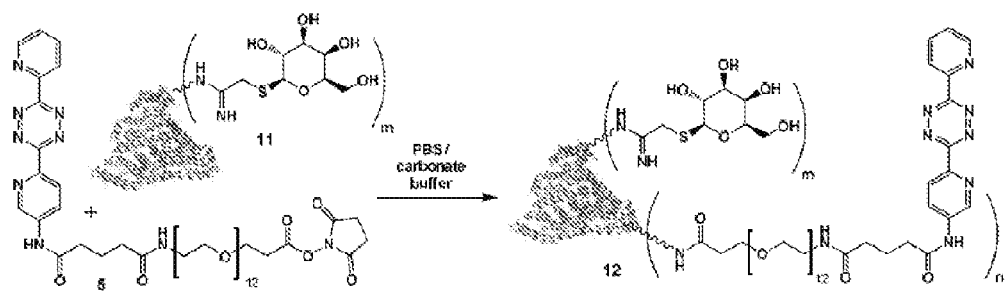

Synthesis of galactose-MSA (11, Procedure 1, FIG. 5)

To a 0.1 M solution of cyanomethyl 2,3,4,6-tetra-O-acetyl-1-thio-β-D-galactopyranoside (8) in anhydrous MeOH was added 1/10th of the volume of a 0.1M solution of NaOMe in anhydrous MeOH, and the mixture was allowed to react overnight (shaking at 1,000 rpm). The ratio of the products (compound 9 to compound 10) was determined by $^1$H-NMR (see spectral data below), and was typically between 0.7 and 1.

The required volume of the crude reaction mixture (containing about 33 molar equivalents of compound 9 relative to the desired quantity of MSA to be functionalized) was lyophilized in an eppendorf vial, and MSA (3.5 mg, 0.0530 µmol) dissolved in a 10:1 mixture (200 µL) of PBS pH 7.4/0.5M borate buffer pH 8.5 was added. The reaction mixture was shaken (1000 rpm) at room temperature for 2 hours, then stored overnight at 4° C. The reaction mixture was desalted using a Zeba desalting spin cartridge (7 kDa MWCO, Pierce), which was previously equilibrated with water. The galactose modification grade was subsequently determined by MALDI-TOF analysis (typically about 15-19 galactoses/MSA, compound 11).

Synthesis of galactose-MSA (11, Procedure 2, FIG. 5)

The galactose coupling agent 2-imino-2-methoxyethyl-1-thio-β-D-galactopyranoside (9) was prepared starting from 2,3,4,6-tetra-O-acetyl-α-D-galactopyranosyl bromide (6) in 3 steps via the intermediates 2-S-(2,3,4,6-tetra-O-acetyl-β-D-galactopyranosyl)-2-thiouronium bromide (7) and cyanomethyl 2,3,4,6-tetra-O-acetyl-1-thio-β-D-galactopyranoside (8) as shown in FIG. 5.

2-S-(2,3,4,6-tetra-O-acetyl-β-D-galactopyranosyl)-2-thiouronium bromide (7): 2,3,4,6-tetra-O-acetyl-α-D-galactopyranosyl bromide (6; 15.00 g, 36.48 mmol) and thiourea (3.05 g, 40.07 mmol) were dissolved in acetone (75 mL). The solution was heated to reflux for 2 hours, and subsequently filtered and cooled to 20° C. Addition of pentane (75 mL) resulted in the precipitation of the product as a white, crystalline solid (16.11 g, 91%). $^1$H-NMR (400 MHz, [$D_6$]DMSO,): δ=1.95 (s, 3H, $CH_3$), 2.01 (s, 3H, $CH_3$), 2.08 (s, 3H, $CH_3$), 2.14 (s, 3H, $CH_3$), 4.09 (m, 2H, $H_6$, $H_{6'}$), 4.45 (t, J=6.4 Hz, 1H, $H_5$), 5.11 (t, $J_{2,3}$=10 Hz, 1H, $H_2$), 5.22 (dd, $J_{2,3}$=9.9 Hz, $J_{3,4}$=3.2 Hz, 1H, $H_3$), 5.39 (d, J=3.2 Hz, 1H, $H_4$), 5.71 (d, $J_{1,2}$=10 Hz, 1H, $H_1$), 9.11 (br, 2H, $NH_2$), 9.35 (br, 2H, $NH_2$).

Cyanomethyl 2,3,4,6-tetra-O-acetyl-1-thio-β-D-galactopyranoside (8): 2-S-(2,3,4,6-Tetra-O-acetyl-β-D-galactopyranosyl)-2-thiouronium bromide (7; 16.11 g, 31.07 mmol), sodium metabisulphite (11.81 g, 62.14 mmol), potassium carbonate (4.72 g, 34.18 mmol), and chloroacetonitrile (8.21 g, 108.7 mmol) were dissolved in acetone/water (50:50 v/v, 200 mL), and stirred for 1 hour at room temperature. The reaction mixture was poured in ice-water (300 mL), and stirred for an additional 2 hours. The white precipitate was collected by filtration and recrystallized from hot methanol (30 mL). The product was filtered off as a white crystalline solid (9.61 g, 77%). M.p.=97° C. (Lit: 95-97° C.). $^1$H-NMR (400 MHz, $CDCl_3$): δ=2.00 (s, 3H, $CH_3$), 2.07 (s, 3H, $CH_3$), 2.09 (s, 3H, $CH_3$), 2.17 (s, 3H, $CH_3$), 3.35 (d, J=17 Hz, 1H, S—CH), 3.64 (d, J=17 Hz, 1H, S—CH'), 4.01 (t, J=6.9 Hz, 1H, $H_5$), 4.16 (m, 2H, $H_6$, $H_{6'}$), 4.7 (d, $J_{1,2}$=10 Hz, 1H, $H_1$), 5.11 (dd, $J_{3,4}$=3.2 Hz, $J_{2,3}$=10 Hz, 1H, $H_3$), 5.24 (t, J=10 Hz, 1H, $H_2$), 5.47 (d, J=2.4 Hz, 1H, $H_4$). FT-IR (ATR): ν=2249 (CN, w), 1739 (C=O, s).

2-Imino-2-methoxyethyl-1-thio-β-D-galactopyranoside (9): Cyanomethyl 2,3,4,6-tetra-O-acetyl-1-thio-β-D-galactopyranoside (8; 2.02 g, 5.00 mmol) was dissolved in anhydrous MeOH (50 mL) and a methanolic solution of sodium methoxide (25 w %, 115 µL, 0.50 mmol) was added. The reaction mixture was stirred at room temperature for 24 hours, and subsequently concentrated to a volume of 15 mL. The product was allowed to crystallize at room temperature and then at −18° C. Filtration and drying gave white crystals (1.11 g; 83%). M.p.=129° C. $^1$H-NMR (400 MHz, $CD_3OD$): δ=3.44 (dd, $J_{2,3}$=10 Hz, $J_{3,4}$=4.2 Hz, 1H, $H_3$), 3.52 (dd, $J_{2,3}$=10 Hz, $J_{1,2}$=9.0 Hz, 1H, $H_2$), 3.54 (m, 1H, $H_5$), 3.73

(—OCH$_3$), 3.78 (m, 2H, H$_6$, H$_{6'}$), 3.87 (dd, J$_{3,4}$=4.0 Hz, J$_{4,5}$=1.5 Hz, 1H, H$_4$), 4.27 (d, J$_{1,2}$=9.6 Hz, 1H, H$_1$). FT-IR (ATR): ν=3287 (N—H, s), 1650 (C═NH, s).

MSA-coupling: To a solution of MSA (20 mg, 0.303 μmol) dissolved in a 10:1 mixture of PBS pH 7.4/0.5M borate buffer pH 8.5 (900 μL) was added a freshly-prepared 18.2 mg/ml stock solution of 2-imino-2-methoxyethyl-1-thio-13-D-galactopyranoside (9) in the same buffer system (200 μL), resulting in a 45-fold molar excess of galactose coupling agent (9) relative to MSA. The reaction mixture was shaken (1000 rpm) at room temperature for 2 hours, then desalted using a Zeba desalting spin cartridge (7 kDa MWCO, Pierce), which was previously equilibrated with water. After lyophilization, galactose-MSA (compound 11) was obtained as a white fluffy solid (15.3 mg, 72%). The galactose modification grade was subsequently determined by MALDI-TOF analysis MSA: MH$^+$=65941. Galactose-MSA: MH$^+$=69823, which corresponds to a mean of 16.4 galactoses/MSA (mass of added galactose fragment is 236 Da). Variation among different batches is about 16-18 galactoses/MSA). The stability of a 10 mg/ml solution of galactose-MSA in water at 4° C. was assessed by repeated MALDI-TOF analysis every 2 weeks for a total of 5 months. The conjugate proved to be stable.

Synthesis of galactose-MSA-tetrazine (12)

A solution of galactose-functionalized mouse serum albumin (11, galactose-MSA, 1 mg) in PBS was mixed with a 10 mg/mL solution of tetrazine-NHS (5) in DMF (30 μL, 20 equiv. with respect to galactose-MSA) and 1M carbonate buffer pH 9.6 (7.5 μL) was added. The solution (250 μL total) was incubated at 37° C. for 30 min and then transferred into an Ultra-15 centrifugal filter unit (30 kDa MW cut-off). Product 12 was extensively washed with water then freeze-dried overnight to yield a pink fluffy powder. The tetrazine modification grade was determined by MALDI-TOF analysis. Galactose-MSA-tetrazine: MH$^+$=79010, which corresponds to a mean of 9.7 tetrazines/galactose (16.4)-MSA (mass of added tetrazine fragment is 948 Da; MH$^+$ (galactose (16.4)-MSA)=69823). UV-V is measurements on nanodrop confirmed the presence of 9-10 tetrazines per molecule (measured value: 8.9 tetrazines/galactose (16.4)-MSA Example 3

Figure 6:
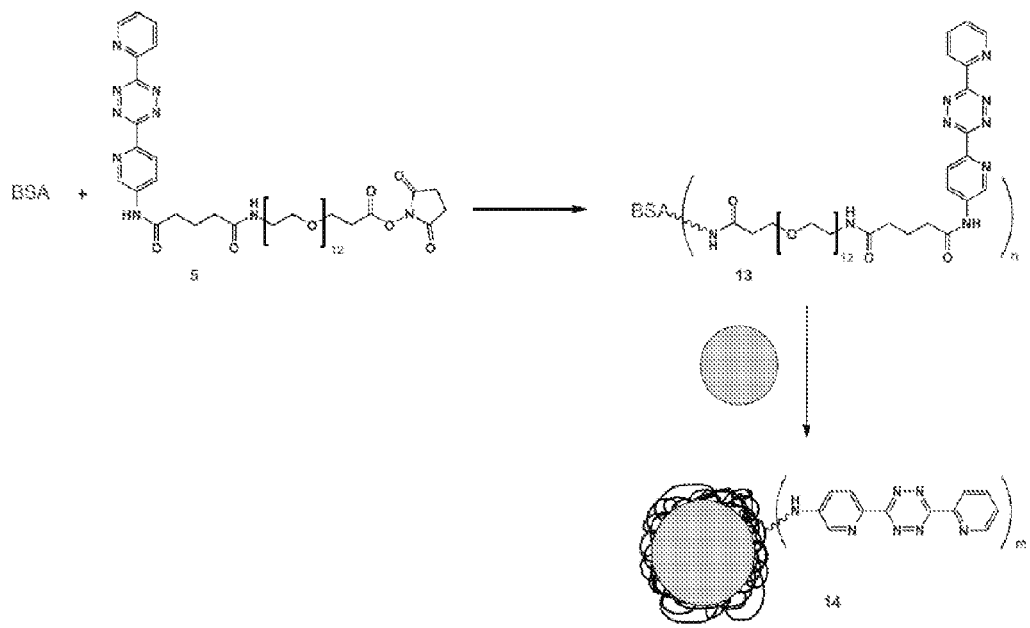

Compound 14 is prepared as an example of a clearing agent which reacts with a pre-targeting probe in blood via the retro-DA reaction and carries it to an excretory organ, for example the liver, because of physicochemical properties such as size. Compound 14 comprises a polystyrene bead coated with a tetrazine functionalized protein and was prepared as outlined in FIG. 6.

A solution of bovine serum albumin (BSA, 1.5 mg) in phosphate buffered saline (PBS) was mixed with a 10 mg/mL solution of tetrazine-NHS (5) in DMF (63 μL, 26 equiv. with respect to BSA) and 1M carbonate buffer pH 9.6 (7.5 μL) was added. The solution (250 μL total) was incubated at 37° C. for 30 min then the low MW components were removed from the solution by using a Zeba desalting spin cartridge (7 kDa MWCO, Pierce) pre-washed with PBS. The eluate containing BSA-tetrazine (13) in PBS was added to 750 μL suspension of polystyrene beads in H$_2$O (Polybead, 0.5 μm, Polyscience) and the resulting suspension was incubated at room temperature on an end-over-end rotating mixer (10 rpm). After incubation, the suspension of beads coated with BSA-tetrazine (14) was centrifuged at 12,000 rpm for 4 min. The supernatant was carefully removed and the pellet was resuspended in 1 mL 0.3% BSA in PBS (w/v) by using a tip sonicator at low power (Sonics VibraCell, 4×5 sec pulses, 40% of power). The centrifuging-resuspension cycle was repeated 3 times then the bead pellet was resuspended in 750 μL 0.3% BSA in PBS. The absence of macroaggregates in the beads suspension was confirmed by Coulter Counter measurement (99% of particles were smaller than 2.7 μm) and a 506 nm bead diameter (number weighed) was measured by dynamic light scattering.

Example 4

Tetrazine Radiolabeling

Figure 7:
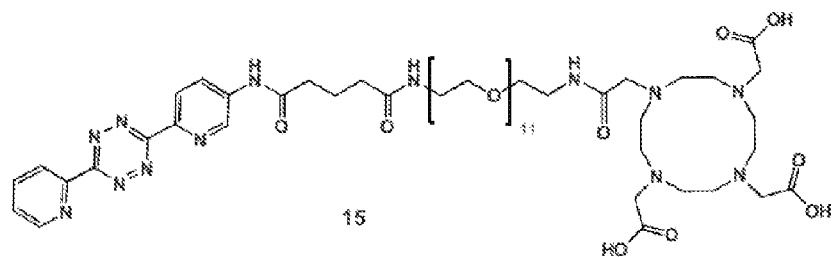

The DOTA-conjugated tetrazine (15; FIG. 7, described in Rossin et al. Angew Chem Int Ed 2010, 49, 3375-8) was dissolved (1 mg/mL) in 0.2M ammonium acetate pH 7.0 and stored at −80° C. before use. An aliquot of 15 was combined with a suitable amount of [$^{111}$In]indium chloride and incubated for 10 min at 37° C. under gentle agitation. Then, 5 μL 10 mM DTPA was added and the solution was incubated for an additional 5 min. Typically, a quantitative labeling yield and a radiochemical purity greater than 98% were obtained with this method.

mAb Radiolabeling:

To an adequate amount of sodium [$^{125}$I]iodide (5-15 MBq) in 50 μL PBS were added 1 μL of a 1 mg/mL solution of Bolton-Hunter reagent (N-succinimidyl-3-[4-hydroxyphenyl]propionate (SHPP); Pierce) in DMSO and 25 μL of a 4 mg/mL solution of chloramine-T (N-chloro 4-methylbenzenesulfonamide, sodium salt) in PBS. The resulting solution was mixed for 10-20 sec, 5 μL DMF and 100 μL toluene were added to the vial and $^{125}$I-SHPP was extracted in the organic phase, which was then transferred into a glass vial. The toluene was blown down under a gentle stream of N$_2$ after which the CC49-TCO solution (0.1-0.5 mg in 50-250 μL PBS, described in Rossin et al. Angew Chem Int Ed 2010, 49, 3375-8) was added, the pH was adjusted to 9 with 1M carbonate buffer and the reaction mixture was incubated at RT for 30 min under gentle shaking. After incubation, the labeling yield was determined by radio-ITLC. The crude reaction mixture was then loaded onto a Zeba spin desalting column (40 kDa MWCO, Pierce), which was pre-equilibrated with saline solution. The reaction vial was rinsed with 20 μL saline solution and the rinse was loaded onto the column as well. After Zeba purification, the radiochemical purity of the $^{125}$I-CC49-TCO solution was determined by radio-ITLC, radio-HPLC and SDS-PAGE; the protein concentration was determined with a BCA assay.

Figure 8:
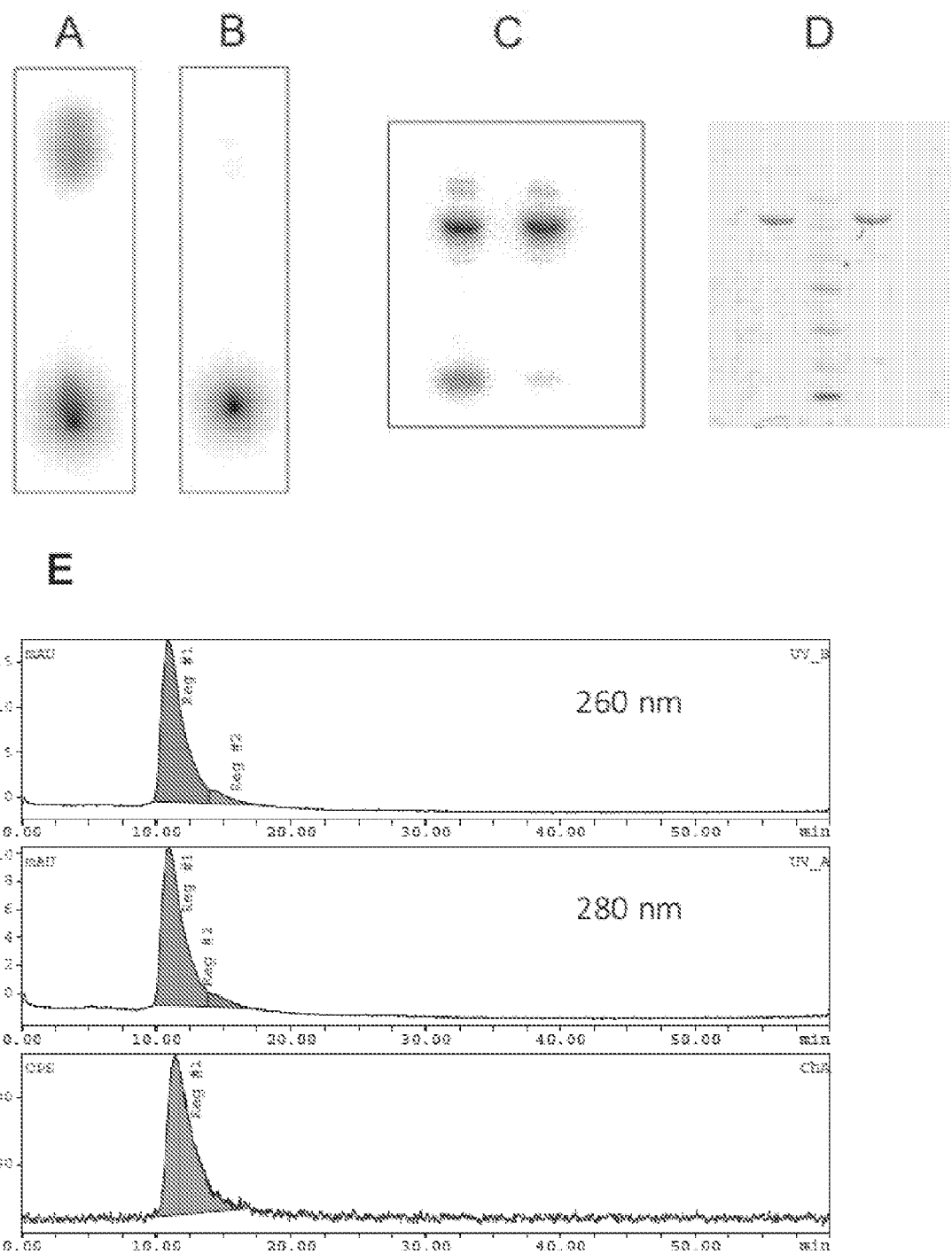
FIG. 8 depicts the radio-ITLC of (A) crude and (B) purified $^{125}$I-CC49-TCO, (C) the radioactive and (D) the protein stained SDS-PAGE of crude and purified $^{125}$I-CC49-TCO and (E) the radioactive and UV SEC-HPLC profiles (260 nm and 280 nm) of purified $^{125}$I-CC49-TCO.

Typically, greater than 70% $^{125}$I-SHPP mAb conjugation and a >98% radiochemical purity for the purified $^{125}$I-CC49-TCO species were obtained with this procedure (FIG. 8).

Example 5

As an example of how to use the clearing agent object of this invention, the blood kinetics of $^{125}$I-CC49-TCO with and without injection of clearing agents 12 and 14 are presented.

Figure 9:
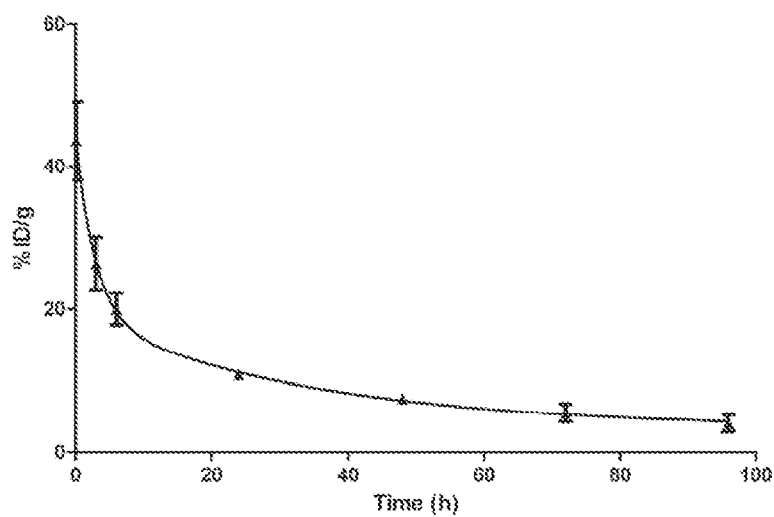
FIG. 9 depicts the blood profile for $^{125}$I-CC49-TCO in normal mice from example 5. Datapoints are the mean % ID/g; error bars represent one standard deviation (n=3).

Three nude female mice (20-25 g) were injected with $^{125}$I-labeled CC49-TCO (ca 9 TCOs/mAb; 100 μg/100 μL per mouse, t=0) intravenously and blood samples were withdrawn from the vena saphena after 5 min, 3 hours, 6 hours, 1 day, 2 days and 3 days. At 4 days after injection, the mice were sacrificed and blood was withdrawn by heart puncture. The blood samples were weighed, diluted with 1 mL PBS and the radioactivity was counted in a gamma counter along with standards to determine the % injected dose per gram (% ID/g) of blood. The results of this experiment are depicted in FIG. 9. The blood data were fitted to a bi-exponential decay (GraphPad Prism v 4.1, $R^2=0.972$) with a 1.97 hours half-life in the alpha-phase and a 23.5 hours half-life in the beta-phase.

Figure 10:
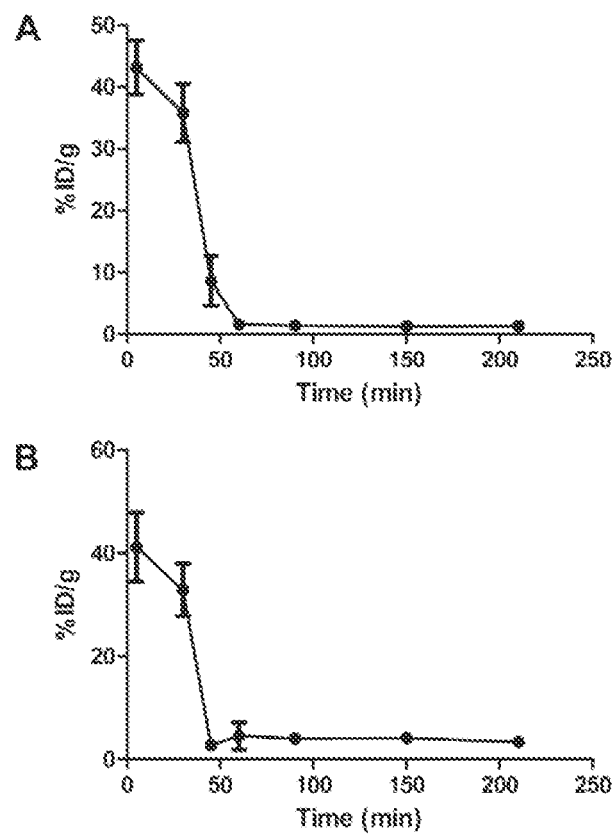
FIG. 10 depicts the blood profiles for $^{125}$I-CC49-TCO in normal mice, before and after administration of (A) galactose-MSA-tetrazine (12) and (B) polystyrene beads coated with BSA-tetrazine (14), from example 5. Datapoints represent the mean % ID/g; error bars represent one standard deviation (n=3).
Figure 11:
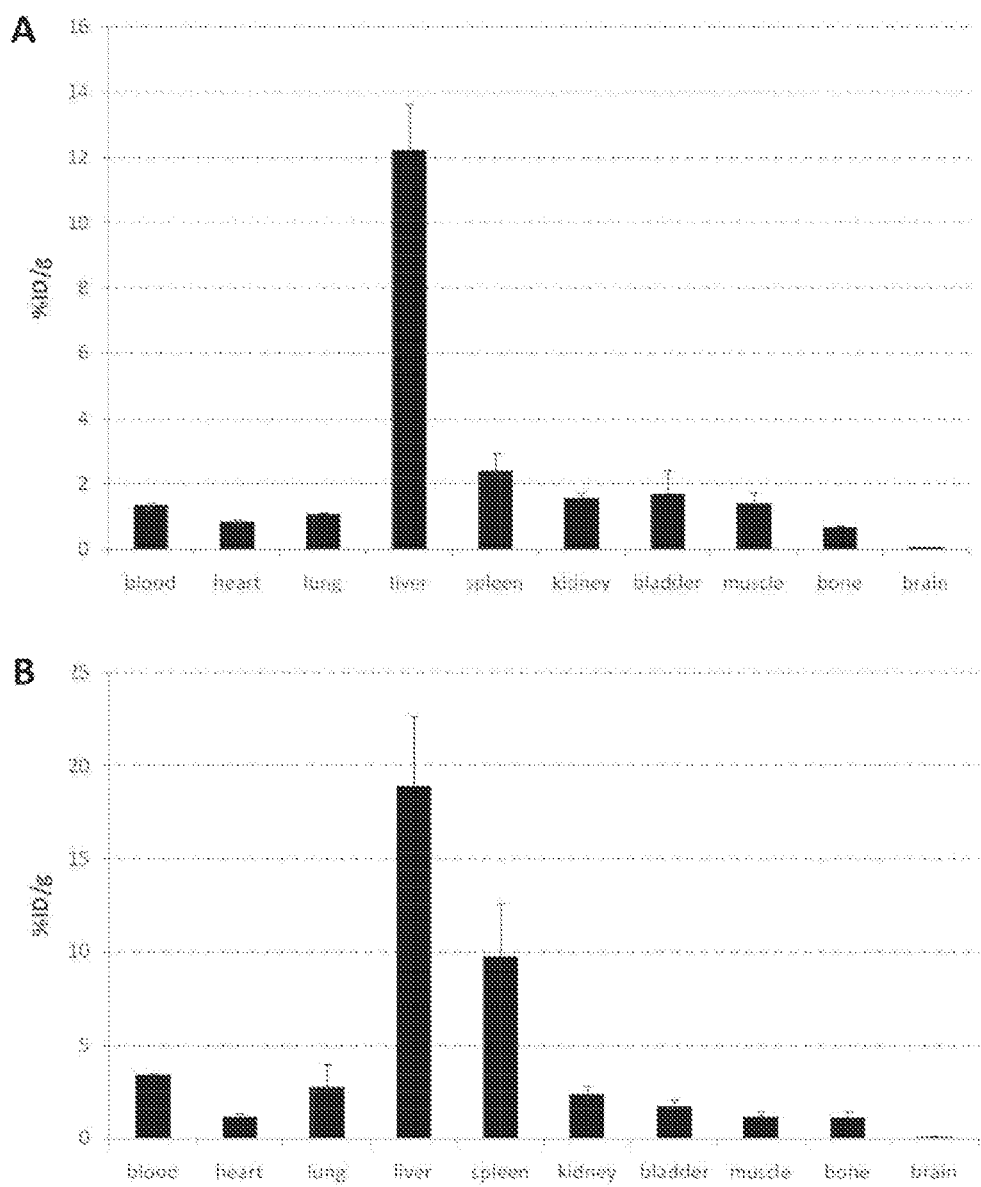
FIG. 11 depicts the biodistribution of $^{125}$I-CC49-TCO in selected organs after administration of (A) galactose-MSA-tetrazine (12) and (B) polystyrene beads coated with BSA-tetrazine (14), from example 5. Bars represent the mean % ID/g; error bars represent one standard deviation (n=3).

Three nude female mice (20-25 g) were injected with $^{125}$I-labeled CC49-TCO (20 μg/75 μL per mouse, t=0) intravenously and blood samples were withdrawn from the vena saphena after 5 min and 30 min. Then (t=35 min), each mouse received an intravenous injection of galactose-MSA-tetrazine (12, 120 μg/100 μL per mouse) or beads coated with BSA-tetrazine (14, ca. $4 \times 10^7$ beads/100 μL per mouse) and blood samples were withdrawn at 45, 60, 90, and 150 min. At 210 min after mAb injection the mice were sacrifice, blood was withdrawn by heart puncture and select organs and tissues were harvested. The blood samples and tissues (blotted dry) were weighed, added with 1 mL PBS and the radioactivity was counted in a gamma counter along with standards. The results of the two blood kinetics are shown in FIG. 10. A marked reduction of $^{125}$I-CC49-TCO levels in blood was observed immediately after clearing agent administration (35.8±4.7% ID/g 5 min before and 1.6±0.4% ID/g 25 min after 12 injection and 32.3±4.7% ID/g 5 min before and 2.7±0.4% ID/g 10 min after 14 injection). The sudden decrease in blood radioactivity levels demonstrates that a reaction happens in blood between the clearing agents and the mAb-TCO and that the resulting constructs are taken up in liver (FIG. 11) and then cleared through the intestine (22.8±4.9% and 13.0±1.8% of the mAb injected dose 175 min after injection of compound 12 and 14, respectively)

Example 6

As an example of how to use the clearing agent object of this invention, the tumor uptake and tumor-to-blood (T/B) ratios obtained when injecting the pretargeting probe ($^{125}$I-CC49-TCO) followed by the effector probe ($^{111}$In-15) with administration of different amounts of clearing agent (12) are presented.

Nude female mice (n=3-4) bearing LS174T xenografts (0.32±0.16 g) were injected $^{125}$I-CC49-TCO (t=0, 100 μg/100 μl per mouse) followed by 20-200 μg galactose-MSA-tetrazine (12) dissolved in 100 μl saline solution (t=24 hours) and $^{111}$In-labeled 15 (21.3 μg/75 μl per mouse, t=26 hours). At 29 hours post mAb injection, the mice were sacrificed, blood was withdrawn by heart puncture and selected organs and tissues were harvested and blotted dry. The blood samples and tissues were weighed, added with 1 mL PBS and the radioactivity was counted in a gamma counter along with standards to determine the % ID/g (Table 1).

TABLE 1

Tumor uptake (% ID/g) and tumor-to-blood ratio (T/B) of $^{125}$I-CC49-TCO and $^{111}$In-tetrazine in tumor bearing mice injected with different amounts of galactose-MSA-tetrazine (12) from a dual isotope experiment. Data presented as mean ± one standard deviation (n = 3-4)

| 12 dose | $^{125}$I-CC49-TCO | | $^{111}$In-tetrazine | |
|---|---|---|---|---|
| μg/mouse | Tumor (% ID/g) | T/B | Tumor (% ID/g) | T/B |
| 20 | 19.6 ± 3.8 | 6.8 ± 1.4 | 3.7 ± 0.8 | 4.5 ± 0.5 |
| 45 | 23.7 ± 7.7 | 7.0 ± 0.3 | 4.1 ± 1.3 | 4.8 ± 0.3 |
| 80 | 24.3 ± 3.1 | 14.7 ± 2.6 | 3.8 ± 1.1 | 9.2 ± 1.6 |
| 120 | 18.9 ± 4.4 | 21.5 ± 13.6 | 3.0 ± 0.8 | 11.5 ± 4.2 |
| 160 | 19.3 ± 4.8 | 37.1 ± 10.6 | 5.1 ± 1.4 | 31.6 ± 10.5 |
| 200 | 22.9 ± 4.7 | 22.6 ± 7.0 | 3.6 ± 0.9 | 19.2 ± 3.0 |

As expected, the administration of increasing amounts of compound 12 to the tumor bearing mice results in a decrease of residual $^{125}$I-CC49-TCO circulating in blood (from 2.9±0.3% ID/g with 20 μg 12 per mouse to 0.5±0.0% ID/g with 160 μg 12 per mouse). This supports the clearing mechanism comprising the retro-DA reaction between tetrazine molecules on the clearing agent and transcyclooctene molecules on the mAb and subsequent capture by Ashwell receptors on hepatocytes. This improved mAb removal from the circulation results in an approximate 5-fold increased T/B for $^{125}$I-CC49-TCO ratio going from 20 μg to 160 μg 12 injected per mouse (Table 1). Noteworthy, increasing amounts of clearing agent up to 160 μg 12 per mouse do not block the tumor uptake of $^{111}$In-tetrazine. This is most likely due to the size of compound 12, which hampers its extravasation into tumor tissues in the short time between injection and capture by the liver.

Figure 12:
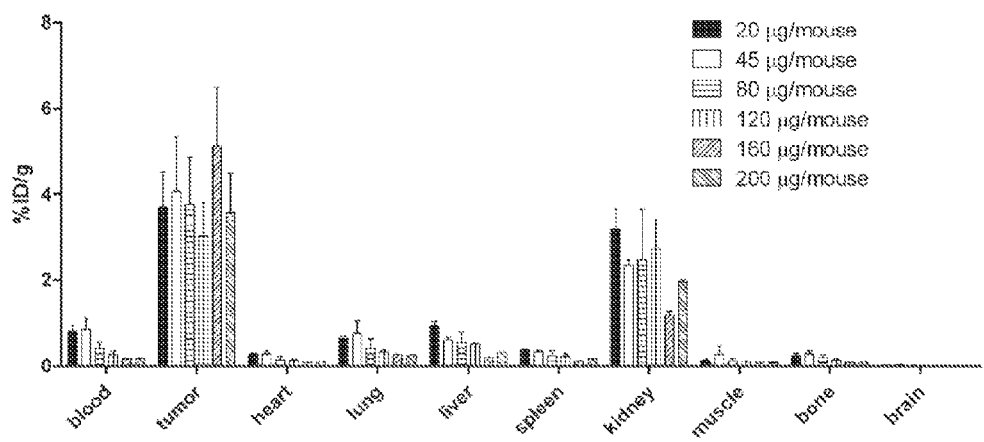
FIG. 12 depicts the biodistribution of $^{111}$In-tetrazine in tumor bearing mice that received 100 µg CC49-TCO followed by various amounts of galactose-MSA-tetrazine (12), from example 6. Bars represent the mean % ID/g; error bars represent one standard deviation (n=3-4).

The efficient removal of CC49-TCO from circulation results in a decrease of $^{111}$In-tetrazine retention in blood (hence in a higher T/B ratio) and in blood rich organs (FIG. 12). At the same time, no increase in $^{111}$In radioactivity is observed in the liver, as the mAb-clearing agent construct is internalized into hepatocytes, where it does not seem to have the opportunity to interact with the polar tetrazine.

At a clearing agent dose exceeding 160 μg per mouse, however, the liver is probably saturated and cannot process all the mAb-clearing agent adduct and the residual unreacted clearing agent. In fact, the mAb-related radioactivity circulating in blood increases (1.1±0.6% ID/g), but not due to $^{125}$I-CC49-TCO as the mAb species circulating in blood does not react with $^{111}$In-tetrazine (FIG. 12). This finding suggests that at high doses the clearing agent-mAb conjugates are less efficiently cleared. At the 200 ug clearing agent dose, the uptake of $^{111}$In-tetrazine in tumor decreases slightly despite the high amount of CC49-TCO present in this tissue. Although the difference is not significant this could be the result of tumor blocking by extravasated clearing agent. This potential phenomenom may be less of a problem at lower clearing agent doses which are more efficiently disposed of by the liver.

Example 7

As an example of how to use the clearing agent object of this invention, the biodistribution in selected organs and tumor-to-organ (T/organ) ratios obtained when injecting the pretargeting probe ($^{125}$I-CC49-TCO) followed by the effector probe ($^{111}$In-15) with administration of single and repeated dose of clearing agent 12 are presented.

Nude female mice (n=4-6) bearing LS174T xenografts (0.38±0.23 g) were injected $^{125}$I-CC49-TCO (t=0, 100 μg/100 μl per mouse) followed by (a) one 160 μg/100 μl dose of galactose-MSA-tetrazine (12) 48 hours post mAb injection, or (b) two 160 μg/100 μl 12 doses 46 and 48 hours post mAb injection, or (c) two 160 μg/100 μl 12 doses 28 and 48 hours post mAb injection. At 50 hours post mAb injection, the mice received 8.52 μg $^{111}$In-tetrazine and were then sacrificed three hours later, blood was withdrawn by heart puncture and selected organs and tissues were harvested and blotted dry. The blood samples and tissues were weighed, added with 1 mL PBS and the radioactivity was counted in a gamma counter along with standards to determine the % ID/g. The biodistribution data of $^{125}$I-CC49-TCO and $^{111}$In-tetrazine are shown in Table 2 and the $^{111}$In-tetrazine T/organ values are shown in Table 3.

TABLE 2

Biodistribution of $^{125}$I-CC49-TCO and $^{111}$In-tetrazine in tumor bearing mice with administration of (a) one dose of clearing agent 12 48 h post mAb inhection, or (b) one dose at 46 and one at 48 hours post mAb injection, or (c) one dose at 28 and one at 48 hours post mAb injection. Data presented as mean % ID/g ± one standard deviation (n = 4-6).

|  | One dose (a)† | Two doses (b)† | Two doses (c)‡ |
|---|---|---|---|
| $^{125}$I-CC49-TCO | | | |
| blood | 0.45 ± 0.04 | 0.23 ± 0.13 | 0.16 ± 0.03 |
| tumor | 25.29 ± 6.13 | 15.25 ± 7.86 | 19.42 ± 3.68 |
| heart | 0.87 ± 0.21 | 0.43 ± 0.22 | 0.78 ± 0.10 |
| lung | 1.20 ± 0.24 | 0.58 ± 0.27 | 0.86 ± 0.09 |
| liver | 1.35 ± 0.48 | 2.35 ± 0.39 | 0.95 ± 0.13 |
| spleen | 0.76 ± 0.11 | 0.66 ± 0.25 | 0.65 ± 0.04 |
| kidney | 0.56 ± 0.11 | 0.31 ± 0.12 | 0.32 ± 0.03 |
| muscle | 0.39 ± 0.08 | 0.21 ± 0.10 | 0.21 ± 0.04 |
| bone | 0.34 ± 0.10 | 0.22 ± 0.08 | 0.21 ± 0.02 |
| brain | 0.02 ± 0.00 | 0.01 ± 0.00 | 0.01 ± 0.00 |
| $^{111}$In-tetrazine | | | |
| blood | 0.40 ± 0.10 | 0.10 ± 0.02 | 0.05 ± 0.00 |
| tumor | 2.98 ± 0.51 | 1.52 ± 0.48 | 4.30 ± 0.50 |
| heart | 0.45 ± 0.08 | 0.07 ± 0.02 | 0.05 ± 0.01 |
| lung | 0.97 ± 0.17 | 0.20 ± 0.07 | 0.16 ± 0.03 |
| liver | 0.27 ± 0.04 | 0.13 ± 0.01 | 0.13 ± 0.01 |
| spleen | 0.27 ± 0.04 | 0.10 ± 0.00 | 0.10 ± 0.01 |
| kidney | 1.07 ± 0.10 | 0.95 ± 0.06 | 1.18 ± 0.13 |
| muscle | 0.35 ± 0.08 | 0.09 ± 0.03 | 0.03 ± 0.00 |
| bone | 0.33 ± 0.12 | 0.10 ± 0.02 | 0.05 ± 0.01 |
| brain | 0.02 ± 0.00 | 0.01 ± 0.00 | 0.01 ± 0.00 |

†n = 4;
‡n = 6

TABLE 3

Biodistribution of $^{125}$I-CC49-TCO and $^{111}$In-tetrazine in tumor bearing mice with administration of (a) one dose of clearing agent 12 48 h post mAb inhection, or (b) one dose at 46 and one at 48 hours post mAb injection, or (c) one dose at 28 and one at 48 hours post mAb injection. Data presented as mean tumor-to-organ ratio (T/organ) ± one standard deviation (n = 4-6).

|  | One dose (a) | Two doses (b) | Two doses (c) |
|---|---|---|---|
| $^{125}$I-CC49-TCO | | | |
| blood | 56.0 ± 14.5 | 84.5 ± 49.0 | 143.4 ± 51.5 |
| heart | 29.0 ± 2.5 | 40.2 ± 19.9 | 29.9 ± 10.9 |
| lung | 21.1 ± 2.5 | 29.2 ± 12.2 | 27.1 ± 9.2 |
| liver | 19.7 ± 5.5 | 6.5 ± 3.5 | 25.3 ± 8.8 |
| spleen | 33.0 ± 6.6 | 22.9 ± 7.6 | 35.8 ± 13.7 |
| kidney | 45.2 ± 5.0 | 51.3 ± 18.7 | 73.7 ± 22.0 |
| muscle | 64.2 ± 8.9 | 75.5 ± 23.8 | 114.5 ± 39.7 |
| bone | 76.7 ± 16.6 | 69.3 ± 16.9 | 110.6 ± 37.5 |
| brain | 1046.4 ± 250.6 | 1580.9 ± 609.1 | 2272.8 ± 767.8 |
| $^{111}$In-tetrazine | | | |
| blood | 8.2 ± 4.1 | 15.2 ± 4.1 | 89.0 ± 14.3 |
| heart | 6.7 ± 1.3 | 25.6 ± 12.0 | 82.9 ± 21.3 |
| lung | 3.1 ± 0.5 | 8.5 ± 4.2 | 27.9 ± 7.0 |
| liver | 10.9 ± 1.7 | 11.5 ± 3.7 | 32.3 ± 5.9 |
| spleen | 11.3 ± 3.3 | 15.1 ± 4.9 | 42.4 ± 7.7 |
| kidney | 2.8 ± 0.3 | 1.6 ± 0.6 | 3.7 ± 0.8 |
| muscle | 9.2 ± 3.6 | 19.3 ± 9.2 | 146.3 ± 30.3 |
| bone | 10.5 ± 6.5 | 16.7 ± 6.7 | 93.5 ± 19.7 |
| brain | 148.05 ± 61.18 | 222.2 ± 73.6 | 750.2 ± 87.5 |

†n = 4;
‡n = 6

This example demonstrates the effect of single vs. double dose of clearing agent 12 on the biodistribution of $^{125}$I-CC49-TCO and, therefore, on $^{111}$In-tetrazine retention in tumor bearing mice.

As reported by Rossin et al. (Angew Chem Int Ed 2010, 49, 3375-8), the CC49-TCO construct has a sustained circulation in blood. Therefore, without the use of a clearing agent, 27 hours after injection of 100 μg mAb/mouse the T/blood ratio is low (2.8±0.8). Consequently, the reaction between non-tumor bound mAb-TCO and the pretargeting effector probe ($^{111}$In-tetrazine) produces also a low T/blood ratio (2.2±0.5 when administering 21.3 μg tetrazine/mouse 24 hours post mAb injection) and a relatively high $^{111}$In-radioactivity background in non-target organs.

Here, the administration of 100 μg CC49-TCO per mouse followed by one dose of clearing agent 12 (160 μg, t=48 hours) results in high T/organ ratios (Table 3) due to the depletion of mAb from blood (Table 2). As expected, the T/organ values for blood, muscle, and blood rich organs (beside liver and spleen) increase further with the administration of a second dose of clearing agent two hours after the first one due to the removal of residual $^{125}$I-CC49-TCO still circulating after the first chase. Notably, when the delay between the two clearing agent doses increases from 2 to 20 hours, the removal of $^{125}$I-CC49-TCO from blood is most effective. This is possibly due to the long time needed for the liver to process the first mAb-clearing agent construct dose. In fact, the galactose-containing construct binds avidly to the Ashwell receptors on hepatocytes, then the receptor-ligand complex internalizes into endocytic vesicles, the cargo slowly dissociates from the receptors ($K_{off}$<0.9×10$^{-5}$ sec$^{-1}$) and traffics to the Golgi-lysosome region where it is degraded while the receptors re-cycle to the cell surface (A. L. Schwartz, Crit Rev Biochem Mol Biol, 1984, 16, 207-233). The biodistribution data confirm that metabolism and excretion of the mAb-clearing agent construct is rather slow. In fact, when the two doses of clearing agent are administered 46 and 48 hours after mAb injection, a significant amount of radioactivity is still in the liver (2.35±0.39% ID/g) and intestine (1.44±0.67% ID) at the time of mouse sacrifice (53 hours post mAb injection). On the contrary, when the first dose of clearing agent is administered approximately 20 hours before the second one, at the time of mouse sacrifice the mAb-related radioactivity in liver and intestine is significantly reduced (0.95±0.13% ID/g and 0.56±0.13% ID in liver and intestine, respectively).

The depletion of non-tumor bound CC49-TCO from the system translates into a significant decrease in $^{111}$In-tetrazine retention in all considered organs beside tumor (tetrazine reaction with tumor-bound CC49-TCO) and kidney (tetrazine excretion). Consequently, in the improved experimental conditions (two clearing agent doses separated by a long interval (c)) the T/blood and T/muscle ratio for $^{111}$In-tetrazine are 89.0±14.3 and 146.3±30.3, respectively, which will have very favourable implications for the dosimetry in radiation sensitive organs such as the bone marrow with respect to that attainable with one single dose of clearing agent (T/blood=8.2±4.1 and T/muscle=9.2±3.6).

Example 8

Chemical Synthesis of Additional Trans-Cyclooctene Constructs and their Corresponding Antibody Conjugate Conjugation of the TCOs to antibodies was performed as described in R. Rossin, P. Renart Verkerk, Sandra M. van den Bosch, R. C. M. Vulders, 1. Verel, J. Lub, M. S. Robillard, Angew Chem Int Ed 2010, 49, 3375-78.

Synthesis of TCO (E-minor)-2,5-Dioxopyrrolidin-1-yl 4-((cyclooct-4-enyloxy)methyl)benzoate 18

Figure 13:
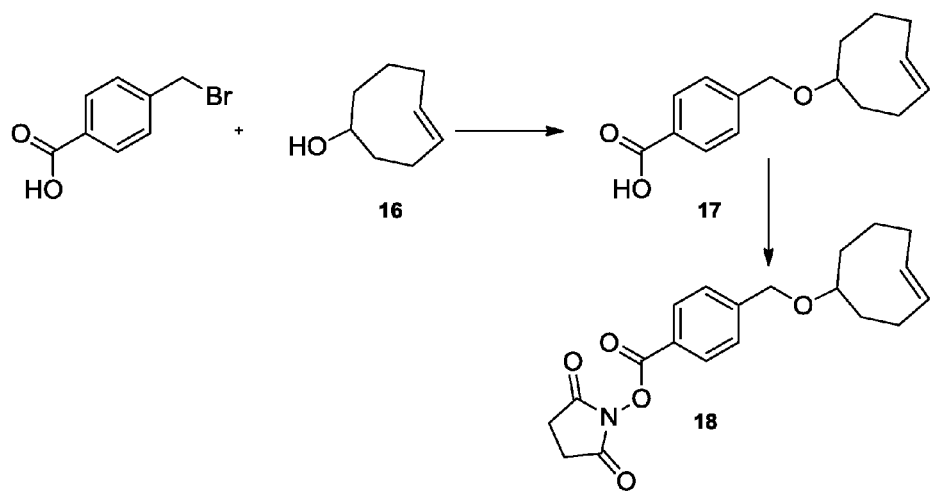
FIG. 13 depicts the synthesis route of TCO (E-minor)-2, 5-Dioxopyrrolidin-1-yl 4-((cyclooct-4-enyloxy)methyl)benzoate 18

Reference is made to FIG. 13

(E)-Cyclooct-4-enol (16, minor isomer) was synthesized according to the aforementioned literature procedure. A 60% sodium hydride dispersion (2.1 g, 53 mmol) was added to an ice-bath-cooled solution of 16 (2.53 g, 20.1 mmol) in 50 mL tetrahydrofuran After stirring for 4 h at room temperature, the mixture was cooled again and 4-bromomethylbenzoic acid (4.53 g, 21.1 mmol) was added in portions over a 5 min. period. 25 ml of tetrahydrofuran were added and the suspension was stirred for 4 days at room temperature. Ice was added, followed by 12.0 g of citric acid. The mixture was extracted twice with 150 mL tert-butyl methyl ether. The organic layers were washed with 25 mL water, dried and evaporated. The residue was purified by chromatography with 80 g silica gel and heptane containing a gradually increasing amount of ethyl acetate as the eluent. The product fractions (no full separation between product and starting alcohol) were combined and recrystallized from ca. 30 mL heptane (cooling to −15° C.), yielding 17 (0.86 g, 17%) as a white solid. It was dissolved in 40 mL dichloromethane. N-hydroxysuccinimide (0.48 g, 4.17 mmol) was added and the mixture was cooled in ice. N,N'-dicyclohexylcarbodiimide (0.80 g, 3.88 mmol) was added and the mixture was stirred for 30 min in ice, then 18 h at room temperature. Filtration, washing with dichloromethane, rotary evaporation and chromatography on 25 g silicagel using heptane-ethyl acetate as the eluent gave the product. The evaporated product fractions were mixed with 75 mL tert-butyl methyl ether and the mixture was warmed to 60° C. to give a solution. The solution was concentrated to 20 mL. Gradual addition of 50 mL heptane resulted in precipitation of the product. It was collected by filtration and washed with heptane to afford 1.05 g of 18 (15%). 1H NMR (300 MHz, CDCl$_3$): δ=8.10 (d, J=8.5 Hz, 2H), 7.46 (d, J=8.5 Hz, 2H), 5.73 (m, 1H), 5.52 (m, 1H), 4.60 (d, J=13.4 Hz, 1H), 4.45 (d, J=13.4 Hz, 1H), 3.65 (m, 1H), 2.92 (s, 4H), 2.43-1.10 (m, 10H); $^{13}$C NMR (75 MHz, CDCl$_3$): δ=169.0 (q), 161.5 (q), 146.7 (q), 135.1 (t), 132.1 (t), 130.4 (t), 127.0 (t), 123.7 (q), 85.3 (t), 68.0 (s), 40.5 (s), 37.7 (s), 34.2 (s), 32.7 (s), 31.4 (s), 25.4 (s); HRMS (ESI, m/z): Calcd for C$_{20}$H$_{23}$NO$_5$Na' ([M-Na]$^+$): 380.1474. Found: 380.1472.

Synthesis of TCO Minor (E)-2,5-dioxopyrrolidin-1-yl 2-(cyclooct-4-en-1-yloxy)acetate 20

Figure 14:
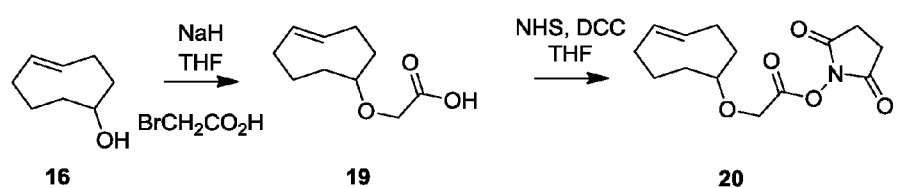
FIG. 14 depicts the synthesis foute of TCO Minor (E)-2, 5-dioxopyrrolidin-1-yl 2-(cyclooct-4-en-1-yloxy)acetate 20

Reference is made to FIG. 14 detailing the synthesis route.
To an ice-cooled solution of 16 (minor, 0.78 g, 6.19 mmol) in THF (30 mL) was added sodium hydride in oil (60%, 0.94 g, 23.5 mmol). The mixture was stirred for 15 min at RT, then heated to 50° C. for 1 h. The mixture was cooled in ice, and bromoacetic acid (1.41 g, 10.14 mmol) was added. The suspension was stirred at ca. 25° C. for 20 h (a sample indicated that no coupling had taken place), then for 6 h at 55° C., 3 days at 25° C., and another 6 h at 55° C. Most of the THF was removed by rotary evaporation and 50 mL MTBE, followed by ice and 25 mL water. The layers were separated and the aqueous layer was extracted with 30 mL MTBE. The successive organic layers were washed with 25 mL water. The combined aqueous layers were cooled in ice, 50 mL MTBE was added, followed by 5.1 g citric acid. The layers were separated and the aqueous layer was extracted with 50 mL MTBE. Drying and rotary evaporation left a residue (19) which was used as such in the next step (it contained a considerable amount of bromoacetic acid). $^1$H-NMR (CDCl$_3$): δ 1.2-2.45 (m, 10H), 3.65-3.75 (m, 1H), 4.1 (s, 2H), 5.45-5.65 (m, 2H).

Product 19 was dissolved in 30 mL dichloromethane. N-hydroxysuccinimide (1.60 g, 13.91 mmol) was added and the mixture was cooled in ice. DCC (3.11 g, 15.10 mmol) was added and the mixture was stirred in ice for 30 min, then at RT for 3 h. Filtration, rotary evaporation and chromatography on 40 g silicagel using a toluene and then dichloromethane as the eluents afforded 20, mixed with the NHS ester of bromoacetic acid. The mixture was dissolved in 25 mL MTBE, and 25 mL heptane was added to the solution. After stirring for 2 h, the mixture was filtered (the solid being the NHS ester of bromoacetic acid). The filtrate was rotary evaporated, the residue was dissolved in warm MTBE, some heptane was added, and the solution was cooled to RT. This precipitated the product. Filtration afforded 30 mg of product 20 (0.11 mmol, 2%). $^1$H-NMR (CDCl$_3$): δ 1.1-2.45 (m, 10H), 2.85 (s, 4H), 3.65-3.75 (m, 1H), 4.4 (s, 2H), 5.4-5.7 (m, 2H).

Example 9

As an example of how to use the clearing agent object of this invention, the biodistribution in selected organs and tumor-to-organ (T/organ) ratios obtained when injecting the pretargeting probe ($^{125}$I-CC49-TCO) followed by $^{177}$Lu-labeled tetrazine 15 with the administration of one or two doses of clearing agent 12 are presented. The galactose-MSA-tetrazine 12 used in this example was synthesized according to the procedure 2 depicted in FIG. 5 where the synthetic intermediate 11 was purified by size exclusion chromatography before reaction with 5 to eliminate albumin aggregates.

Nude female mice (n=4) bearing LS174T xenografts (0.29±0.16 g) were injected $^{125}$I-CC49-TCO 18 (t=0, 100 μg/100 μl per mouse) followed by one 160 μg/100 μl dose of galactose-MSA-tetrazine (12) 30 hours post mAb injection, or two 160 μg/100 μl 12 doses 30 and 48 hours post mAb injection. Two hours after the last clearing agent dose the mice were administered 8.52 μg of $^{177}$Lu-labeled tetrazine 15 (10 equiv. with respect to mAb) and were sacrificed 3 hours post tetrazine injection. Blood was withdrawn by heart puncture and selected organs and tissues were harvested and blotted dry. The blood samples and tissues were weighed, added with 1 mL PBS and the radioactivity was counted in a gamma counter along with standards to determine the % ID/g. The biodistribution data and tumor/organ ratios are shown in Tables 4 and 5. The differences between columns were analyzed using the two-tailed unpaired t-test (Graphpad Prism v. 5.01)

TABLE 4

Biodistribution of $^{125}$I-CC49-TCO 18 and $^{177}$Lu-tetrazine 15 in tumor bearing mice with administration of one dose of clearing agent 12 30 h post mAb injection, or two doses at 30 and 48 hours post mAb injection. Data presented as mean % ID/g ± one standard deviation (n = 4).

|  | One dose | Two doses |
|---|---|---|
| $^{125}$I-CC49-TCO | | |
| blood | 1.16 ± 0.43 | 0.40 ± 0.09* |
| tumor | 31.59 ± 7.44 | 25.39 ± 6.68 |
| heart | 1.15 ± 0.35 | 0.56 ± 0.07* |
| lung | 1.63 ± 0.29 | 0.84 ± 0.11** |
| liver | 4.20 ± 1.16 | 1.57 ± 0.19** |
| spleen | 1.66 ± 0.40 | 0.59 ± 0.12** |
| kidney | 0.93 ± 0.17 | 0.49 ± 0.04** |
| muscle | 0.68 ± 0.30 | 0.26 ± 0.04 |
| bone | 0.56 ± 0.23 | 0.25 ± 0.05 |
| brain | 0.05 ± 0.02 | 0.02 ± 0.01 |
| $^{177}$Lu-tetrazine | | |
| blood | 0.17 ± 0.06 | 0.03 ± 0.00** |
| tumor | 7.48 ± 1.46 | 5.38 ± 0.48* |
| heart | 0.12 ± 0.03 | 0.04 ± 0.00** |
| lung | 0.28 ± 0.05 | 0.21 ± 0.03 |
| liver | 0.23 ± 0.00 | 0.18 ± 0.02** |
| spleen | 0.15 ± 0.03 | 0.09 ± 0.01** |
| kidney | 1.06 ± 0.39 | 1.58 ± 0.14* |
| muscle | 0.08 ± 0.04 | 0.05 ± 0.03 |
| bone | 0.06 ± 0.03 | 0.08 ± 0.08 |
| brain | 0.01 ± 0.00 | 0.00 ± 0.00* |

*P < 0.5;
**P < 0.05.

TABLE 5

Biodistribution of $^{125}$I-CC49-TCO 18 and $^{177}$Lu-tetrazine 15 in tumor bearing mice with administration of one dose of clearing agent 12 30 h post mAb injection, or two doses at 30 and 48 hours post mAb injection. Data presented as mean tumor/organ ratio ± one standard deviation (n = 4).

|  | One dose | Two doses |
|---|---|---|
| $^{125}$I-CC49-TCO | | |
| T/blood | 30.6 ± 12.5 | 67.4 ± 31.0 |
| T/heart | 28.9 ± 8.2 | 46.0 ± 13.8 |
| T/lung | 19.8 ± 5.8 | 30.6 ± 8.1 |
| T/liver | 8.1 ± 3.0 | 16.4 ± 4.8* |
| T/spleen | 19.4 ± 3.9 | 43.5 ± 10.6** |
| T/kidney | 34.2 ± 6.9 | 52.6 ± 17.2 |
| T/muscle | 54.2 ± 22.9 | 101.6 ± 41.4 |
| T/bone | 61.8 ± 19.3 | 105.2 ± 35.6 |
| T/brain | 743.5 ± 316.9 | 1498.0 ± 1019.1 |
| $^{177}$Lu-tetrazine | | |
| T/blood | 45.9 ± 14.2 | 195.7 ± 12.9**** |
| T/heart | 64.7 ± 18.0 | 142.4 ± 18.5*** |
| T/lung | 28.1 ± 11.8 | 26.2 ± 3.9 |
| T/liver | 32.4 ± 6.3 | 30.8 ± 2.9 |
| T/spleen | 50.5 ± 10.9 | 63.7 ± 9.2 |
| T/kidney | 7.9 ± 3.3 | 3.4 ± 0.4* |
| T/muscle | 128.5 ± 83.7 | 140.9 ± 67.1 |
| T/bone | 136.1 ± 68.7 | 123.3 ± 80.3 |
| T/brain | 935.9 ± 297.1 | 1146.7 ± 122.9 |

*P < 0.5;
**P < 0.05;
***P < 0.005;
****P < 0.0001

Similar to Example 7, the results reported here confirm that a double dose of clearing agent 12 is more effective than one single dose in depleting $^{125}$I-CC49-TCO 18 from blood and normal tissues (Table 4). Furthermore, here we show that an improved removal of non-tumor bound CC49-TCO from the system translates into a significant decrease in $^{177}$Lu-tetrazine retention in most considered healthy tissues. Notably, the tetrazine accumulation in the tumor is not affected by the administration of two doses of clearing agent as the slight decrease observed in the % ID/g (Table 4) is most likely due to radioactivity "dilution" within the tumor caused by rapid tumor growth (the tumor average size in the one single vs double dose groups is 0.24±0.22 g and 0.40±0.07 g, respectively). The lack of tumor blocking by galactose-MSA-tetrazine is due to the high MW of Gal-MSA-tetrazine, which hampers extravasation into tumor tissues in the short time between injection and liver capture. Noteworthy, contrary to galactose-HSA-biotin, no tumor blocking metabolites are recirculated after galactose-MSA-tetrazine break down in the liver. This was expected as unreacted tetrazines which may be released following clearing agent metabolism would be protonated (and therefore trapped) and/or degraded in the lysosomal compartment of hepatocytes. Consequently, in the optimized experimental conditions (with two clearing agent doses separated by a long interval) a very high T/blood ratio is obtained for $^{177}$Lu-tetrazine (195.7±12.9; Table 5). This will have very favorable implications for the dosimetry in radiosensitive organs such as the bone marrow with respect to the dose attainable with a single administration of clearing agent (T/blood ratio 45.9±14.2).

Example 10

Biodistribution of $^{177}$Lu-Tetrazine 15 in Tumor Bearing Mice Mice Pretargeted with CC49-TCO 20

Tumor-bearing mice (ca. 100 mm$^3$ tumor size; n=4) were injected with $^{125}$I-CC49 functionalized with 7.5 TCO-20 groups (100 μg/mouse, ca. 0.2 MBq). Thirty and 48 hours post-mAb injection the mice received one dose of clearing agent (galactose-MSA-tetrazine, 160 μg/dose) followed 2 h later by $^{177}$Lu-tetrazine 15 (10 eq. with respect to the mAb, ca. 0.5 MBq). Three hours post-tetrazine injection the mice were anesthetized and sacrificed by cervical dislocation, blood was withdrawn by heart puncture, organs and tissues of interest were harvested and blotted dry. All collected samples were weighed and added with 1 mL PBS. The sample radioactivity was measured in a gamma-counter with a dual-isotope protocol (10-80 keV window for $^{125}$I and 155-380 keV window for $^{177}$Lu) along with standards to determine the percent injected dose per gram tissue (% ID/g).

The biodistribution data show high tumor uptake of $^{125}$I-CC49-TCO 20. The tumor uptake was higher than that obtained with other TCO constructs (vide infra), reasonably due to the long blood circulation of CC49 functionalized with 7.5 TCO-20 groups. On the contrary, the mAb retention in all other organs was low due to the administration of two doses of a clearing agent that captured the circulating CC49-TCO and directed it to the liver, where it was rapidly metabolized. As a result of the higher mAb uptake in tumor, also the $^{177}$Lu-tetrazine uptake was significantly higher than that obtained in previous experiments (vide infra). Also, due to the removal of non-tumor bound CC49-TCO in the chase step before tetrazine administration, $^{177}$Lu uptake in all other organs was negligible. Only kidney exhibited a rather high retention of $^{177}$Lu as a consequence of tetrazine urinary excretion. This resulted in high target-to-non target ratios in all considered organs beside kidney. Noteworthy, 34±4% and 10±1% of the TCOs present in tumor and blood respectively had reacted with tetrazine.

TABLE 6

Dual isotope biodistribution data 3 h after injection of $^{177}$Lu-tetrazine 15 (8.5 μg/80 μL per mouse, ca. 0.5 MBq), 50 h after the administration of $^{125}$I-CC49-TCO-20 (100 μg/100 μL per mouse, ca. 0.2 MBq). Data presented as % ID/gram ± SD or tumor/organ ratio ± SD (n = 4).

|  | $^{125}$I-CC49-TCO | $^{177}$Lu-tetrazine | $^{125}$I-CC49-TCO | $^{177}$Lu-tetrazine |
|---|---|---|---|---|
|  | % ID/gram | | Tumor/organ | |
| Tumor | 32.88 ± 4.35 | 9.25 ± 2.16 | | |
| Blood | 0.31 ± 0.13 | 0.03 ± 0.00 | 129 ± 74 | 304 ± 80 |
| Heart | 0.62 ± 0.22 | 0.05 ± 0.01 | 60 ± 26 | 187 ± 20 |
| Lung | 0.99 ± 0.24 | 0.24 ± 0.02 | 35 ± 8 | 39 ± 8 |
| Liver | 2.35 ± 0.82 | 0.19 ± 0.02 | 16 ± 6 | 50 ± 10 |
| Spleen | 0.67 ± 0.07 | 0.09 ± 0.01 | 49 ± 5 | 108 ± 22 |
| Kidney | 0.47 ± 0.10 | 1.50 ± 0.24 | 72 ± 14 | 6 ± 2 |
| Muscle | 0.22 ± 0.08 | 0.03 ± 0.00 | 162 ± 62 | 328 ± 96 |
| Bone | 0.29 ± 0.08 | 0.08 ± 0.04 | 119 ± 33 | 142 ± 59 |
| Brain | 0.02 ± 0.00 | 0.01 ± 0.00 | 2304 ± 668± | 1674 ± 243 |

Example 11

Antibody DOTA Conjugation and $^{177}$Lu-Radiolabeling 2 mg CC49 (5 mg/mL solution in PBS) was modified with 4 eq. of DOTA-NHS (10 mg/mL DMSO; Macrocyclics) in a total volume of 500 μL PBS. The pH was adjusted to 9 with 1M sodium carbonate buffer pH 9.6. The reaction was carried out under agitation for 30 min at room temperature in the dark. Subsequently, the DOTA-CC49 was extensively washed with PBS using an Amicon Ultra-15 centrifugal device and the mAb concentration in the final solution was measured by Nanodrop. The number of DOTA groups per mAb molecule was calculated by reacting a known amount of DOTA-CC49 with a known excess of LuCl$_3$ (spiked with radioactive $^{177}$Lu) for 2 h at 37° C. and by measuring the % bound Lu through radio-ITLC ($n_{DOTA}=n_{Lu}\times$reaction yield/100). With this procedure an average of 3 DOTA groups per CC49 molecule was detected after conjugation. A stock solution of $^{177}$Lu was prepared in 1M ammonium acetate pH 5.0 (metal free). Then the desired amount of radioactivity was added to the DOTA-CC49 solution (100 μg in 0.2M ammonium acetate pH 7.0) and the solution was diluted to 50 μL with 1M ammonium acetate pH 5.0. The labeling mixture was incubated for 1 h at 37° C. then 5 μL 10 mM DTPA was added and the solution was incubated 10 min more. The radiolabeling yield was determined by radio-ITLC (typically 65-70%) then the crude $^{177}$Lu-DOTA-CC49 was purified twice through Zeba desalting spin columns (7 or 40 kDa MW cut-off, Pierce) pre-equilibrated with saline solution. The recovery of $^{177}$Lu-DOTA-CC49 in then eluted solution was estimated from the labeling yield and from the radioactivity recovery from the spin column. The radiochemical purity of $^{177}$Lu-DOTA-CC49 was assessed by ITLC, SDS-PAGE and SEC-HPLC (typically >98%), then the specific activity was adjusted to the desired value by adding non-radioactive mAb.

Example 12

Figure 15:
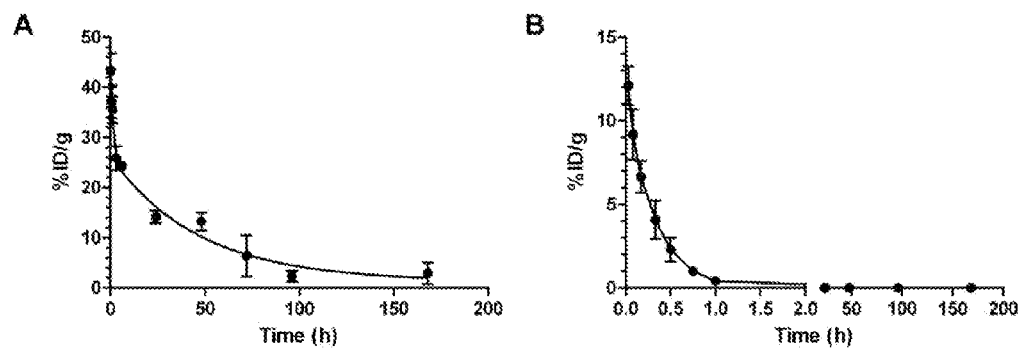
FIG. 15 depicts the blood profile of (A) $^{177}$Lu-DOTA-CC49 and (B) CC49-TCO 18 pretargeted $^{177}$Lu-tetrazine 15 in tumor bearing mice. Data points and error bars represent the mean % ID/g and one SD, respectively (n=4).
Figure 16:
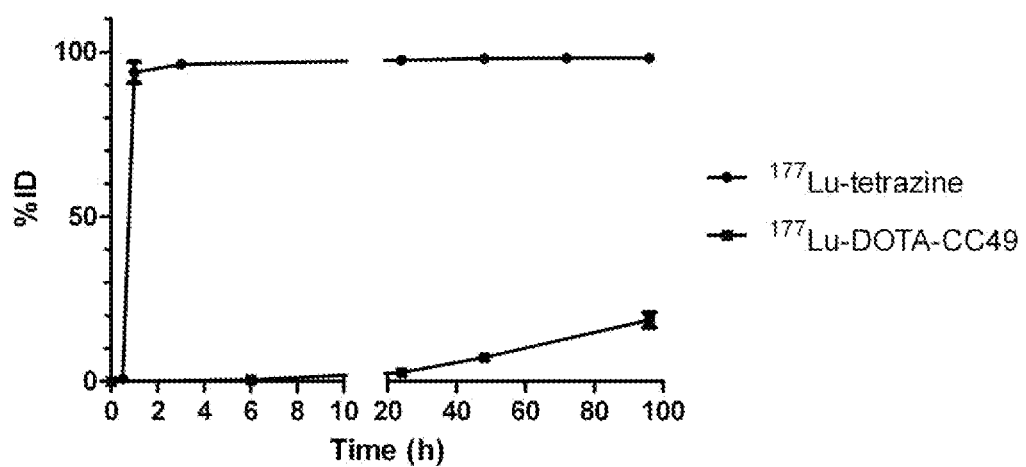
FIG. 16 depicts the excretion profile (combined feces and urine) of $^{177}$Lu-DOTA-CC49 and CC49-TCO-18 pretargeted $^{177}$Lu-tetrazine 15 in tumor bearing mice. The data points and error bar represent the mean % ID and one SD, respectively (n=4).

Comparative Biodistribution of Directly Labeled $^{177}$Lu-DOTA-CC49 and of CC49-TCO-18 Pretargeted $^{177}$Lu-Tetrazine Groups of 4 mice bearing LS174T xenografts (70-100 mm$^3$) were injected either with directly labeled $^{177}$Lu-DOTA-CC49 (100 μg/100 μl, ca. 0.5 MBq per mouse) or with CC49-TCO-18 pretargeted $^{177}$Lu-tetrazine 15 (100 μg/100 μl CC49-TCO-18 followed by two 160 μg/100 μl doses of galactose-MSA-tetrazine 12 at 30 and 48 hours and by 8.52 μg/80 μl $^{177}$Lu-tetrazine 15, 0.8-1.2 MBq per mouse, containing 100 μg gentisic acid). One group of mice injected with $^{177}$Lu-DOTA-CC49 and one injected with pretargeted $^{177}$Lu-tetrazine were used to evaluate the early blood distribution of the two tracers by withdrawing blood samples from the vena saphena at selected time points (2, 30, and 60 min for $^{177}$Lu-DOTA-CC49 and 2, 5, 10, 20, 30, and 45 min for pretargeted $^{177}$Lu-tetrazine) (FIG. 15). These two groups of mice were then sacrificed 3 h and 1 h after the injection of $^{177}$Lu-DOTA-CC49 and $^{177}$Lu-tetrazine, respectively. All other groups of mice were sacrificed at various time points up to 7 days post tracer injection. After sacrifice, blood was withdrawn by heart puncture and selected organs and tissues were harvested and blotted dry. The blood samples and tissues were weighed, added with 1 mL PBS and the radioactivity was counted in a gamma counter along with standards to determine the % ID/g and % ID (Tables 7-8). Two additional groups of tumor bearing mice were used for excretion profiles (FIG. 16). The mice injected with $^{177}$Lu-DOTA-CC49 were housed in filtered caging units and at various time points the bedding was counted in a gamma counter along with standards. The other group of mice was injected with $^{177}$Lu-tetrazine at higher specific activity (ca. 12 MBq/8.52 μg tetrazine per mouse) and whole body clearance was monitored by measuring the animals in a dose calibrator at various time points.

TABLE 7

Biodistribution of $^{177}$Lu-DOTA-CC49 in tumor bearing mice. Data presented as mean % ID/g and % ID ± one standard deviation (n = 4).

| Organs | 3 hour | 6 hours | 1 day | 2 days | 3 days | 4 days | 7 days |
|---|---|---|---|---|---|---|---|
| | % ID/g | | | | | | |
| blood | 25.86 ± 2.44 | 24.37 ± 0.63 | 14.20 ± 1.25 | 13.23 ± 1.78 | 6.43 ± 4.11 | 3.86 ± 4.81 | 2.92 ± 2.15 |
| tumor | 15.79 ± 2.77 | 23.75 ± 1.69 | 49.44 ± 6.40 | 61.68 ± 16.24 | 73.26 ± 26.69 | 45.50 ± 3.97 | 66.57 ± 25.24 |
| heart | 5.53 ± 0.70 | 5.48 ± 0.91 | 3.40 ± 0.77 | 4.39 ± 1.91 | 1.58 ± 0.90 | 0.89 ± 1.01 | 0.79 ± 0.54 |
| lung | 9.90 ± 1.78 | 8.86 ± 0.76 | 5.99 ± 0.42 | 6.53 ± 0.62 | 3.55 ± 1.94 | 2.33 ± 2.31 | 2.10 ± 1.34 |
| liver | 9.13 ± 1.19 | 9.80 ± 1.19 | 9.51 ± 3.98 | 9.92 ± 1.98 | 13.91 ± 5.92 | 15.90 ± 6.88 | 11.56 ± 3.18 |
| spleen | 5.90 ± 1.38 | 6.29 ± 1.06 | 4.94 ± 1.26 | 5.47 ± 0.81 | 5.15 ± 0.93 | 4.34 ± 1.21 | 4.71 ± 1.65 |
| kidney | 6.54 ± 0.43 | 7.27 ± 0.22 | 4.21 ± 0.60 | 4.49 ± 0.51 | 2.88 ± 1.44 | 1.81 ± 0.81 | 1.77 ± 0.38 |
| bladder | 1.15 ± 0.11 | 2.12 ± 0.66 | 3.63 ± 0.91 | 3.80 ± 0.32 | 2.19 ± 1.12 | 1.22 ± 1.08 | 1.01 ± 0.59 |
| uterus | 4.61 ± 1.89 | 7.75 ± 1.43 | 6.11 ± 0.45 | 7.25 ± 1.62 | 3.30 ± 1.62 | 5.33 ± 6.35 | 2.50 ± 1.38 |
| ovaries | 6.15 ± 0.94 | 5.13 ± 0.66 | 5.68 ± 0.82 | 6.24 ± 0.65 | 3.90 ± 1.39 | 2.53 ± 1.63 | 2.48 ± 1.24 |
| muscle | 1.82 ± 0.15 | 1.21 ± 0.39 | 1.53 ± 0.63 | 1.42 ± 0.20 | 0.76 ± 0.39 | 0.40 ± 0.34 | 0.34 ± 0.18 |

TABLE 7-continued

Biodistribution of $^{177}$Lu-DOTA-CC49 in tumor bearing mice. Data presented as mean % ID/g and % ID ± one standard deviation (n = 4).

| Organs | 3 hour | 6 hours | 1 day | 2 days | 3 days | 4 days | 7 days |
|---|---|---|---|---|---|---|---|
| bone | 2.76 ± 0.67 | 2.21 ± 0.08 | 1.85 ± 0.46 | 1.59 ± 0.38 | 1.40 ± 0.49 | 0.85 ± 0.36 | 0.75 ± 0.12 |
| brain | 0.87 ± 0.24 | 0.83 ± 0.18 | 0.54 ± 0.11 | 0.57 ± 0.10 | 0.23 ± 0.13 | 0.19 ± 0.17 | 0.12 ± 0.09 |
| | | | | % ID | | | |
| stomach | 0.35 ± 0.06 | 0.30 ± 0.07 | 0.25 ± 0.08 | 0.35 ± 0.10 | 0.18 ± 0.05 | 0.07 ± 0.03 | 0.13 ± 0.09 |
| lg. intestine | 2.54 ± 0.14 | 2.49 ± 0.18 | 1.52 ± 0.58 | 1.95 ± 0.27 | 0.91 ± 0.38 | 0.56 ± 0.14 | 0.64 ± 0.39 |
| sm. intestine | 1.07 ± 0.15 | 1.24 ± 0.10 | 0.90 ± 0.23 | 1.15 ± 0.24 | 0.85 ± 0.25 | 0.58 ± 0.12 | 0.56 ± 0.29 |

TABLE 8

Biodistribution of CC49-TCO-18 pretargeted $^{177}$Lu-tetrazine 15 in tumor bearing mice. Data presented as mean % ID/g or % ID ± one standard deviation (n = 4).

| Organs | 1 hours | 3 hours | 6 hours | 1 day | 2 days | 4 days | 7 days |
|---|---|---|---|---|---|---|---|
| | | | | % ID/g | | | |
| blood | 0.42 ± 0.20 | 0.03 ± 0.00 | 0.02 ± 0.00 | 0.01 ± 0.00 | 0.01 ± 0.00 | 0.00 ± 0.00 | 0.00 ± 0.00 |
| tumor | 4.71 ± 1.13 | 5.38 ± 0.48 | 4.53 ± 1.69 | 3.83 ± 0.95 | 3.15 ± 1.32 | 2.06 ± 0.84 | 1.02 ± 0.36 |
| heart | 0.16 ± 0.05 | 0.04 ± 0.00 | 0.03 ± 0.01 | 0.03 ± 0.00 | 0.03 ± 0.01 | 0.02 ± 0.00 | 0.01 ± 0.00 |
| lung | 0.54 ± 0.15 | 0.21 ± 0.03 | 0.11 ± 0.02 | 0.10 ± 0.01 | 0.08 ± 0.03 | 0.06 ± 0.01 | 0.04 ± 0.01 |
| liver | 0.29 ± 0.08 | 0.18 ± 0.02 | 0.15 ± 0.01 | 0.13 ± 0.02 | 0.11 ± 0.02 | 0.14 ± 0.02 | 0.13 ± 0.03 |
| spleen | 0.17 ± 0.04 | 0.09 ± 0.01 | 0.07 ± 0.01 | 0.07 ± 0.01 | 0.07 ± 0.01 | 0.07 ± 0.01 | 0.08 ± 0.01 |
| kidney | 2.38 ± 0.55 | 1.58 ± 0.14 | 1.09 ± 0.18 | 1.01 ± 0.13 | 0.49 ± 0.07 | 0.34 ± 0.02 | 0.19 ± 0.04 |
| bladder | 2.21 ± 1.15 | 0.85 ± 0.64 | 0.20 ± 0.08 | 0.20 ± 0.06 | 0.12 ± 0.07 | 0.13 ± 0.04 | 0.15 ± 0.02 |
| uterus | 2.80 ± 1.64 | 0.35 ± 0.42 | 0.10 ± 0.04 | 0.09 ± 0.02 | 0.12 ± 0.09 | 0.10 ± 0.07 | 0.21 ± 0.16 |
| ovaries | 0.57 ± 0.37 | 0.21 ± 0.19 | 0.09 ± 0.02 | 0.08 ± 0.03 | 0.10 ± 0.06 | 0.09 ± 0.02 | 0.08 ± 0.04 |
| muscle | 0.23 ± 0.21 | 0.05 ± 0.03 | 0.02 ± 0.00 | 0.02 ± 0.00 | 0.02 ± 0.01 | 0.01 ± 0.00 | 0.01 ± 0.00 |
| bone | 1.08 ± 1.34 | 0.17 ± 0.19 | 0.03 ± 0.00 | 0.03 ± 0.01 | 0.02 ± 0.00 | 0.02 ± 0.01 | 0.01 ± 0.00 |
| brain | 0.03 ± 0.03 | 0.00 ± 0.00 | 0.00 ± 0.00 | 0.00 ± 0.00 | 0.00 ± 0.00 | 0.00 ± 0.00 | 0.00 ± 0.00 |
| | | | | % ID | | | |
| stomach | 0.10 ± 0.10 | 0.02 ± 0.01 | 0.01 ± 0.01 | 0.04 ± 0.05 | 0.01 ± 0.01 | 0.01 ± 0.00 | 0.01 ± 0.00 |
| lg. intestine | 0.38 ± 0.11 | 0.15 ± 0.04 | 0.05 ± 0.01 | 0.06 ± 0.06 | 0.07 ± 0.08 | 0.03 ± 0.02 | 0.02 ± 0.01 |
| sm. intestine | 0.16 ± 0.03 | 0.22 ± 0.07 | 0.38 ± 0.26 | 0.09 ± 0.05 | 0.06 ± 0.06 | 0.04 ± 0.04 | 0.07 ± 0.04 |

As expected, the directly labeled $^{177}$Lu-DOTA-CC49 exhibited a long circulation with a two-phase blood elimination profile ($T_\alpha$=1.0 h and $T_\beta$=32.6 h) and a total half-life of 22 h (calculated as $T_{1/2}$=ln 2×AUC/$C_0$). As a consequence of the long blood circulation, the mAb uptake in tumors was high with a tumor-to-blood ratio ranging from ca. 1 six hours post injection to ca. 30 four days post injection. The whole-body mAb clearance was slow with only ca. 20% of the injected activity recover in urine and feces 4 days post injection. Therefore, during the whole observation time (7 days) a high amount of radioactivity was retained in all considered organs, especially in lung, liver, spleen and in the reproductive system (Table 7).

On the contrary, in the CC49-TCO pretargeted mice $^{177}$Lu-tetrazine eliminated rapidly from blood ($T_{1/2}$=11.2 min) and 3 hours post injection over 95% of the injected activity was already excreted in the urine. As a consequence, the tumor uptake (% ID/g) peaked within few hours post injection (Table 8) and then decreased with time. However, no release of radioactivity from the tumor was observed during the 7 days of the experiment, thus confirming in vivo stability of the Diels-Alder reaction product, and the tumor uptake decrease was mainly due to tumor growth. Among the considered organs, the only non target organ that retained a sizeable amount of tetrazine was the kidney. However, within few days post injection the radioactivity cleared effectively also from this organ. Noticeably, despite the relatively low absolute tumor uptake, the tumor-to-blood ratio of pretargeted $^{177}$Lu-tetrazine was ca 200 already 3 hours post injection and increased to over 500 by the end of the experiment. This will have very favorable implications for the dosimetry in radiosensitive organs such as the bone marrow with respect to the long circulating directly labeled mAb, despite the higher uptake in tumor of the $^{177}$Lu-DOTA-CC49.

Example 13

Human and Mouse Dosimetry

Comparison Between Conventional Radioimmunortherapy with Pretargeting with the Diels-Alder Reaction Radiation dosimetry estimates were calculated for a male human model (standard 73 Kg adult) and for a voxelized mouse model by using the mouse biodistribution data (Example 12, Tables 7 and 8) according to the MIRD methodology. Activity concentration in these organs were converted in percent injected dose (% ID) and decay corrected to the time of injection. The % ID for blood, muscle and bone were estimated from the % ID/g of tissue and assuming 6%, 42% and 11% of the body weight. Whenever possible the time activity curves were fitted by a two-phase exponential clearance function. The fitted function was then integrated analytically to yield the organ residence times (Table 9). When curve fitting was not possible, integration was performed by the trapeze method with the assumption that activity past the last measured bio distribution time point only decreased due to radio-active decay. The time activity curve of the tumor was fitted by a mono-exponential uptake function defined as $F(t)=a_0(1-\exp(-a_1 t))$.

TABLE 9

Residence times (in hr).

| Organ | $^{177}$Lu-DOTA-CC49 | $^{177}$Lu-Tetrazine |
|---|---|---|
| Blood | 14.76 | 0.067 |
| Heart Wall | 0.26 | 0.001 |
| Lungs | 0.82 | 0.031 |
| Liver | 28.57 | 0.302 |
| Spleen | 0.70 | 0.023 |
| Kidneys | 1.40 | 0.293 |
| Uterus | 0.53 | 0.026 |
| Ovaries | 0.113 | 0.0034 |
| Muscle | 9.96 | 0.19 |
| Bone | 5.46 | 0.239 |
| Brain | 0.172 | 0.001 |
| Stomach | 0.28 | 0.032 |
| Small Intestines | 1.50 | 0.082 |
| Large Intestines | 1.28 | 0.23 |
| Bladder Wall | 0.050 | 0.009 |
| Red Marrow | 1.18 | 0.0054 |
| Tumor | 50.84 | 3.93 |

For $^{177}$Lu-DOTA-CC49 some radioactivity was collected in the mixture of urine and feces. The remaining unmeasured activity was assigned to the remainder of the body (121 hr). For the pretargeted $^{177}$Lu-tetrazine a total of 97.8% ID was excreted. From the remaining activity in the animal, 20% was observed in the remainder or the body or corresponding to a residence time of 1 hr.

Human radiation dosimetry (Table 10) were calculated using the above measured residence times and the OLINDA/EXM program with the following assumptions: 10% of the blood residence time was assigned to the heart content and 90% was assigned to the remainder of the body; the activity measured in the small and large intestines were assigned to the organ content but the radiation dose was assigned to the organ itself; activity in the large intestine was assigned in equal part to the upper and lower large intestines; activity in the bone was assigned in equal parts to the trabecular and spongeous bone components. The bladder voiding model in OLINDA/EXM was used. Residence time to the red marrow was calculated as a fraction of blood residence time ($\tau_{marrow}=0.08\ \tau_{blood}$).

TABLE 10

Organ Radiation dose in mGy/MBq

| Organ | $^{177}$Lu-DOTA-CC49 | $^{177}$Lu-Tetrazine |
|---|---|---|
| Adrenals | 0.172 | 0.00162 |
| Brain | 0.0177 | 0.000146 |
| Breasts | 0.154 | 0.0013 |
| Gall Bladder Wall | 0.184 | 0.0018 |
| Lower Large Int. | 0.354 | 0.0363 |
| Small Intestines | 0.319 | 0.0101 |
| Stomach Wall | 0.208 | 0.00599 |
| Upper large Int. | 0.286 | 0.0231 |
| Heart Wall | 0.0944 | 0.000537 |
| Kidneys | 0.427 | 0.0425 |
| Liver | 1.33 | 0.0142 |
| Lungs | 0.0894 | 0.00288 |
| Muscle | 0.0466 | 0.000861 |
| Ovaries | 1.13 | 0.0341 |
| Pancreas | 0.172 | 0.00164 |
| Red marrow | 0.213 | 0.00302 |

TABLE 10-continued

Organ Radiation dose in mGy/MBq

| Organ | $^{177}$Lu-DOTA-CC49 | $^{177}$Lu-Tetrazine |
|---|---|---|
| Osteogenic cells | 0.799 | 0.00172 |
| Skin | 0.150 | 0.0029 |
| Spleen | 0.348 | 0.0112 |
| Testes | 0.155 | 0.00151 |
| Thymus | 0.158 | 0.00134 |
| Thyroid | 0.157 | 0.00132 |
| Bladder Wall | 0.261 | 0.104 |
| Uterus | 0.600 | 0.0293 |
| Total Body | 0.217 | 0.00287 |
| Effective Dose (mSv/MBq) | 0.447 | 0.0195 |

Radiation doses to the mouse organs were evaluated using the MIRD methodology where the S-factors in the mouse were calculated using a voxelized model of a mouse and the electron transport program EGSNRC to calculate energy deposition. The MOBY mouse phantom of Segars et al. was voxelized on a 0.2 mm grid and further modified to include the following organs: intestine wall and content, stomach wall and content, bladder wall and content and a 20 µl gall bladder. Finally, a 0.53 g tumor was added to the left side of the neck of the animal. Twenty-seven independent simulations, each for 10 millions decays, were performed with the program EGSNRC to calculate the energy deposition in each target organ for each source organ. The simulation included all decay particles from $^{177}$Lu as listed in www.nndc.bnl-.gov/MIRD tables. These S-factors were then used with the organ residence times measured above. Organ doses are listed in Table 11 for both compounds.

TABLE 11

Organ Radiation dose in a mouse model in mGy/MBq.

| Organ | $^{177}$Lu-DOTA-CC49 | $^{177}$Lu-Tetrazine |
|---|---|---|
| Lungs | 189 | 5 |
| Heart Wall | 347 | 2 |
| Kidneys | 328 | 58 |
| Liver | 942 | 10 |
| Pancreas | 57 | 2 |
| Spleen | 460 | 15 |
| Intestine Wall | 124 | 9 |
| Brain | 45 | 1 |
| Stomach Wall | 302 | 16 |
| Testes (ovaries) | 78 | 1 |
| Ribs | 333 | 8 |
| Thyroid | 114 | 1 |
| Femur | 261 | 8 |
| Cranium | 404 | 13 |
| Trachea | 153 | 2 |
| Spine | 475 | 8 |
| Spine (marrow) | 1136 | 7 |
| Bladder Wall | 354 | 168 |
| Skin | 62 | 1 |
| Gall Bladder | 157 | 2 |
| Tumor | 9573 | 479 |
| Whole Body | 601 | 5 |
| Effective Dose (mSv/MBq) | 344 | 15.6 |

Example 14

Synthesis of Dendrimeric Clearing Agents Functionalized with Galactose and Tetrazine Residues Synthesis of PPI-G1-(galactose)$_2$-(tetrazine)$_2$ (23)

Figure 17:
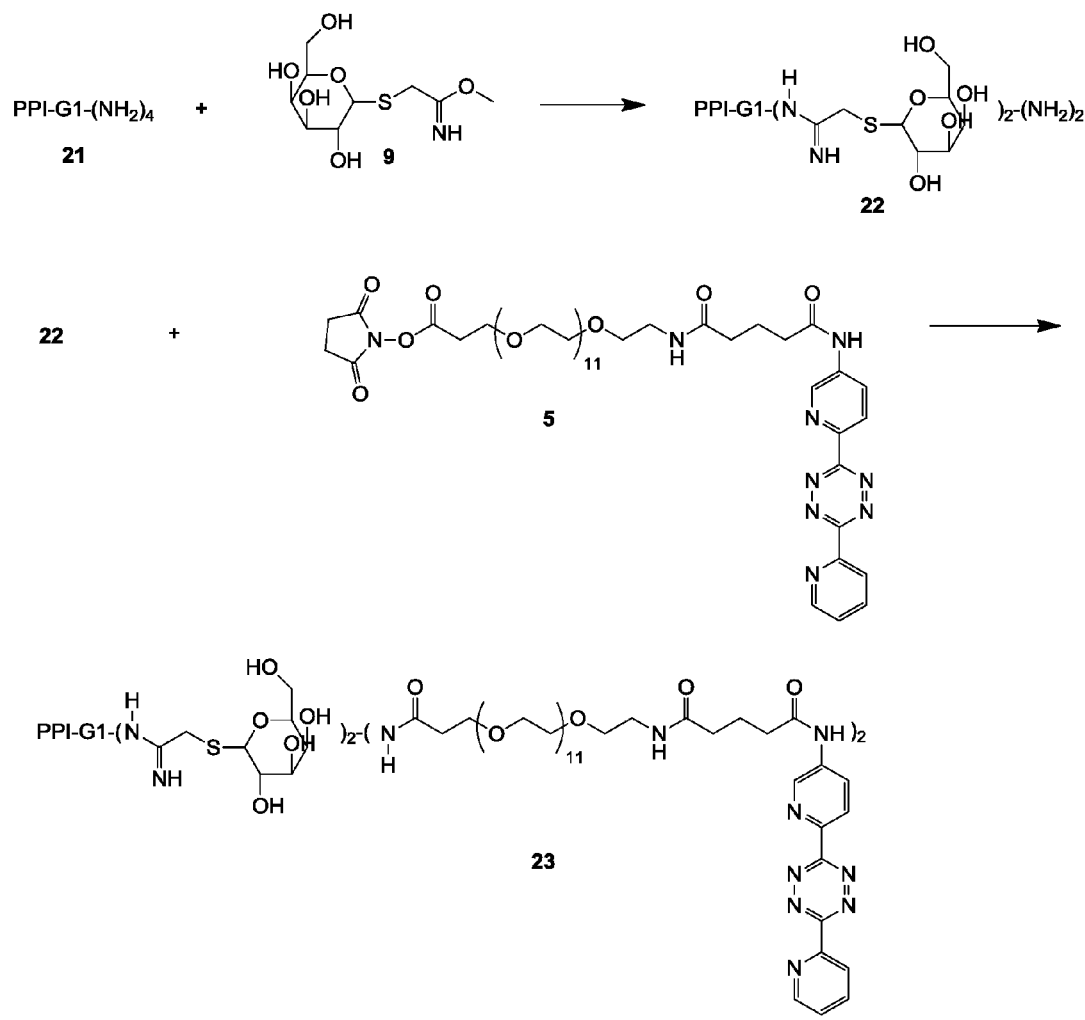
FIG. 17 depicts the synthesis route of PPI-G1-(galactose)$_2$-(tetrazine)$_2$ (23)

Reference is made to FIG. 17 detailing the synthesis route

PPI-G1-(galactose)$_2$-(NH$_2$)$_2$ (22)

PPI-G1-(NH$_2$)$_4$ (21; 35.86 mg; 1.13*10$^{-4}$ mol) was dissolved in water (1.5 mL), and acetic acid (30 mg; 5.09*10$^{-4}$ mol) was added. 2-Imino-2-methoxyethyl-β-D-thiogalacto pyranoside (9; 60.56 mg; 2.27*10$^{-4}$ mol) was added, and the reaction mixture was stirred for 2 hr at room temperature. Subsequently, the reaction mixture was lyophilized, to yield the product 22 as a white solid (86.0 mg; 97%).

$^1$H-NMR (D$_2$O): δ=4.52 (d, J=10 Hz, 2H, galactose H$_1$), 3.96 (d, J=2.8 Hz, 2H, galactose H$_2$), 3.75-3.5 (m, 14H, galactose H$_3$+H$_4$+H$_5$+H$_6$+H$_6$'+CH$_2$S), 3.45 (br. m, 4H, C$\underline{H}_2$NH(C=NH)), 3.02 (m, J=6.8 Hz, 4H, C$\underline{H}_2$NH$_2$), 3.0-2.8 (br. m, 12H, CH$_2$N), 1.97 (br. m, 8H, C$\underline{H}_2$CH$_2$N), 1.62 (br. m, 4H, NCH$_2$C$\underline{H}_2$CH$_2$CH$_2$N) ppm. ESI-MS: m/z=316.3, 551.4, 786.5, 1021.6 Da (calc: 787.1 Da).

PPI-G1-(galactose)$_2$-(tetrazine)$_2$ (23)

PPI-G1-(galactose)$_2$-(NH$_2$)$_2$ (22; 7.47 mg; 9.36*10$^{-6}$ mol) was dissolved in water (0.5 mL). Disodium hydrogenphosphate (6.00 mg; 4.21*10$^{-5}$ mol) was added to adjust the pH of the mixture to 9. Then, NHS-activated tetrazine (5; 19.9 mg; 1.87*10−5 mol) was added. The reaction mixture was stirred at room temperature for 1 hr, resulting in a clear, pink solution. Subsequently, the reaction mixture was lyophilized, to yield the product 23 as a pink solid (30.5 mg; 122%).

$^1$H-NMR (D$_2$O): δ=8.9-7.4 (br.m, 12H, tetrazine), 4.56 (d, 2H, galactose H$_1$), 3.99 (s, 2H, galactose H$_2$), 3.8-3.6 (m, 102H, PEG CH$_2$O+galactose H$_3$+H$_4$+H$_5$+H$_6$+H$_6$'+CH$_2$S), 3.43 (m, 4H, C$\underline{H}_2$NHCO), 3.36 (m, 4H, C$\underline{H}_2$NH(C=NH)), 3.21 (m, 4H, C$\underline{H}_2$NHCO), 2.9-2.6 (br. m, 12H, CH$_2$N), 2.51 (m, 4H, CH$_2$CO), 2.4-2.2 (br. m, 8H, CH$_2$CO), 2.0-1.65 (br. m, 12H, C$\underline{H}_2$CH$_2$N), 1.57 (br. m, 4H, NCH$_2$C$\underline{H}_2$CH$_2$CH$_2$N) ppm.

ESI-MS: m/z=1971.6, 2684.4, 3394.4 Da (calc: 2679.8 Da).

Synthesis of PPI-G3-(galactose)$_{12}$-(tetrazine)$_4$ (26)

Figure 18:
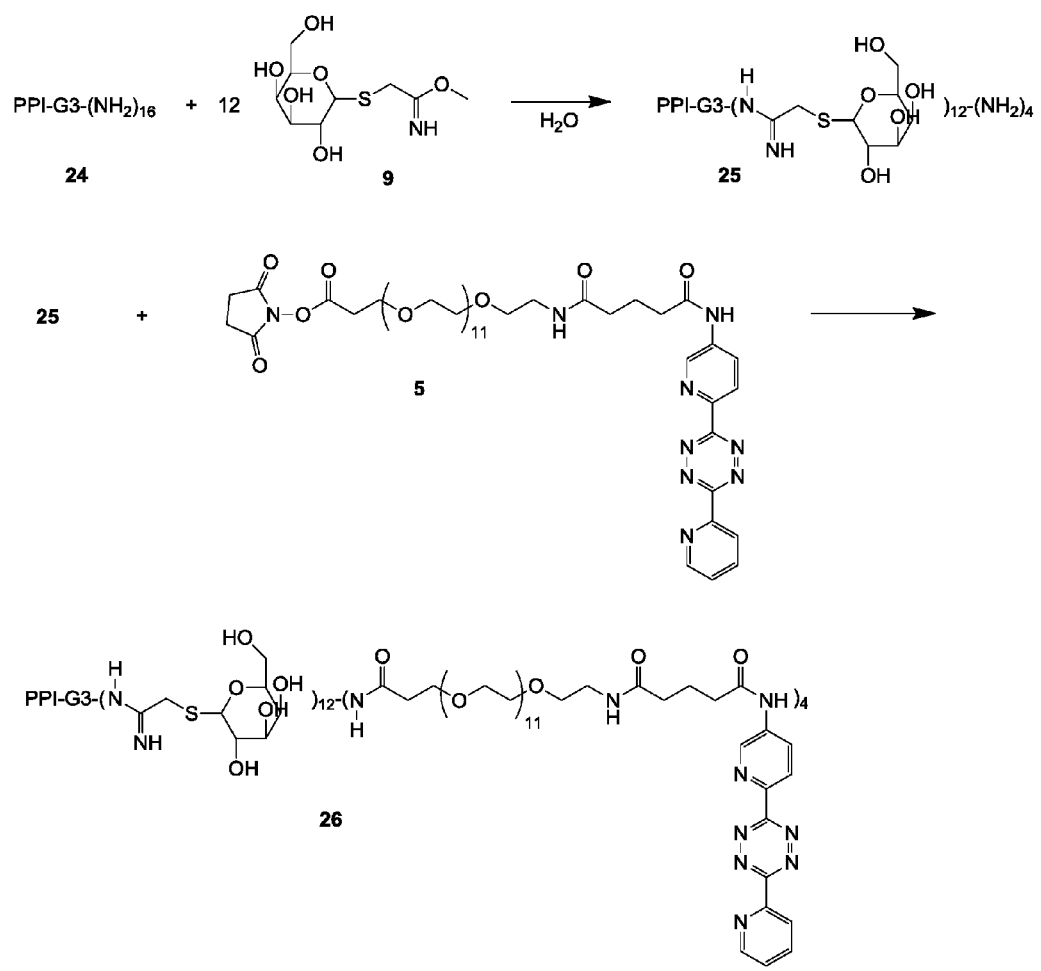
FIG. 18 depicts the synthesis route of PPI-G3-(galactose)$_{12}$-(tetrazine)$_4$ (26)

Reference is made to FIG. 18 detailing the synthesis route

PPI-G3-(galactose)$_{12}$-(NH$_2$)$_4$ (25)

PPI-G3-(NH$_2$)$_{16}$ (24; 33.8 mg; 2.00*10$^{-5}$ mol) was dissolved in water (0.6 mL), and acetic acid (10 mg; 1.67*10$^{-4}$ mol) was added. 2-Imino-2-methoxyethyl-O-D-thiogalacto pyranoside (9; 64.3 mg; 2.40*10$^{-4}$ mol) was added, and the reaction mixture was stirred for 2 hr at room temperature. Subsequently, the reaction mixture was diluted with water (2 mL) and lyophilized, to yield the product as a white solid (89 mg; 99%).

$^1$H-NMR (D$_2$O): δ=4.53 (d, J=9.2 Hz, 12H, galactose H$_1$), 3.99 (d, J=2.8 Hz, 12H, galactose H$_2$), 3.8-3.6 (m, 60H, galactose H$_3$+H$_4$+H$_5$+H$_6$+H$_6$'), 3.29 (br. m, 24H, C$\underline{H}_2$NH(C=NH)), 2.72 (br. m, 8H, C$\underline{H}_2$NH$_2$), 2.65-2.4 (br. m, 84H, CH$_2$N), 1.83 (br. m, 24H, C$\underline{H}_2$CH$_2$NH(C=NH)), 1.66 (br. m, 32H, C$\underline{H}_2$CH$_2$N), 1.46 (br. m, 4H, NCH$_2$C$\underline{H}_2$CH$_2$CH$_2$N) ppm. ESI-MS: m/z=3807.3, 4043.4, 4278.8, 4514.4, 4750.0, 4984.1 Da (calc: 4510.1 Da).

PPI-G3-(galactose)$_{12}$-(tetrazine)$_4$ (26)

PPI-G3-(galactose)$_{12}$-(NH$_2$)$_4$ (25; 10.0 mg; 2.34*10$^{-6}$ mol) was dissolved in water (0.6 mL) and NHS-activated tetrazine (5; 12.4 mg; 1.17*10$^{-5}$ mol) was added. The reaction mixture was stirred at room temperature for 1 hr, resulting in a clear, pink solution. Subsequently, the reaction mixture was diluted with water (3 mL) and lyophilized, to yield the product as a pink solid (21.1 mg; 100%).

$^1$H-NMR (D$_2$O): δ=8.7-7.3 (br.m, 40H, tetrazine), 4.54 (d, J=9.2 Hz, 12H, galactose H$_1$), 3.99 (br. m, 12H, galactose H$_2$), 3.9-3.6 (m, 355H, PEG CH$_2$O+galactose H$_3$+H$_4$+H$_5$+H$_6$+H$_6$'), 3.42 (br. m, 10H), 3.35 (br. m, 24H, C$\underline{H}_2$NH(C=NH)), 3.12 (br. m, 10H), 3.0-2.6 (br. m, 84H, CH$_2$N), 2.52 (br.m, 10H), 2.26 (br. m, 20H), 2.0-1.6 (br. m, 60H, C$\underline{H}_2$CH$_2$N) ppm. FT-IR: ν=3298, 2871, 1671, 1643, 1583, 1538, 1394, 1200, 1124, 1082 cm$^{-1}$.

Synthesis of PPI-G5-(galactose)$_{50}$-(tetrazine)$_{14}$ (29)

Figure 19:
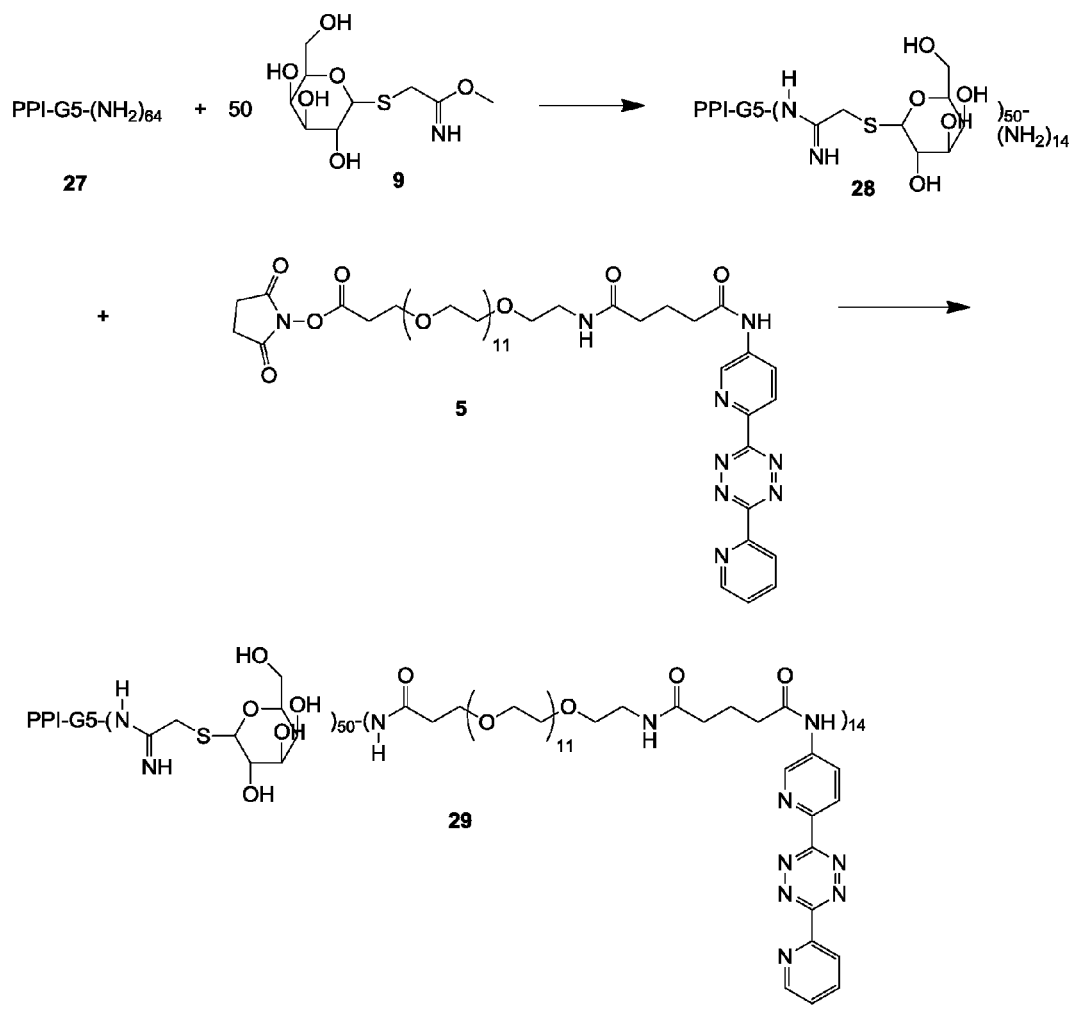
FIG. 19 depicts the synthesis route of PPI-G5-(galactose)$_{12}$-(tetrazine)$_4$ (29)

Reference is made to FIG. 19 detailing the synthesis route

PPI-G5-(galactose)$_{50}$-(NH$_2$)$_{14}$ (28)

PPI-G5-(NH$_2$)$_{64}$ (27; 20.9 mg; 2.92*10$^{-6}$ mol) was dissolved in water (0.6 mL), and acetic acid (17.5 mg; 2.92*10$^{-4}$ mol) was added. 2-Imino-2-methoxyethyl-β-D-thiogalacto pyranoside (9; 46.8 mg; 1.75*10$^{-4}$ mol) was added, and the reaction mixture was stirred for 4 hr at room temperature. Subsequently, the reaction mixture was diluted with water (2 mL) and lyophilized, to yield the product as a white solid (74.4 mg; 120%).

$^1$H-NMR (D$_2$O): δ=4.61 (d, J=9.2 Hz, 50H, galactose H$_1$), 4.04 (d, J=2.8 Hz, 50H, galactose H$_2$), 3.8-3.6 (m, 350H, galactose H$_3$+H$_4$+H$_5$+H$_6$+H$_6$'+CH$_2$S), 3.41 (br. m, 100H, C$\underline{H}_2$NH(C=NH)), 3.1-2.6 (br. m, 380H, CH$_2$N), 1.95 (br. m, 252H, C$\underline{H}_2$CH$_2$N), 1.98 (s, 270H, C$\underline{H}_3$COOH) ppm.

PPI-G5-(galactose)$_{50}$-(tetrazine)$_{14}$ (29)

PPI-G5-(galactose)$_{50}$-(NH$_2$)$_{14}$ (28; 28.3 mg; 1.25*10$^{-6}$ mol) was dissolved in water (0.6 mL). Disodium hydrogenphosphate (17.7 mg; 1.25*10$^{-4}$ mol) was added to adjust the pH of the mixture to 9. Then, NHS-activated tetrazine (5; 19.9 mg; 1.88*10$^{-5}$ mol) was added. The reaction mixture was stirred at room temperature for 90 min, resulting in a clear, pink solution. Subsequently, the reaction mixture was purified from low MW byproducts by elution over a PD-10 column. The high MW fractions were collected and lyophilized, to yield the product as a pink solid (10.9 mg; 27%).

$^1$H-NMR (D$_2$O): δ=8.9-7.6 (br.m, 105H, tetrazine), 4.59 (d, J=8.4 Hz, 50H, galactose H$_1$), 4.02 (s, 50H, galactose H$_2$), 3.9-3.5 (m, 1070H, PEG CH$_2$O+galactose H$_3$+H$_4$+H$_5$+H$_6$+H$_6$'+CH$_2$S), 3.41 (br. m, 158H), 3.0-2.6 (br. m, 380H, CH$_2$N), 2.47 (br.m, 40H), 2.35 (br. m, 80H), 2.1-1.7 (br. m, 252H, C$\underline{H}_2$CH$_2$N) ppm.

Some Embodiments of the Present Invention Relate to

1. A combination of an Administration Agent to be administered to a subject and a Clearing Agent to be administered to the same subject so as to remove circulating Administration Agent from the subject's blood, wherein the Administration Agent comprises a first Reactive Group, and wherein the Clearing Agent comprises a second Reactive Group, said first and second Reactive Groups being Bio-orthogonal Reactive Groups selected so as to be bio-orthogonally reactive towards each other wherein either of the Bio-orthogonal Reactive Groups is a dienophile and the other is a diene, wherein the dienophile is an 8-member ring dienophile satisfying formula (1):

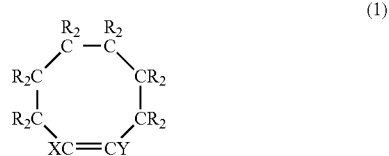

wherein each R independently denotes H, or, in at most six instances, a substituent selected from the group consisting of alkyl, O-alkyl, O-aryl, S-alkyl, F, Cl, Br, I, $SO_2$, $NO_2$, NR'R" with R' and R" each independently being H or alkyl, C(=O)Oalkyl, C(=O)Oaryl, CONR'R" with R' and R" each independently being H, aryl or alkyl, OCOalkyl, OCOaryl, NR'COalkyl with R' being H or alkyl, NR'COaryl with R' being or alkyl, NR'C(=O)Oalkyl with R' being H or alkyl, NR'C(=O)Oaryl with R' being H or alkyl, OCONR'alkyl with R' being H or alkyl, OCONR'aryl with R' being H or alkyl, NR'CONR"alkyl with R' and R" each independently being H or alkyl, NR'CONR"aryl with R' and R" each independently being H or alkyl, NR'CSNR"alkyl with R' and R" each independently being H or alkyl, and NR'CSNR"aryl with R' and R" each independently being H or alkyl, wherein two R moieties together may form a ring, and wherein X and Y each independently denote H, or a substituent selected from the group consisting of alkyl, O-alkyl, S-alkyl, F, Cl, Br, I, $SO_2$, $NO_2$, and NRR' with R and R' each independently being H or alkyl, or together form a bond, with one R forming a linkage, optionally via a spacer, to the respective Administration Agent or Clearing Agent and wherein the clearing agent further comprises one or more hexose-based moieties.

2. A combination according to claim 1, wherein the dienophile is an 8-member ring dienophile satisfying formula (1a):

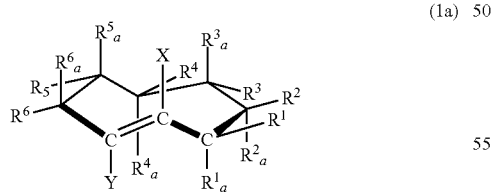

wherein each of X, Y, R, and $R_a$ independently denotes H, or, in at most six instances, a substituent selected from the group consisting of alkyl, O-alkyl, O-aryl, S-alkyl, Si-alkyl, F, Cl, Br, I, $SO_2$, $SO_3$, $SO_4$, $NO_2$, NR'R" with R' and R" each independently being H or alkyl, C(=O)Oalkyl, C(=O)Oaryl, CONR'R" with R' and R" each independently being H, aryl or alkyl, OCOalkyl, OCOaryl, NR'COalkyl with R' being H or alkyl, NR'COaryl with R' being or alkyl, NR'C(=O)Oalkyl with R' being H or alkyl, NR'C(=O)Oaryl with R' being H or alkyl, OCONR'alkyl with R' being H or alkyl, OCONR'aryl with R' being H or alkyl, NR'CONR"alkyl with R' and R" each independently being H or alkyl, NR'CONR"aryl with R' and R" each independently being H or alkyl, NR'CSNR"alkyl with R' and R" each independently being H or alkyl, and NR'CSNR"aryl with R' and R" each independently being H or alkyl; with one of R or $R_a$ comprised in a Linker Moiety, optionally via a spacer, to the Pre-targeting Probe or the Effector Probe; wherein two R or $R_a$ moieties together may form a ring; and wherein at least one and maximally four of $R_a$ is not hydrogen.

3. A combination according to embodiment 2, wherein the dienophile of formula (1a) satisfies one or more of the following requirements:

a) X is methyl
  b) Y is methyl;
  c) one or more substituents $R^2_a$, $R^3_a$, $R^4_a$, $R^5_a$ are O-alkyl;
  d) one or more substituents $R^2_a$, $R^3_a$, $R^4_a$, $R^5_a$ are O-aryl;

4. A combination according to embodiment 2 or 3, wherein X is methyl or hydrogen, Y is methyl or hydrogen, and $R^3_a$ or $R^4_a$ is O-alkyl or O-aryl.

5. A combination according to any one of the embodiments 1 to 4, wherein the diene is selected from the group consisting of compounds of the formulae (2), (3), (4), (5), (6), and (7) as defined below:

wherein $R^1$ is selected from the group consisting of alkyl, aryl, O-alkyl, O-aryl, C(=O)O-alkyl, C(=O)O-aryl, A-alkyl, S(=O)$_2$-alkyl, and NR'R" with R' and R" each independently being hydrogen or alkyl; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)Oalkyl;

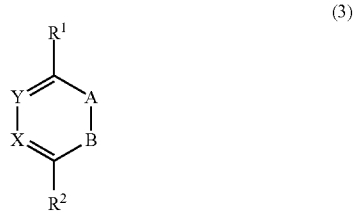

wherein $R^1$ and $R^2$ each independently are selected from the group consisting of H, alkyl, aryl, OH, C(=O)O-alkyl, C(=O)NH-alkyl, CF3, and NO2; A is selected from the group consisting of N-alkyl, N-aryl, C=O, and CN-alkyl; B is O; X is selected from the group consisting of CH, C-alkyl, C-aryl, CC(=O)O-alkyl and N; Y is selected from the group consisting of CH, C-alkyl, C-aryl, N, and $N^+O^-$;

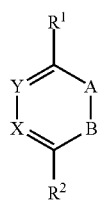

(4)

wherein $R^1$ and $R^2$ each independently are selected from the group consisting of H, alkyl, aryl, OH, C(=O)O-alkyl, C(=O)NH-alkyl, CF3, and NO2; A is selected from the group consisting of CO, Calkyl-alkyl. CN-alkyl, N-alkyl, and N-aryl; B is O; X is selected from the group consisting of CH, C-alkyl, C-aryl, CC(=O)O-alkyl and N; Y is selected from the group consisting of CH, C-alkyl, C-aryl, N, and $N^+O^-$;

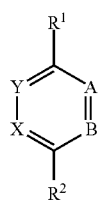

(5)

wherein $R^1$ and $R^2$ each independently are selected from the group consisting of H, alkyl, aryl, OH, C(=O)O-alkyl, C(=O)NH-alkyl, CF3, and NO2; A is selected from the group consisting of N, C-alkyl, C-aryl, and $N^+O^-$; B is N; X is selected from the group consisting of CH, C-alkyl, C-aryl, CC(=O)O-alkyl and N; Y is selected from the group consisting of CH, C-alkyl, C-aryl, N, and $N^+O^-$;

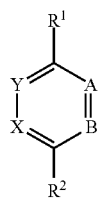

(6)

wherein $R^1$ is selected from the group consisting of H, alkyl, aryl, OH, C(=O)O-alkyl, CF3, and NO2; $R^2$ is selected from the group consisting of H, alkyl, aryl, CN, OH, C(=O)O-alkyl, CF3, and NO2; A is selected from the group consisting of N, CH, C-alkyl, C-aryl, CC(=O)O-alkyl, and $N^+O^-$; B is N; X is selected from the group consisting of CH, C-alkyl, C-aryl, CC(=O)O-alkyl and N; Y is selected from the group consisting of CH, CCN, C-alkyl, C-aryl, N, and $N^+O^-$;

(7)

wherein $R^1$ and $R^2$ each independently denote a substituent selected from the group consisting of 2-pyridyl, 3-pyridyl, 4-pyridyl, pyrimide, phenyl, and phenyl substituted with one or more electron-withdrawing groups, said electron-withdrawing groups preferably selected from the group consisting of NO2, F, Cl, Br, I, CN, COOH, COOR, $CONH_2$, CONHR, $CONR_2$, CHO, COR, $SO_2R$, $SO_2OR$, NO, and Ar, wherein R is $C_1$-$C_6$ alkyl and Ar stands for an aromatic group, preferably selected from phenyl, pyridyl, pyrimidyl, and naphthyl.

6. A combination according to any one of the preceding embodiments, wherein the Administration Agent is a Pre-targeting Probe, preferably comprising, as a primary targeting moiety, an antibody.

7. A combination according to any one of the embodiments 1 to 5, wherein the Administration Agent is an agent for targeted imaging or therapeutics.

8. A Clearing Agent comprising a Bio-orthogonal Reactive Group and one or more hexose-based moieties, and wherein the Bio-orthogonal Reactive Group is a diene or a dienophile as defined in any one of the embodiments 1 to 5.

9. The Clearing Agent of embodiment 8, wherein the hexose-based moieties are galactose moieties.

10. A pretargeting method comprising administering, to a subject, an Administration Agent which is a Pre-targeting Probe as defined in embodiment 6, allowing the agent to circulate in the subject's system for a period of time effective to achieve binding of the primary targeting moiety to a primary target, followed by clearing non-bound agent from the body by the administration of a Clearing Agent according to embodiment 8 or 9.

11. A method for removing a biomolecule from circulation in an animal or human subject, the method comprising administering an Administration Agent and a Clearing Agent, wherein the Administration Agent comprises a first Reactive Group, and wherein the Clearing Agent comprises a second Reactive Group, said first and second Reactive Groups being selected so as to be bio-orthogonally reactive towards each other and wherein the Reactive Groups are as defined in any one of the embodiments 1 to 5.

12. The use of an Administration Agent and a Clearing agent as defined in any one of the embodiments 1 to 5, for removing a biomolecule from circulation in an animal or human subject, wherein the Administration Agent comprises a moiety capable of binding to the biomolecule.

Further Embodiments of the Present Invention Relate to

Embodiment 1

A combination of an Administration Agent to be administered to a subject and a Clearing Agent to be administered to the same subject so as to remove circulating Administration Agent from the subject's blood, wherein the Administration Agent comprises a first Reactive Group, and wherein the Clearing Agent comprises a second Reactive Group, said first and second Reactive Groups being Bio-orthogonal Reactive Groups selected so as to be bio-orthogonally reactive towards each other.

Embodiment 2

A combination according to embodiment 1, wherein either of the Bio-orthogonal Reactive Groups is a dienophile and the other is a diene, wherein the dienophile is an 8-member ring dienophile satisfying formula (1):

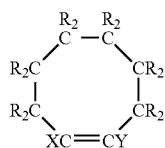
(1)

wherein each R independently denotes H, or, in at most six instances, a substituent selected from the group consisting of alkyl, O-alkyl, O-aryl, S-alkyl, F, Cl, Br, I, SO2, NO2, NR'R" with R' and R" each independently being H or alkyl, C(=O)Oalkyl, C(=O)Oaryl, CONR'R" with R' and R" each independently being H, aryl or alkyl, OCOalkyl, OCOaryl, NR'COalkyl with R' being H or alkyl, NR'COaryl with R' being or alkyl, NR'C(=O)Oalkyl with R' being H or alkyl, NR'C(=O)Oaryl with R' being H or alkyl, OCONR'alkyl with R' being H or alkyl, OCONR' aryl with R' being H or alkyl, NR'CONR"alkyl with R' and R" each independently being H or alkyl, NR'CONR"aryl with R' and R" each independently being H or alkyl, NR'CSNR"alkyl with R' and R" each independently being H or alkyl, and NR'CSNR"aryl with R' and R" each independently being H or alkyl, wherein two R moieties together may form a ring, and wherein X and Y each independently denote H, or a substituent selected from the group consisting of alkyl, O-alkyl, S-alkyl, F, Cl, Br, I, SO2, NO2, and NRR' with R and R' each independently being H or alkyl, or together form a bond, with one R forming a linkage, optionally via a spacer, to the respective Administration Agent or Clearing Agent.

Embodiment 3

A combination according to embodiment 2, wherein the dienophile is an 8-member ring dienophile satisfying formula (1a):

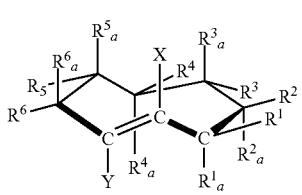
(1a)

wherein each of X, Y, R, and $R_a$ independently denotes H, or, in at most six instances, a substituent selected from the group consisting of alkyl, O-alkyl, O-aryl, S-alkyl, Si-alkyl, F, Cl, Br, I, $SO_2$, $SO_3$, $SO_4$, $NO_2$, NR'R" with R' and R" each independently being H or alkyl, C(=O)Oalkyl, C(=O)Oaryl, CONR'R" with R' and R" each independently being H, aryl or alkyl, OCOalkyl, OCOaryl, NR'COalkyl with R' being H or alkyl, NR'COaryl with R' being or alkyl, NR'C(=O)Oalkyl with R' being H or alkyl, NR'C(=O)Oaryl with R' being H or alkyl, OCONR'alkyl with R' being H or alkyl, OCONR'aryl with R' being H or alkyl, NR'CONR"alkyl with R' and R" each independently being H or alkyl, NR'CONR"aryl with R' and R" each independently being H or alkyl, NR'CSNR"alkyl with R' and R" each independently being H or alkyl, and NR'CSNR"aryl with R' and R" each independently being H or alkyl; with one of R or $R_a$ comprised in a Linker Moiety, optionally via a spacer, to the Pre-targeting Probe or the Effector Probe; wherein two R or $R_a$ moieties together may form a ring; and wherein at least one and maximally four of $R_a$ is not hydrogen.

Embodiment 4

A combination according to embodiment 3, wherein the dienophile of formula (1a) satisfies one or more of the following requirements:
a) X is methyl
b) Y is methyl;
c) one or more substituents $R^2_a$, $R^3_a$, $R^4_a$, $R^5_a$ are O-alkyl;
d) one or more substituents $R^2_a$, $R^3_a$, $R^4_a$, $R^5_a$ are O-aryl;

Embodiment 5

A combination according to embodiment 3 or 4, wherein X is methyl or hydrogen, Y is methyl or hydrogen, and $R^3_a$ or $R^4_a$ is O-alkyl or O-aryl.

Embodiment 6

A combination according to any one of the embodiments 2 to 5, wherein the diene is selected from the group consisting of compounds of the formulae (2), (3), (4), (5), (6), and (7) as defined below:

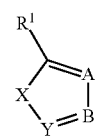
(2)

wherein $R^1$ is selected from the group consisting of alkyl, aryl, O-alkyl, O-aryl, C(=O)O-alkyl, C(=O)O-aryl, A-alkyl, S(=O)$_2$-alkyl, and NR'R" with R' and R" each independently being hydrogen or alkyl; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)Oalkyl;

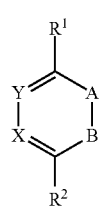
(3)

wherein $R^1$ and $R^2$ each independently are selected from the group consisting of H, alkyl, aryl, OH, C(=O)O-alkyl, C(=O)NH-alkyl, CF3, and NO2; A is selected from the group consisting of N-alkyl, N-aryl, C=O, and CN-alkyl; B is O; X is selected from the group consisting of CH, C-alkyl, C-aryl, CC(=O)O-alkyl and N; Y is selected from the group consisting of CH, C-alkyl, C-aryl, N, and $N^+O^-$;

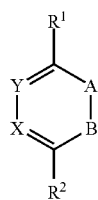

(4)

wherein $R^1$ and $R^2$ each independently are selected from the group consisting of H, alkyl, aryl, OH, C(=O)O-alkyl, C(=O)NH-alkyl, CF3, and NO2; A is selected from the group consisting of CO, Calkyl-alkyl. CN-alkyl, N-alkyl, and N-aryl; B is O; X is selected from the group consisting of CH, C-alkyl, C-aryl, CC(=O)O-alkyl and N; Y is selected from the group consisting of CH, C-alkyl, C-aryl, N, and $N^+O^-$;

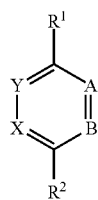

(5)

wherein $R^1$ and $R^2$ each independently are selected from the group consisting of H, alkyl, aryl, OH, C(=O)O-alkyl, C(=O)NH-alkyl, CF3, and NO2; A is selected from the group consisting of N, C-alkyl, C-aryl, and $N^+O^-$; B is N; X is selected from the group consisting of CH, C-alkyl, C-aryl, CC(=O)O-alkyl and N; Y is selected from the group consisting of CH, C-alkyl, C-aryl, N, and $N^+O^-$;

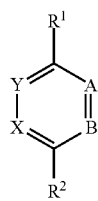

(6)

wherein $R^1$ is selected from the group consisting of H, alkyl, aryl, OH, C(=O)O-alkyl, CF3, and NO2; $R^2$ is selected from the group consisting of H, alkyl, aryl, CN, OH, C(=O)O-alkyl, $CF_3$, and $NO_2$; A is selected from the group consisting of N, CH, C-alkyl, C-aryl, CC(=O)O-alkyl, and $N^+O^-$; B is N; X is selected from the group consisting of CH, C-alkyl, C-aryl, CC(=O)O-alkyl and N; Y is selected from the group consisting of CH, CCN, C-alkyl, C-aryl, N, and $N^+O^-$;

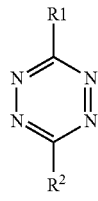

(7)

wherein $R^1$ and $R^2$ each independently denote a substituent selected from the group consisting of 2-pyridyl, 3-pyridyl, 4-pyridyl, pyrimide, phenyl, and phenyl substituted with one or more electron-withdrawing groups, said electron-withdrawing groups preferably selected from the group consisting of NO2, F, Cl, Br, I, CN, COOH, COOR, $CONH_2$, CONHR, $CONR_2$, CHO, COR, $SO_2R$, $SO_2OR$, NO, and Ar, wherein R is $C_1$-$C_6$ alkyl and Ar stands for an aromatic group, preferably selected from phenyl, pyridyl, pyrimidyl, and naphthyl.

Embodiment 7

A combination according to any one of the preceding embodiments, wherein the Administration Agent is a Pre-targeting Probe, preferably comprising, as a primary targeting moiety, an antibody.

Embodiment 8

A combination according to any one of the embodiments 1 to 6, wherein the Administration Agent is an agent for targeted imaging or therapeutics.

Embodiment 9

A Clearing Agent comprising a Bio-orthogonal Reactive Group and one or more hexose, preferably galactose moieties.

Embodiment 10

A Clearing Agent according to embodiment 9, wherein the Bio-orthogonal Reactive Group is a diene or a dienophile as defined in any one of the embodiments 2 to 5.

Embodiment 11

A pretargeting method comprising administering, to a subject, an Administration Agent which is a Pre-targeting Probe as defined in embodiment 7, allowing the agent to circulate in the subject's system for a period of time effective to achieve binding of the primary targeting moiety to a primary target, followed by clearing non-bound agent from the body by the administration of a Clearing Agent as defined in any one of the embodiments 1-6, preferably a Clearing Agent according to embodiment 9 or 10.

Embodiment 12

A method for removing a biomolecule from circulation in an animal or human subject, the method comprising administering an Administration Agent and a Clearance Agent, wherein the Administration Agent comprises a first Reactive Group, and wherein the Clearing Agent comprises a second Reactive Group, said first and second Reactive Groups being selected so as to be bio-orthogonally reactive towards each other.

Embodiment 13

A method according to embodiment 12, wherein the Reactive Groups are as defined in any one of the embodiments 2 to 6.

Embodiment 14

The use of an Administration Agent and a Clearing agent as defined in any one of the embodiments 1 to 6, for removing a biomolecule from circulation in an animal or human subject, wherein the Administration Agent comprises a moiety capable of binding to the biomolecule.

The invention claimed is:

1. A combination of an administration agent to be administered to a subject and a clearing agent to be administered to the same subject that is configured to remove circulating administration agent from the subject's blood, wherein the administration agent includes a linkage by which said administration agent is linked to a first reactive group, and wherein the clearing agent includes a linkage by which said clearing agent is linked to a second reactive group, said first and second reactive groups being bio-orthogonal reactive groups selected so as to be bio-orthogonally reactive towards each other wherein either of the bio-orthogonal reactive groups is a dienophile and the other is a diene, wherein the dienophile is an 8-member ring dienophile satisfying formula (1):

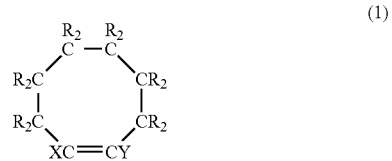

(1)

wherein each R independently denotes H, or, in at most six instances, a substituent selected from the group consisting of alkyl, aryl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl OCS-aryl, SCS-alkyl, SCS-aryl, F, Cl, Br, I, N$_3$, SO$_2$H, SO$_3$H, SO$_4$H, PO$_3$H, PO$_4$H, OH, SH, NO$_2$, NO, CN, OCN, SCN, NCO, NCS, CF$_3$, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl, wherein two R moieties together may form a ring, and wherein X and Y each independently denote H, or a substituent selected from the group consisting of alkyl, O-alkyl, S-alkyl, F, Cl, Br, I, SO2, NO2, and NRR' with R and R' each independently being H or alkyl, or together form a bond, with one R forming said linkage, optionally via a spacer, to the respective administration agent or clearing agent.

2. A combination according to claim 1, wherein the clearing agent further comprises a scaffold selected from the group consisting of a protein, a dendrimer, and a polymer, or a particle scaffold such as a micro- or nanoparticle.

3. A combination according to claim 1, wherein the clearing agent further comprises one or more hexoses.

4. A combination according to claim 1, wherein the dienophile is an 8-member ring dienophile satisfying formula (1a):

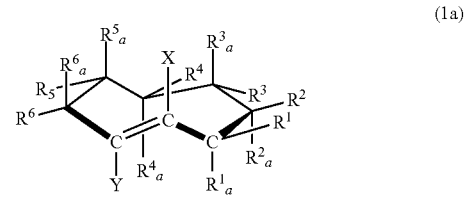

(1a)

wherein each of X, Y, R, and R$_a$ independently denotes H, or, in at most six instances, a substituent selected from the group consisting of alkyl, aryl, O-aryl, O-alkyl, S-aryl, S-alkyl, S(O)-aryl, S(O)-alkyl, S(O)$_2$-aryl, S(O)$_2$-alkyl, Si-aryl, Si-alkyl, Si—O-alkyl, OCO-alkyl, OCO-aryl, SCO-alkyl, SCO-aryl, OCS-alkyl, OCS-aryl, SCS-alkyl, SCS-aryl, F, Cl, Br, I, N$_3$, SO$_2$H, SO$_3$H, SO$_4$H, PO$_3$H, PO$_4$H, OH, SH, NO$_2$, NO, CN, OCN, SCN, NCO, NCS, CF$_3$, NR'R" with R' and R" each independently being H or alkyl, aryl, C(=O)O-alkyl, C(=O)O-aryl, C(=S)O-alkyl, C(=S)O-aryl, C(=O)S-alkyl, C(=O)S-aryl, C(=S)S-alkyl, C(=S)S-aryl, C(=O)NR'R" with R' and R" each independently being H, aryl or alkyl, NR'CO-alkyl with R' being H, alkyl or aryl, NR'CO-aryl with R' being H, alkyl or aryl, NR'C(=O)O-alkyl with R' being H, alkyl, or aryl, NR'C(=O)O-aryl with R' being H, alkyl or aryl, OCONR'-alkyl with R' being H, alkyl or aryl, OCONR'-aryl with R' being H, alkyl or aryl, NR'CONR"-alkyl with R' and R" each independently being H, alkyl or aryl, NR'CONR"-aryl with R' and R" each independently being H, alkyl or aryl, NR'CSNR"-alkyl with R' and R" each independently being H, alkyl or aryl, and NR'CSNR"-aryl with R' and R" each independently being H, alkyl or aryl, CR'NR" with R' and R" each independently being H, alkyl or aryl; with one of R or R$_a$ comprised in a Linker Moiety, optionally via a spacer, to the; administration agent or the clearing agent wherein two R or R$_a$ moieties together may form a ring; and wherein at least one and maximally four of R$_a$ is not hydrogen.

5. A combination according to claim 4, wherein the dienophile of formula (1a) satisfies one or more of the following requirements:
a) X is methyl
b) Y is methyl;
c) one or more substituents $R^2_a$, $R^3_a$, $R^4_a$, $R^5_a$ are O-alkyl;
d) one or more substituents $R^2_a$, $R^3_a$, $R^4_a$, $R^5_a$ are O-aryl;
e) one or more substituents $R^2_a$, $R^3_a$, $R^4_a$, $R^5_a$ are aryl;
f) one or more substituents $R^2_a$, $R^3_a$, $R^4_a$, $R^5_a$ are alkyl.

6. A combination according to claim 4, wherein X is methyl or hydrogen, Y is methyl or hydrogen, and $R^3_a$ or $R^4_a$ is O-alkyl or O-aryl.

7. A combination according to claim 1, wherein the diene is selected from the group consisting of compounds of the formulae (2), (3), (4), (5) and (6) as defined below:

(2)

wherein R$^1$ is selected from the group consisting of H, alkyl, aryl, CF$_3$, CF$_2$—R', OR', SR', C(=O)R', C(=S)R', C(=O)

O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", NR'C(=O)NR"R'", NR'C(=S)N'R'R'" with R', R", and R'" each independently being H, aryl or alkyl; A and B each independently are selected from the group consisting of alkyl-substituted carbon, aryl substituted carbon, nitrogen, N⁺O⁻, N⁺R with R being alkyl, with the proviso that A and B are not both carbon; X is selected from the group consisting of O, N-alkyl, and C=O, and Y is CR with R being selected from the group consisting of H, alkyl, aryl, C(=O)OR', C(O)SR', C(=S)OR', C(=S)SR', C(=O)NR'R" with R' and R" each independently being H, aryl or alkyl;

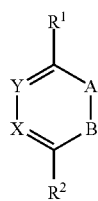

(3)

wherein $R^1$ and $R^2$ each independently are selected from the group consisting of H, alkyl, aryl, $CF_3$, $CF_2$—R', $NO_2$, OR', SR', C(=O)R', C(=S)R', OC(=O)R'", SC(=O)R'", OC(=S)R'", SC(=S)R'", S(=O)R', S(=O)$_2$R'", S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R'R" with R' and R" each independently being H, aryl or alkyl, and R'" independently being aryl or alkyl; A is selected from the group consisting of N-alkyl, N-aryl, C=O, and CN-alkyl; B is O or S; X is selected from the group consisting of N, CR, C-alkyl, C-aryl, CC(=O)R', CC(=S)R', CS(=O)R', CS(=O)$_2$R'", CC(=O)O—R', CC(=O)S—R', CC(=S)O—R', CC(=S)S—R', CC(=O)NR'R", CC(=S)NR'R", R' and R" each independently being H, aryl or alkyl and R'" independently being aryl or alkyl; Y is selected from the group consisting of CH, C-alkyl, C-aryl, N, and N⁺O⁻;

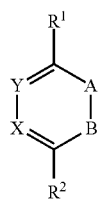

(4)

wherein $R^1$ and $R^2$ each independently are selected from the group consisting of H, alkyl, aryl, OH, C(=O)O-alkyl, C(=O)NH-alkyl, CF3, and NO2; A is selected from the group consisting of CO, Calkyl-alkyl, CN-alkyl, N-alkyl, and N-aryl; B is O; X is selected from the group consisting of CH, C-alkyl, C-aryl, CC(=O)O-alkyl and N; Y is selected from the group consisting of CH, C-alkyl, C-aryl, N, and N⁺O⁻:

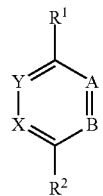

(5)

wherein $R^1$ and $R^2$ each independently are selected from the group consisting of H, alkyl, aryl, $CF_3$, $CF_2$—R', $NO_2$, OR', SR', C(=O)R', C(=S)R', OC(=O)R'", SC(=O)R'", OC(=S)R'", SC(=S)R'", S(=O)R', S(=O)$_2$R'", S(=O)$_2$NR'R", C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR'R", NR'C(=S)N'R'R" with R' and R" each independently being H, aryl or alkyl, and R'" independently being aryl or alkyl; A is selected from the group consisting of N, C-alkyl, C-aryl, and N⁺O⁻; B is N; X is selected from the group consisting of N, CH, C-alkyl, C-aryl, CC(=O)R', CC(=S)R', CS(=O)R', CS(=O)$_2$R'", CC(=O)O—R', CC(=O)S—R', CC(=S)O—R', CC(=S)S—R', CC(=O)NR'R", CC(=S)NR'R", R' and R" each independently being H, aryl or alkyl and R'" independently being aryl or alkyl; Y is selected from the group consisting of CH, C-alkyl, C-aryl, N, and N⁺O⁻:

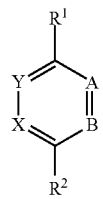

(6)

wherein $R^1$ is selected from the group consisting of H, alkyl, aryl, OH, C(=O)O-alkyl, CF3, and NO2; $R^2$ is selected from the group consisting of H, alkyl, aryl, CN, OH, C(=O)O-alkyl, CF3, and NO2; A is selected from the group consisting of N, CH, C-alkyl, C-aryl, CC(=O)O-alkyl, and N⁺O⁻; B is N; X is selected from the group consisting of CH, C-alkyl, C-aryl, CC(=O)O-alkyl and N; Y is selected from the group consisting of CH, CCN, C-alkyl, C-aryl, N, and N⁺O⁻.

8. A combination according to claim 1, wherein the administration agent is a pre-targeting probe, preferably comprising, as a primary targeting moiety, an antibody.

9. A combination according to claim 1, wherein the administration agent is an agent for targeted imaging or therapeutics.

10. A combination according to claim 1, wherein the diene is selected from the formulae (5), (6) and (7) as defined below:

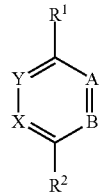

(5)

wherein R¹ and R² each independently are selected from the group consisting of H, alkyl, aryl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR'R'', NR'C(=S)N'R'R'' with R' and R'' each independently being H, aryl or alkyl, and R''' independently being aryl or alkyl; A is selected from the group consisting of N, C-alkyl, C-aryl, and $N^+O^-$; B is N; X is selected from the group consisting of N, CH, C-alkyl, C-aryl, CC(=O)R', CC(=S)R', CS(=O)R', CS(=O)$_2$R''', CC(=O)O—R', CC(=O)S—R', CC(=S)O—R', CC(=S)S—R', CC(=O)NR'R'', CC(=S)NR'R'', R' and R'' each independently being H, aryl or alkyl and R''' independently being aryl or alkyl; Y is selected from the group consisting of CH, C-alkyl, C-aryl, N, and $N^+O^-$;

(6)

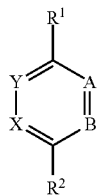

wherein R¹ is selected from the group consisting of H, alkyl, aryl, OH, C(=O)O-alkyl, CF3, and NO2; R² is selected from the group consisting of H, alkyl, aryl, CN, OH, C(=O)O-alkyl, CF3, and NO2; A is selected from the group consisting of N, CH, C-alkyl, C-aryl, CC(=O)O-alkyl, and $N^+O^-$; B is N; X is selected from the group consisting of CH, C-alkyl, C-aryl, CC(=O)O-alkyl and N; Y is selected from the group consisting of CH, CCN, C-alkyl, C-aryl, N, and $N^+O^-$;

(7)

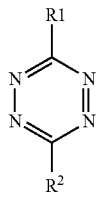

wherein R¹ and R² each independently denote a substituent selected from the group consisting of H, 2-pyridyl, 3, pyridyl, 4-pyridyl, 2,6-pyrimidyl, 2,5-pyrimidyl, 3,5-pyrimidyl, 2,4-pyrimidyl, or phenyl, optionally substituted with one or more electron-withdrawing groups such as $NO_2$, F, Cl, CF3, CN, COOH, COOR, $CONH_2$, CONHR, $CONR_2$, CHO, COR, $SO_2R$, $SO_2OR$, NO, Ar, wherein R is $C_1$-$C_6$ alkyl and Ar stands for an aromatic group, particularly phenyl, pyridyl, or naphthyl.

* * * * *